US007339046B2

(12) United States Patent
Welsh et al.

(10) Patent No.: US 7,339,046 B2
(45) Date of Patent: Mar. 4, 2008

(54) CFTR WITH A PARTIALLY DELETED R DOMAIN AND USES THEREOF

(75) Inventors: Michael J. Welsh, Riverside, IA (US); Lynda S. Ostedgaard, Iowa City, IA (US); Joseph Zabner, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 562 days.

(21) Appl. No.: 10/367,507

(22) Filed: Feb. 14, 2003

(65) Prior Publication Data

US 2003/0235885 A1 Dec. 25, 2003

Related U.S. Application Data

(60) Provisional application No. 60/358,074, filed on Feb. 19, 2002.

(51) Int. Cl.
*A61K 38/16* (2006.01)
*C07H 21/04* (2006.01)
(52) U.S. Cl. .................. 536/23.5; 530/23.1; 530/24.2; 435/69.1; 435/320.1; 435/252.3; 435/325; 435/235.1
(58) Field of Classification Search ...................... None
See application file for complete search history.

(56) References Cited

OTHER PUBLICATIONS

Welsh, M. et al, "Cystic Fibrosis", (1995), *McGraw-Hill Health Professions Division*, 3: (3799-3839).
Karp PH, Moninger TO, Weber SP, Nesselhauf TS, Launspach JL, Zabner J, Welsh MJ. An in vitro model of differentiated human airway epithelia. Methods for establishing primary cultures. Methods Mol Biol 2002;188:115-37.
Baldursson O, Ostedgaard LS, Rokhlina T, Cotton JF, Welsh MJ. Cystic fibrosis transmembrane conductance regulator Cl-channels with R domain deletions and translocations show phosphorylation-dependent and independent activity. J Biol Chem 2001;276(3):1904-1910.
Davies JC, Geddes DM, Alton EW. Gene therapy for cystic fibrosis. J Gene Med 2001;3(5):409-417.
Halbert CL, Allen JM, Miller AD. Adeno-associated virus type 6 (AAV6) vectors mediate efficient transduction of airway epithelial cells in mouse lungs compared to that of AAV2 vectors. J Virol 2001;75(14):6615-6624.
Nagel G, Szellas T, Riordan JR, Friedrich T, Hartung K. Nonspecific activation of the epithelial sodium channel by the CFTR chloride channel. EMBO Rep 2001;2(3):249-254.
Ostedgaard LS, Baldursson O, Welsh MJ. Regulation of the cystic fibrosis transmembrane conductance regulator Cl-channel by its R domain. J Biol Chem 2001;276(11):7689-7692.
Walters RW, Yi SM, Keshavjee S, Brown KE, Welsh MJ, Chiorini JA, Zabner J. Binding of adeno-associated virus type 5 to 2,3-linked sialic acid is required for gene transfer. J Biol Chem 2001;276(23):20610-20616.

Athanasopoulos T, Fabb S, Dickson G. Gene therapy vectors based on adeno-associated virus: characteristics and applications to acquired and inherited diseases (review). Int J Mol Med 2000;6(4):363-375.
Carter PJ, Samulski RJ. Adeno-associated viral vectors as gene delivery vehicles. Int J Mol Med 2000;6(1):17-27.
Csanady L, Chan KW, Seto-Young D, Kopsco DC, Nairn AC, Gadsby DC. Severed channels probe regulation of gating of cystic fibrosis transmembrane conductance regulator by its cytoplasmic domains. J Gen Physiol 2000;116:477-500.
Ma J. Stimulatory and inhibitory functions in the R domain of CFTR chlorine channel. News Physiol Sci 2000;154-158.
Ostedgaard LS, Baldursson O, Vermeer DW, Welsh MJ. A functional R domain from cystic fibrosis transmembrane conductance regulator is predominantly unstructured in solution. Proc Natl Acad Sci U.S.A. 2001;97(10):5657-5662.
Welsh MJ et al. The Metabolic and Molecular Basis of Inherited Disease. eds. Scirver, Beaudet, Sly, Valle, Childs & Vogelstein 2000;(McGraw-Hill, New York) pp. 5121-5189.
Xie J, Zhao J, Davis PB, Ma J. Conformation, independent of charge, in the R domain affects cystic fibrosis transmembrane conductance regulator channel openings. Biophys J 2000;78(3):1293-1305.
Zabner J, Seiler M, Walters R, Kotin RM, Fulgeras W, Davidson BL, Chiorini JA. Adeno-associated virus type 5 (AAV5) but not AAV2 binds to the apical surfaces of airway epithelia and facilitates gene transfer. J Virol 2000;74(8):3852-3858.
Chang XB, Cui L, Hou YX, Jensen TJ, Aleksandrov AA, Mengos A, Riordan JR. Removal of multiple arginine-framed trafficking signals overcomes misprocessing of delta F508 CFTR present in most patients with cystic fibrosis. Mol Cell 1999;4(1):137-142.
Flotte TR. Gene therapy for cystic fibrosis. Curr Opin Mol Ther, 1999;1(4):510-516.
Gadsby DC, Nairn AC. Control of CFTR channel gating by phosphorylation and nucleotide hydrolysis. Physiol Rev 1999;79(1):S77-S107.
Ostedgaard LS, Zeiher B, Welsh MJ. Processing of CFTR bearing the P574H mutation differs from wild-type and deltaF508-CFTR. J Cell Sci, 1999;112(Pt 13):2091-2098.
Schwiebert EM, Benos DJ, Egan ME, Stutts MJ, Guggino WB. CFTR is a conductance regulator as well as a chloride channel. Physiol Rev 1999;79(1 Suppl):S145-166.
Sheppard DN, Welsh MJ. Structure and function of the CFTR chloride channel. Physiol Rev 1999;79(1 Suppl):S23-S45.

(Continued)

*Primary Examiner*—Gary B. Nickol
*Assistant Examiner*—Nirmal S. Basi
(74) *Attorney, Agent, or Firm*—Arent Fox LLP

(57) ABSTRACT

The present invention offers new therapies for treating Cystic Fibrosis (CF), that are based on novel DNA molecules and proteins encoded by the DNA molecules. The present invention features DNA molecules encoding CFTR having a partially deleted R domain. The partial deletions in the R domain are between residues 708 and 835 of the wild-type CFTR.

5 Claims, 6 Drawing Sheets
(1 of 6 Drawing Sheet(s) Filed in Color)

OTHER PUBLICATIONS

Vankeerberghen A, Lin W, Jaspers M, Cuppens H, Nilius B, Cassiman JJ. Functional characterization of the CFTR R domain using CFTR/MDR1 hybrid and deletion constructs. Biochemistry 1999;38(45):14988-14998.

Walters RW, Grunst T, Bergelson JM, Finberg RW, Welsh MJ, Zabner J. Basolateral localization of fiber receptors limits adenovirus infection from the apical surface of airway epithelia. J Biol Chem 1999;274(15):10219-10226.

Fasbender A, Lee JH, Walters RW, Moniger TO, Zabner J, Welsh MJ. Incorporation of adenovirus in calcium phosphate precipitates enhances gene transfer to airway epithelia in vitro and in vivo. J Clin Invest 1998;102(1):184-193.

Summerford C, Samulski RJ. Membrane-associated heparan sulfate proteoglycan is a receptor for adeno-associated virus type 2 virions. J Virol 1998;72(2):1438-1445.

Vankeerberghen A, Wei L, Jaspers M, Cassimm JJ, Nilius B, Cuppens H. Characterization of 19 disease-associated missense mutations in the regulatory domain of the cystic fibrosis transmembrane conductance regulator. Hum Mol Genet 1998;7(11):1761-1769.

Zabner J, Smith JJ, Karp PH, Widdicombe JH, Welsh MJ. Loss of CFTR chloride channels alters salt absorption by cystic fibrosis airway epithelia in vitro. Mol Cell 1998;2(3):397-403.

Zhang L, Wang D, Fischer H, Fan PD, Widdicombe JH, Kan YW, Dong JY. Efficient expression of CFTR function with adeno-associated virus vectors that carry shortened CFTR genes. Proc Natl Acad Sci U S A 1998 18;95(17):10158-10163.

Ma J, Zhao J, Drumm ML, Xie J, Davis PB. Function of the R domain in the cystic fibrosis transmembrane conductance regulator chloride channel. J Biol Chem 1997;272:28133-28141.

Winter MC, Welsh MJ. Stimulation of CFTR activity by its phosphorylated R domain. Nature 1997;389(6648):294-296.

Wilkinson DJ, Strong TV, Mansoura MK, Wood DL, Smith SS, Collins FS, Dawson DC. CFTR activation: additive effects of stimulatory and inhibitory phosphorylation sites in the R domain. Am J Physiol 1997;273(1 Pt):L127-L133.

Dong JY, Fan PD, Frizzell RA. Quantitative analysis of the packaging capacity of recombinant adeno-associated virus. Hum Gene Ther 1996;7(17):2101-2112.

Carson MR, Travis SM, Welsh MJ. The two nucleotide-binding domains of cystic fibrosis transmembrane conductance regulator (CFTR) have distinct functions in controlling channel activity. J Biol Chem 1995;270(4):1711-1717.

Johnson LG, Boyles SE, Wilson J, Boucher RC. Normalization of raised sodium absorption and raised calcium-mediated chloride secretion by adenovirus-mediated expression of cystic fibrosis transmembrane conductance regulator in primary human cystic fibrosis airway epithelial cells. J Clin Invest 1995;95(3):1377-1382.

Phelps SF, Hauser MA, Cole NM, Rafael JA, Hinkle RT, Faulkner JA, Chamberlain JS. Expression of full-length and truncated dystrophin mini-genes in transgenic mdx mice. Hum Mol Genet 1995;4(8):1251-1258.

Zeiher BG, Eichwald E, Zabner J, Smith JJ, Puga AP, McCray PB, Jr., Capecchi MR, Welsh MJ, Thomas KR. A mouse model for the delta F508 allele of cystic fibrosis. J Clin Invest 1995;96(4):2051-2064.

Boucher RC. Human airway ion transport. Part One Am J Respir Crit Care Med 1994;150(1):271-281.

Flotte TR, Afione SA, Solow R, Drumm ML, Markakis D, Guggino WB, Zeitlin PL, Carter BJ. Expression of the cystic fibrosis transmembrane conductance regulator from a novel adeno-associated virus promoter. J Biol Chem 1993;268(5):3781-3790.

Rich DP, Gregory RJ, Cheng SH, Smith AE, Welsh MJ. Effect of delection mutations on the function of CFTR chloride channels. Receptors Channels 1993;1:221-232.

Blobel CP, Wolfsberg TG, Turck CW, Myles DG, Primakoff P, White JM. A potential fusion peptide and an integrin ligand domain in a protein active in sperm-egg fusion. Nature 1992;356(6366):248-252.

Muzyczka N. Use of adeno-associated virus as a general transduction vector for mammalian cells. Curr Topics Microbiol Immunol 1992;158:97-129.

Rosenfeld MA, Yoshimura K, Trapnell BC, Yoneyama K, Rosenthal ER, Dalemans W, Fukayama M, Bargon J, Stier LE, Stratford-Perricaudet L et al. In vivo transfer of the human cystic fibrosis transmembrane conductance regulator gene to the airway epithelium. Cell 1992;68(1):143-155.

Tilly BC, Winter MC, Ostedgaard LS, O'Riordan C. Smith AE, Welsh MJ. Cyclic AMP-dependent protein kinase activation of cystic fibrosis transmembrane conductance regulator chloride channels in planar lipid bilayers. J Biol Chem 1992;267(14):9470-9473.

Curiel DT, Agarwal S, Wagner E, Cotton M. Adenovirus enhancement of transferrin-polylysine-mediated gene delivery. Proc Natl Acad Sci USA, 1991;88(19):8850-8854.

Hazinski TA, Ladd PA, DeMatteo CA. Localization and induced expression of fusion genes in the rat lung. Am J Respir Cell Mol Biol 1991;4(3):206-209.

Rich DP, Gregory RJ, Anderson MP, Manavalan P, Smith AE, Welsh MJ. Effect of deleting the R domain on CFTR-generated chloride channels. Science 1991;253(5016):205-207.

Rosenfeld MA, Siegfried W, Yoshimura K, Yoneyama K, Fukayama M, Stier LE, Paakko PK, Gilardi P, Stratford-Perricaudet LD, Perricaudet M et al. Adenovirus-mediated transfer of a recombinant alpha 1-antitrypsin gene to the lung epithelium in vivo. Science 1991;252(5004):431-434.

Cheng SH, Gregory RJ, Marshall J, Paul S, Souza DW, White GA, O'Riordan CR, Smith AE. Defective intracellular transport and processing of CFTR is the molecular basis of most cystic fibrosis. Cell 1990;63(4):827-834.

Miller AD. Progress toward human gene therapy. Blood 1990;76(2):271-278.

Wolff JA, Malone RW, Williams P, Chong W, Acsadi G, Jani A, Felgner PL. Direct gene transfer into mouse muscle in vivo. Science 1990;247(4949 Pt 1):1465-1468.

Felgner PL, Ringold GM. Cationic liposome-mediated treansfection. Nature 1989;337(6205):387-388.

Riordan JR, Rommens JM, Kerem B, Alon N, Rozmahel R, Grzelczak Z, Zielenski J, Lok S, Plavsic N, Chou JL et al. Identification of the cystic fibrosis gene: cloning and characterization of complementary DNA. Science 1989;245(4922):1066-1073.

Berkner KL. Development of adenovirus vectors for the expression of heterologous genes. BioTechniques 1988;6(7):616-629.

Wu GY, Wu CH. Receptor-mediated gene delivery and expression in vivo. J Biol Chem 1988;263(29):14621-14624.

Green M, Wold WS, Mackey JK, Rigden P. Analysis of human tonsil and cancer DNAs and RNAs for DNA sequences of group C (serotypes 1, 2, 5 and 6) human adenoviruses. Proc Natl Acad Sci USA 1979;76(12):6606-6610.

Schwartz AR, Togo Y, Hornick RB. Clinical evaluation of live, oral types 1, 2 and 5 adenovirus vaccines. Am Rev Respir Dis 1974;109(2):233-238.

SEQUENCE LISTING

<160> NUMBER OF SEQ ID NOS: 16

<210> SEQ ID NO 1
<211> LENGTH: 4191
<212> TYPE: DNA
<213> ORGANISM: homo sapiens
<220> FEATURE:
<221> NAME/KEY: CDS
<222> LOCATION: (133)...(4191)

<400> SEQUENCE: 1

```
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga cc atg cag agg tcg cct ctg gaa aag gcc agc gtt gtc tcc    171
           Met Gln Arg Ser Pro Leu Glu Lys Ala Ser Val Val Ser
             1               5                  10 aaa ctt ttt ttc agc tgg acc aga cca att ttg agg aaa gga tac aga       219
Lys Leu Phe Phe Ser Trp Thr Arg Pro Ile Leu Arg Lys Gly Tyr Arg
     15                  20                  25 cag cgc ctg gaa ttg tca gac ata tac caa atc cct tct gtt gat tct       267
Gln Arg Leu Glu Leu Ser Asp Ile Tyr Gln Ile Pro Ser Val Asp Ser
 30                  35                  40                  45 gct gac aat cta tct gaa aaa ttg gaa aga gaa tgg gat aga gag ctg       315
Ala Asp Asn Leu Ser Glu Lys Leu Glu Arg Glu Trp Asp Arg Glu Leu
                 50                  55                  60 gct tca aag aaa aat cct aaa ctc att aat gcc ctt cgg cga tgt ttt       363
Ala Ser Lys Lys Asn Pro Lys Leu Ile Asn Ala Leu Arg Arg Cys Phe
```

-continued

```
                    65                      70                      75
ttc tgg aga ttt atg ttc tat gga atc ttt tta tat tta ggg gaa gtc        411
Phe Trp Arg Phe Met Phe Tyr Gly Ile Phe Leu Tyr Leu Gly Glu Val
            80                      85                      90 acc aaa gca gta cag cct ctc tta ctg gga aga atc ata gct tcc tat        459
Thr Lys Ala Val Gln Pro Leu Leu Gly Arg Ile Ile Ala Ser Tyr
        95                      100                     105 gac ccg gat aac aag gag gaa cgc tct atc gcg att tat cta ggc ata        507
Asp Pro Asp Asn Lys Glu Glu Arg Ser Ile Ala Ile Tyr Leu Gly Ile
110                     115                     120                     125 ggc tta tgc ctt ctc ttt att gtg agg aca ctg ctc cta cac cca gcc        555
Gly Leu Cys Leu Leu Phe Ile Val Arg Thr Leu Leu Leu His Pro Ala
                    130                     135                     140 att ttt ggc ctt cat cac att gga atg cag atg aga ata gct atg ttt        603
Ile Phe Gly Leu His His Ile Gly Met Gln Met Arg Ile Ala Met Phe
                145                     150                     155 agt ttg att tat aag aag act tta aag ctg tca agc cgt gtt cta gat        651
Ser Leu Ile Tyr Lys Lys Thr Leu Lys Leu Ser Ser Arg Val Leu Asp
                160                     165                     170 aaa ata agt att gga caa ctt gtt agt ctc ctt tcc aac aac ctg aac        699
Lys Ile Ser Ile Gly Gln Leu Val Ser Leu Leu Ser Asn Asn Leu Asn
            175                     180                     185 aaa ttt gat gaa gga ctt gca ttg gca cat ttc gtg tgg atc gct cct        747
Lys Phe Asp Glu Gly Leu Ala Leu Ala His Phe Val Trp Ile Ala Pro
190                     195                     200                     205 ttg caa gtg gca ctc ctc atg ggg cta atc tgg gag ttg tta cag gcg        795
Leu Gln Val Ala Leu Leu Met Gly Leu Ile Trp Glu Leu Leu Gln Ala
                    210                     215                     220 tct gcc ttc tgt gga ctt ggt ttc ctg ata gtc ctt gcc ctt ttt cag        843
Ser Ala Phe Cys Gly Leu Gly Phe Leu Ile Val Leu Ala Leu Phe Gln
                225                     230                     235 gct ggg cta ggg aga atg atg atg aag tac aga gat cag aga gct ggg        891
Ala Gly Leu Gly Arg Met Met Met Lys Tyr Arg Asp Gln Arg Ala Gly
                    240                     245                     250 aag atc agt gaa aga ctt gtg att acc tca gaa atg att gaa aat atc        939
Lys Ile Ser Glu Arg Leu Val Ile Thr Ser Glu Met Ile Glu Asn Ile
            255                     260                     265 caa tct gtt aag gca tac tgc tgg gaa gaa gca atg gaa aaa atg att        987
Gln Ser Val Lys Ala Tyr Cys Trp Glu Glu Ala Met Glu Lys Met Ile
270                     275                     280                     285 gaa aac tta aga caa aca gaa ctg aaa ctg act cgg aag gca gcc tat       1035
Glu Asn Leu Arg Gln Thr Glu Leu Lys Leu Thr Arg Lys Ala Ala Tyr
                    290                     295                     300 gtg aga tac ttc aat agc tca gcc ttc ttc tca ggg ttc ttt gtg       1083
Val Arg Tyr Phe Asn Ser Ser Ala Phe Phe Phe Ser Gly Phe Phe Val
                305                     310                     315 gtg ttt tta tct gtg ctt ccc tat gca cta atc aaa gga atc atc ctc       1131
Val Phe Leu Ser Val Leu Pro Tyr Ala Leu Ile Lys Gly Ile Ile Leu
                    320                     325                     330 cgg aaa ata ttc acc acc atc tca ttc tgc att gtt ctg cgc atg gcg       1179
Arg Lys Ile Phe Thr Thr Ile Ser Phe Cys Ile Val Leu Arg Met Ala
                335                     340                     345 gtc act cgg caa ttt ccc tgg gct gta caa aca tgg tat gac tct ctt       1227
Val Thr Arg Gln Phe Pro Trp Ala Val Gln Thr Trp Tyr Asp Ser Leu
350                     355                     360                     365 gga gca ata aac aaa ata cag gat ttc tta caa aag caa gaa tat aag       1275
Gly Ala Ile Asn Lys Ile Gln Asp Phe Leu Gln Lys Gln Glu Tyr Lys
                    370                     375                     380 aca ttg gaa tat aac tta acg act aca gaa gta gtg atg gag aat gta       1323
```

```
                Thr Leu Glu Tyr Asn Leu Thr Thr Thr Glu Val Val Met Glu Asn Val
                            385                 390                 395 aca gcc ttc tgg gag gag gga ttt ggg gaa tta ttt gag aaa gca aaa          1371
Thr Ala Phe Trp Glu Glu Gly Phe Gly Glu Leu Phe Glu Lys Ala Lys
            400                 405                 410 caa aac aat aac aat aga aaa act tct aat ggt gat gac agc ctc ttc          1419
Gln Asn Asn Asn Asn Arg Lys Thr Ser Asn Gly Asp Asp Ser Leu Phe
            415                 420                 425 ttc agt aat ttc tca ctt ctt ggt act cct gtc ctg aaa gat att aat          1467
Phe Ser Asn Phe Ser Leu Leu Gly Thr Pro Val Leu Lys Asp Ile Asn
430                 435                 440                 445 ttc aag ata gaa aga gga cag ttg ttg gcg gtt gct gga tcc act gga          1515
Phe Lys Ile Glu Arg Gly Gln Leu Leu Ala Val Ala Gly Ser Thr Gly
            450                 455                 460 gca ggc aag act tca ctt cta atg atg att atg gga gaa ctg gag cct          1563
Ala Gly Lys Thr Ser Leu Leu Met Met Ile Met Gly Glu Leu Glu Pro
            465                 470                 475 tca gag ggt aaa att aag cac agt gga aga att tca ttc tgt tct cag          1611
Ser Glu Gly Lys Ile Lys His Ser Gly Arg Ile Ser Phe Cys Ser Gln
            480                 485                 490 ttt tcc tgg att atg cct ggc acc att aaa gaa aat atc atc ttt ggt          1659
Phe Ser Trp Ile Met Pro Gly Thr Ile Lys Glu Asn Ile Ile Phe Gly
            495                 500                 505 gtt tcc tat gat gaa tat aga tac aga agc gtc atc aaa gca tgc caa          1707
Val Ser Tyr Asp Glu Tyr Arg Tyr Arg Ser Val Ile Lys Ala Cys Gln
510                 515                 520                 525 cta gaa gag gac atc tcc aag ttt gca gag aaa gac aat ata gtt ctt          1755
Leu Glu Glu Asp Ile Ser Lys Phe Ala Glu Lys Asp Asn Ile Val Leu
            530                 535                 540 gga gaa ggt gga atc aca ctg agt gga ggt caa cga gca aga att tct          1803
Gly Glu Gly Gly Ile Thr Leu Ser Gly Gly Gln Arg Ala Arg Ile Ser
            545                 550                 555 tta gca aga gca gta tac aaa gat gct gat ttg tat tta tta gac tct          1851
Leu Ala Arg Ala Val Tyr Lys Asp Ala Asp Leu Tyr Leu Leu Asp Ser
            560                 565                 570 cct ttt gga tac cta gat gtt tta aca gaa aaa gaa ata ttt gaa agc          1899
Pro Phe Gly Tyr Leu Asp Val Leu Thr Glu Lys Glu Ile Phe Glu Ser
            575                 580                 585 tgt gtc tgt aaa ctg atg gct aac aaa act agg att ttg gtc act tct          1947
Cys Val Cys Lys Leu Met Ala Asn Lys Thr Arg Ile Leu Val Thr Ser
590                 595                 600                 605 aaa atg gaa cat tta aag aaa gct gac aaa ata tta att ttg cat gaa          1995
Lys Met Glu His Leu Lys Lys Ala Asp Lys Ile Leu Ile Leu His Glu
            610                 615                 620 ggt agc agc tat ttt tat ggg aca ttt tca gaa ctc caa aat cta cag          2043
Gly Ser Ser Tyr Phe Tyr Gly Thr Phe Ser Glu Leu Gln Asn Leu Gln
            625                 630                 635 cca gac ttt agc tca aaa ctc atg gga tgt gat tct ttc gac caa ttt          2091
Pro Asp Phe Ser Ser Lys Leu Met Gly Cys Asp Ser Phe Asp Gln Phe
            640                 645                 650 agt gca gaa aga aga aat tca atc cta act gag acc tta cac cgt ttc          2139
Ser Ala Glu Arg Arg Asn Ser Ile Leu Thr Glu Thr Leu His Arg Phe
            655                 660                 665 tca tta gaa gga gat gct cct gtc tcc tgg aca gaa aca aaa aaa caa          2187
Ser Leu Glu Gly Asp Ala Pro Val Ser Trp Thr Glu Thr Lys Lys Gln
670                 675                 680                 685 tct ttt aaa cag act gga gag ttt ggg gaa aaa agg aag aat tct att          2235
Ser Phe Lys Gln Thr Gly Glu Phe Gly Glu Lys Arg Lys Asn Ser Ile
            690                 695                 700
```

```
ctc aat cca atc aac tct gat atg gag agc ata cca gca gtg act aca    2283
Leu Asn Pro Ile Asn Ser Asp Met Glu Ser Ile Pro Ala Val Thr Thr
        705                 710                 715 tgg aac aca tac ctt cga tat att act gtc cac aag agc tta att ttt    2331
Trp Asn Thr Tyr Leu Arg Tyr Ile Thr Val His Lys Ser Leu Ile Phe
    720                 725                 730 gtg cta att tgg tgc tta gta att ttt ctg gca gag gtg gct gct tct    2379
Val Leu Ile Trp Cys Leu Val Ile Phe Leu Ala Glu Val Ala Ala Ser
735                 740                 745 ttg gtt gtg ctg tgg ctc ctt gga aac act cct ctt caa gac aaa ggg    2427
Leu Val Val Leu Trp Leu Leu Gly Asn Thr Pro Leu Gln Asp Lys Gly
750                 755                 760                 765 aat agt act cat agt aga aat aac agc tat gca gtg att atc acc agc    2475
Asn Ser Thr His Ser Arg Asn Asn Ser Tyr Ala Val Ile Ile Thr Ser
            770                 775                 780 acc agt tcg tat tat gtg ttt tac att tac gtg gga gta gcc gac act    2523
Thr Ser Ser Tyr Tyr Val Phe Tyr Ile Tyr Val Gly Val Ala Asp Thr
                785                 790                 795 ttg ctt gct atg gga ttc ttc aga ggt cta cca ctg gtg cat act cta    2571
Leu Leu Ala Met Gly Phe Phe Arg Gly Leu Pro Leu Val His Thr Leu
                    800                 805                 810 atc aca gtg tcg aaa att tta cac cac aaa atg tta cat tct gtt ctt    2619
Ile Thr Val Ser Lys Ile Leu His His Lys Met Leu His Ser Val Leu
                815                 820                 825 caa gca cct atg tca acc ctc aac acg ttg aaa gca ggt ggg att ctt    2667
Gln Ala Pro Met Ser Thr Leu Asn Thr Leu Lys Ala Gly Gly Ile Leu
830                 835                 840                 845 aat aga ttc tcc aaa gat ata gca att ttg gat gac ctt ctg cct ctt    2715
Asn Arg Phe Ser Lys Asp Ile Ala Ile Leu Asp Asp Leu Leu Pro Leu
                    850                 855                 860 acc ata ttt gac ttc atc cag ttg tta tta att gtg att gga gct ata    2763
Thr Ile Phe Asp Phe Ile Gln Leu Leu Leu Ile Val Ile Gly Ala Ile
                865                 870                 875 gca gtt gtc gca gtt tta caa ccc tac atc ttt gtt gca aca gtg cca    2811
Ala Val Val Ala Val Leu Gln Pro Tyr Ile Phe Val Ala Thr Val Pro
            880                 885                 890 gtg ata gtg gct ttt att atg ttg aga gca tat ttc ctc caa acc tca    2859
Val Ile Val Ala Phe Ile Met Leu Arg Ala Tyr Phe Leu Gln Thr Ser
        895                 900                 905 cag caa ctc aaa caa ctg gaa tct gaa ggc agg agt cca att ttc act    2907
Gln Gln Leu Lys Gln Leu Glu Ser Glu Gly Arg Ser Pro Ile Phe Thr
910                 915                 920                 925 cat ctt gtt aca agc tta aaa gga cta tgg aca ctt cgt gcc ttc gga    2955
His Leu Val Thr Ser Leu Lys Gly Leu Trp Thr Leu Arg Ala Phe Gly
                    930                 935                 940 cgg cag cct tac ttt gaa act ctg ttc cac aaa gct ctg aat tta cat    3003
Arg Gln Pro Tyr Phe Glu Thr Leu Phe His Lys Ala Leu Asn Leu His
                945                 950                 955 act gcc aac tgg ttc ttg tac ctg tca aca ctg cgc tgg ttc caa atg    3051
Thr Ala Asn Trp Phe Leu Tyr Leu Ser Thr Leu Arg Trp Phe Gln Met
            960                 965                 970 aga ata gaa atg att ttt gtc atc ttc ttc att gct gtt acc ttc att    3099
Arg Ile Glu Met Ile Phe Val Ile Phe Phe Ile Ala Val Thr Phe Ile
        975                 980                 985 tcc att tta aca aca gga gaa gga gaa gga aga gtt ggt att atc ctg    3147
Ser Ile Leu Thr Thr Gly Glu Gly Glu Gly Arg Val Gly Ile Ile Leu
    990                 995                 1000                1005 act tta gcc atg aat atc atg agt aca ttg cag tgg gct gta aac tcc    3195
Thr Leu Ala Met Asn Ile Met Ser Thr Leu Gln Trp Ala Val Asn Ser
                1010                1015                1020
```

| | |
|---|---|
| agc ata gat gtg gat agc ttg atg cga tct gtg agc cga gtc ttt aag<br>Ser Ile Asp Val Asp Ser Leu Met Arg Ser Val Ser Arg Val Phe Lys<br>        1025                1030               1035 | 3243 |
| ttc att gac atg cca aca gaa ggt aaa cct acc aag tca acc aaa cca<br>Phe Ile Asp Met Pro Thr Glu Gly Lys Pro Thr Lys Ser Thr Lys Pro<br>1040                 1045                1050 | 3291 |
| tac aag aat ggc caa ctc tcg aaa gtt atg att att gag aat tca cac<br>Tyr Lys Asn Gly Gln Leu Ser Lys Val Met Ile Ile Glu Asn Ser His<br>        1055                1060               1065 | 3339 |
| gtg aag aaa gat gac atc tgg ccc tca ggg ggc caa atg act gtc aaa<br>Val Lys Lys Asp Asp Ile Trp Pro Ser Gly Gly Gln Met Thr Val Lys<br>1070                 1075                1080               1085 | 3387 |
| gat ctc aca gca aaa tac aca gaa ggt gga aat gcc ata tta gag aac<br>Asp Leu Thr Ala Lys Tyr Thr Glu Gly Gly Asn Ala Ile Leu Glu Asn<br>              1090                1095               1100 | 3435 |
| att tcc ttc tca ata agt cct ggc cag agg gtg ggc ctc ttg gga aga<br>Ile Ser Phe Ser Ile Ser Pro Gly Gln Arg Val Gly Leu Leu Gly Arg<br>        1105                1110               1115 | 3483 |
| act gga tca ggg aag agt act ttg tta tca gct ttt tga aga cta ctg<br>Thr Gly Ser Gly Lys Ser Thr Leu Leu Ser Ala Phe Leu Arg Leu Leu<br>           1120                1125               1130 | 3531 |
| aac act gaa gga gaa atc cag atc gat ggt gtg tct tgg gat tca ata<br>Asn Thr Glu Gly Glu Ile Gln Ile Asp Gly Val Ser Trp Asp Ser Ile<br>        1135                1140               1145 | 3579 |
| act ttg caa cag tgg agg aaa gcc ttt gga gtg ata cca cag aaa gta<br>Thr Leu Gln Gln Trp Arg Lys Ala Phe Gly Val Ile Pro Gln Lys Val<br>1150                 1155                1160               1165 | 3627 |
| ttt att ttt tct gga aca ttt aga aaa aac ttg gat ccc tat gaa cag<br>Phe Ile Phe Ser Gly Thr Phe Arg Lys Asn Leu Asp Pro Tyr Glu Gln<br>              1170                1175               1180 | 3675 |
| tgg agt gat caa gaa ata tgg aaa gtt gca gat gag gtt ggg ctc aga<br>Trp Ser Asp Gln Glu Ile Trp Lys Val Ala Asp Glu Val Gly Leu Arg<br>                1185                1190               1195 | 3723 |
| tct gtg ata gaa cag ttt cct ggg aag ctt gac ttt gtc ctt gtg gat<br>Ser Val Ile Glu Gln Phe Pro Gly Lys Leu Asp Phe Val Leu Val Asp<br>            1200                1205               1210 | 3771 |
| ggg ggc tgt gtc cta agc cat ggc cac aag cag ttg atg tgc ttg gct<br>Gly Gly Cys Val Leu Ser His Gly His Lys Gln Leu Met Cys Leu Ala<br>        1215                1220               1225 | 3819 |
| aga tct gtt ctc agt aag gcg aag atc ttg ctg ctt gat gaa ccc agt<br>Arg Ser Val Leu Ser Lys Ala Lys Ile Leu Leu Leu Asp Glu Pro Ser<br>1230                 1235                1240               1245 | 3867 |
| gct cat ttg gat cca gta aca tac caa ata att aga aga act cta aaa<br>Ala His Leu Asp Pro Val Thr Tyr Gln Ile Ile Arg Arg Thr Leu Lys<br>              1250                1255               1260 | 3915 |
| caa gca ttt gct gat tgc aca gta att ctc tgt gaa cac agg ata gaa<br>Gln Ala Phe Ala Asp Cys Thr Val Ile Leu Cys Glu His Arg Ile Glu<br>            1265                1270               1275 | 3963 |
| gca atg ctg gaa tgc caa caa ttt ttg gtc ata gaa gag aac aaa gtg<br>Ala Met Leu Glu Cys Gln Gln Phe Leu Val Ile Glu Glu Asn Lys Val<br>                1280                1285               1290 | 4011 |
| cgg cag tac gat tcc atc cag aaa ctg ctg aac gag agg agc ctc ttc<br>Arg Gln Tyr Asp Ser Ile Gln Lys Leu Leu Asn Glu Arg Ser Leu Phe<br>            1295                1300               1305 | 4059 |
| cgg caa gcc atc agc ccc tcc gac agg gtg aag ctc ttt ccc cac cgg<br>Arg Gln Ala Ile Ser Pro Ser Asp Arg Val Lys Leu Phe Pro His Arg<br>1310                 1315                1320               1325 | 4107 |
| aac tca agc aag tgc aag tct aag ccc cag att gct gct ctg aaa gag<br>Asn Ser Ser Lys Cys Lys Ser Lys Pro Gln Ile Ala Ala Leu Lys Glu | 4155 |

-continued

```
                   1330              1335              1340
gag aca gaa gaa gag gtg caa gat aca agg ctt tag                    4191
Glu Thr Glu Glu Glu Val Gln Asp Thr Arg Leu *
        1345                      1350

<210> SEQ ID NO 2
<211> LENGTH: 4419
<212> TYPE: DNA
<213> ORGANISM: homo sapiens
<220> FEATURE:
<221> NAME/KEY: CDS
<222> LOCATION: (133)...(4419)

<400> SEQUENCE: 2
aattggaagc aaatgacatc acagcaggtc agagaaaaag ggttgagcgg caggcaccca    60
gagtagtagg tctttggcat taggagcttg agcccagacg gccctagcag ggaccccagc   120
gcccgagaga cc atg cag agg tcg cct ctg gaa aag gcc agc gtt gtc tcc   171
             Met Gln Arg Ser Pro Leu Glu Lys Ala Ser Val Val Ser
              1               5                  10 aaa ctt ttt ttc agc tgg acc aga cca att ttg agg aaa gga tac aga     219
Lys Leu Phe Phe Ser Trp Thr Arg Pro Ile Leu Arg Lys Gly Tyr Arg
 15                  20                  25 cag cgc ctg gaa ttg tca gac ata tac caa atc cct tct gtt gat tct     267
Gln Arg Leu Glu Leu Ser Asp Ile Tyr Gln Ile Pro Ser Val Asp Ser
 30                  35                  40                  45 gct gac aat cta tct gaa aaa ttg gaa aga gaa tgg gat aga gag ctg     315
Ala Asp Asn Leu Ser Glu Lys Leu Glu Arg Glu Trp Asp Arg Glu Leu
                 50                  55                  60 gct tca aag aaa aat cct aaa ctc att aat gcc ctt cgg cga tgt ttt     363
Ala Ser Lys Lys Asn Pro Lys Leu Ile Asn Ala Leu Arg Arg Cys Phe
             65                  70                  75 ttc tgg aga ttt atg ttc tat gga atc ttt tta tat tta ggg gaa gtc     411
Phe Trp Arg Phe Met Phe Tyr Gly Ile Phe Leu Tyr Leu Gly Glu Val
         80                  85                  90 acc aaa gca gta cag cct ctc tta ctg gga aga atc ata gct tcc tat     459
Thr Lys Ala Val Gln Pro Leu Leu Leu Gly Arg Ile Ile Ala Ser Tyr
     95                 100                 105 gac ccg gat aac aag gag gaa cgc tct atc gcg att tat cta ggc ata     507
Asp Pro Asp Asn Lys Glu Glu Arg Ser Ile Ala Ile Tyr Leu Gly Ile
110                 115                 120                 125 ggc tta tgc ctt ctc ttt att gtg agg aca ctg ctc cta cac cca gcc     555
Gly Leu Cys Leu Leu Phe Ile Val Arg Thr Leu Leu Leu His Pro Ala
                130                 135                 140 att ttt ggc ctt cat cac att gga atg cag atg aga ata gct atg ttt     603
Ile Phe Gly Leu His His Ile Gly Met Gln Met Arg Ile Ala Met Phe
            145                 150                 155 agt ttg att tat aag aag act tta aag ctg tca agc cgt gtt cta gat     651
Ser Leu Ile Tyr Lys Lys Thr Leu Lys Leu Ser Ser Arg Val Leu Asp
        160                 165                 170 aaa ata agt att gga caa ctt gtt agt ctc ctt tcc aac aac ctg aac     699
Lys Ile Ser Ile Gly Gln Leu Val Ser Leu Leu Ser Asn Asn Leu Asn
    175                 180                 185 aaa ttt gat gaa gga ctt gca ttg gca cat ttc gtg tgg atc gct cct     747
Lys Phe Asp Glu Gly Leu Ala Leu Ala His Phe Val Trp Ile Ala Pro
190                 195                 200                 205 ttg caa gtg gca ctc ctc atg ggg cta atc tgg gag ttg tta cag gcg     795
Leu Gln Val Ala Leu Leu Met Gly Leu Ile Trp Glu Leu Leu Gln Ala
                210                 215                 220 tct gcc ttc tgt gga ctt ggt ttc ctg ata gtc ctt gcc ctt ttt cag     843
Ser Ala Phe Cys Gly Leu Gly Phe Leu Ile Val Leu Ala Leu Phe Gln
```

-continued

```
                     225                 230                 235
gct ggg cta ggg aga atg atg atg aag tac aga gat cag aga gct ggg    891
Ala Gly Leu Gly Arg Met Met Met Lys Tyr Arg Asp Gln Arg Ala Gly
            240                 245                 250 aag atc agt gaa aga ctt gtg att acc tca gaa atg att gaa aat atc    939
Lys Ile Ser Glu Arg Leu Val Ile Thr Ser Glu Met Ile Glu Asn Ile
        255                 260                 265 caa tct gtt aag gca tac tgc tgg gaa gaa gca atg gaa aaa atg att    987
Gln Ser Val Lys Ala Tyr Cys Trp Glu Glu Ala Met Glu Lys Met Ile
270                 275                 280                 285 gaa aac tta aga caa aca gaa ctg aaa ctg act cgg aag gca gcc tat   1035
Glu Asn Leu Arg Gln Thr Glu Leu Lys Leu Thr Arg Lys Ala Ala Tyr
                290                 295                 300 gtg aga tac ttc aat agc tca gcc ttc ttc ttc tca ggg ttc ttt gtg   1083
Val Arg Tyr Phe Asn Ser Ser Ala Phe Phe Phe Ser Gly Phe Phe Val
            305                 310                 315 gtg ttt tta tct gtg ctt ccc tat gca cta atc aaa gga atc atc ctc   1131
Val Phe Leu Ser Val Leu Pro Tyr Ala Leu Ile Lys Gly Ile Ile Leu
        320                 325                 330 cgg aaa ata ttc acc acc atc tca ttc tgc att gtt ctg cgc atg gcg   1179
Arg Lys Ile Phe Thr Thr Ile Ser Phe Cys Ile Val Leu Arg Met Ala
335                 340                 345 gtc act cgg caa ttt ccc tgg gct gta caa aca tgg tat gac tct ctt   1227
Val Thr Arg Gln Phe Pro Trp Ala Val Gln Thr Trp Tyr Asp Ser Leu
350                 355                 360                 365 gga gca ata aac aaa ata cag gat ttc tta caa aag caa gaa tat aag   1275
Gly Ala Ile Asn Lys Ile Gln Asp Phe Leu Gln Lys Gln Glu Tyr Lys
                370                 375                 380 aca ttg gaa tat aac tta acg act aca gaa gta gtg atg gag aat gta   1323
Thr Leu Glu Tyr Asn Leu Thr Thr Thr Glu Val Val Met Glu Asn Val
            385                 390                 395 aca gcc ttc tgg gag gag gga ttt ggg gaa tta ttt gag aaa gca aaa   1371
Thr Ala Phe Trp Glu Glu Gly Phe Gly Glu Leu Phe Glu Lys Ala Lys
        400                 405                 410 caa aac aat aac aat aga aaa act tct aat ggt gat gac agc ctc ttc   1419
Gln Asn Asn Asn Asn Arg Lys Thr Ser Asn Gly Asp Asp Ser Leu Phe
415                 420                 425 ttc agt aat ttc tca ctt ctt ggt act cct gtc ctg aaa gat att aat   1467
Phe Ser Asn Phe Ser Leu Leu Gly Thr Pro Val Leu Lys Asp Ile Asn
430                 435                 440                 445 ttc aag ata gaa aga gga cag ttg ttg gcg gtt gct gga tcc act gga   1515
Phe Lys Ile Glu Arg Gly Gln Leu Leu Ala Val Ala Gly Ser Thr Gly
                450                 455                 460 gca ggc aag act tca ctt cta atg atg att atg gga gaa ctg gag cct   1563
Ala Gly Lys Thr Ser Leu Leu Met Met Ile Met Gly Glu Leu Glu Pro
            465                 470                 475 tca gag ggt aaa att aag cac agt gga aga att tca ttc tgt tct cag   1611
Ser Glu Gly Lys Ile Lys His Ser Gly Arg Ile Ser Phe Cys Ser Gln
        480                 485                 490 ttt tcc tgg att atg cct ggc acc att aaa gaa aat atc atc ttt ggt   1659
Phe Ser Trp Ile Met Pro Gly Thr Ile Lys Glu Asn Ile Ile Phe Gly
495                 500                 505 gtt tcc tat gat gaa tat aga tac aga agc gtc atc aaa gca tgc caa   1707
Val Ser Tyr Asp Glu Tyr Arg Tyr Arg Ser Val Ile Lys Ala Cys Gln
510                 515                 520                 525 cta gaa gag gac atc tcc aag ttt gca gag aaa gac aat ata gtt ctt   1755
Leu Glu Glu Asp Ile Ser Lys Phe Ala Glu Lys Asp Asn Ile Val Leu
                530                 535                 540 gga gaa ggt gga atc aca ctg agt gga ggt caa cga gca aga att tct   1803
```

```
Gly Glu Gly Gly Ile Thr Leu Ser Gly Gly Gln Arg Ala Arg Ile Ser
            545                 550                 555 tta gca aga gca gta tac aaa gat gct gat ttg tat tta tta gac tct    1851
Leu Ala Arg Ala Val Tyr Lys Asp Ala Asp Leu Tyr Leu Leu Asp Ser
        560                 565                 570 cct ttt gga tac cta gat gtt tta aca gaa aaa gaa ata ttt gaa agc    1899
Pro Phe Gly Tyr Leu Asp Val Leu Thr Glu Lys Glu Ile Phe Glu Ser
575                 580                 585 tgt gtc tgt aaa ctg atg gct aac aaa act agg att ttg gtc act tct    1947
Cys Val Cys Lys Leu Met Ala Asn Lys Thr Arg Ile Leu Val Thr Ser
590                 595                 600                 605 aaa atg gaa cat tta aag aaa gct gac aaa ata tta att ttg cat gaa    1995
Lys Met Glu His Leu Lys Lys Ala Asp Lys Ile Leu Ile Leu His Glu
            610                 615                 620 ggt agc agc tat ttt tat ggg aca ttt tca gaa ctc caa aat cta cag    2043
Gly Ser Ser Tyr Phe Tyr Gly Thr Phe Ser Glu Leu Gln Asn Leu Gln
        625                 630                 635 cca gac ttt agc tca aaa ctc atg gga tgt gat tct ttc gac caa ttt    2091
Pro Asp Phe Ser Ser Lys Leu Met Gly Cys Asp Ser Phe Asp Gln Phe
        640                 645                 650 agt gca gaa aga aga aat tca atc cta act gag acc tta cac cgt ttc    2139
Ser Ala Glu Arg Arg Asn Ser Ile Leu Thr Glu Thr Leu His Arg Phe
655                 660                 665 tca tta gaa gga gat gct cct gtc tcc tgg aca gaa aca aaa aaa caa    2187
Ser Leu Glu Gly Asp Ala Pro Val Ser Trp Thr Glu Thr Lys Lys Gln
670                 675                 680                 685 tct ttt aaa cag act gga gag ttt ggg gaa aaa agg aag aat tct att    2235
Ser Phe Lys Gln Thr Gly Glu Phe Gly Glu Lys Arg Lys Asn Ser Ile
            690                 695                 700 ctc aat cca atc aac tct acg ctt cag gca cga agg agg cag tct gtc    2283
Leu Asn Pro Ile Asn Ser Thr Leu Gln Ala Arg Arg Arg Gln Ser Val
        705                 710                 715 ctg aac ctg atg aca cac tca gtt aac caa ggt cag aac att cac cga    2331
Leu Asn Leu Met Thr His Ser Val Asn Gln Gly Gln Asn Ile His Arg
        720                 725                 730 aag aca aca gca tcc aca cga aaa gtg tca ctg gcc cct cag gca aac    2379
Lys Thr Thr Ala Ser Thr Arg Lys Val Ser Leu Ala Pro Gln Ala Asn
735                 740                 745 ttg act gaa ctg gat ata tat tca aga agg tta tct caa gaa act ggc    2427
Leu Thr Glu Leu Asp Ile Tyr Ser Arg Arg Leu Ser Gln Glu Thr Gly
750                 755                 760                 765 ttg gaa ata agt gaa gaa att aac gaa gaa gac tta aag gag tgc ttt    2475
Leu Glu Ile Ser Glu Glu Ile Asn Glu Glu Asp Leu Lys Glu Cys Phe
            770                 775                 780 ttt gat gat atg gag agc ata cca gca gtg act aca tgg aac aca tac    2523
Phe Asp Asp Met Glu Ser Ile Pro Ala Val Thr Thr Trp Asn Thr Tyr
        785                 790                 795 ctt cga tat att act gtc cac aag agc tta att ttt gtg cta att tgg    2571
Leu Arg Tyr Ile Thr Val His Lys Ser Leu Ile Phe Val Leu Ile Trp
        800                 805                 810 tgc tta gta att ttt ctg gca gag gtg gct gct tct ttg gtt gtg ctg    2619
Cys Leu Val Ile Phe Leu Ala Glu Val Ala Ala Ser Leu Val Val Leu
815                 820                 825 tgg ctc ctt gga aac act cct ctt caa gac aaa ggg aat agt act cat    2667
Trp Leu Leu Gly Asn Thr Pro Leu Gln Asp Lys Gly Asn Ser Thr His
830                 835                 840                 845 agt aga aat aac agc tat gca gtg att atc acc agc acc agt tcg tat    2715
Ser Arg Asn Asn Ser Tyr Ala Val Ile Ile Thr Ser Thr Ser Ser Tyr
            850                 855                 860
```

```
tat gtg ttt tac att tac gtg gga gta gcc gac act ttg ctt gct atg    2763
Tyr Val Phe Tyr Ile Tyr Val Gly Val Ala Asp Thr Leu Leu Ala Met
        865                 870                 875 gga ttc ttc aga ggt cta cca ctg gtg cat act cta atc aca gtg tcg    2811
Gly Phe Phe Arg Gly Leu Pro Leu Val His Thr Leu Ile Thr Val Ser
        880                 885                 890 aaa att tta cac cac aaa atg tta cat tct gtt ctt caa gca cct atg    2859
Lys Ile Leu His His Lys Met Leu His Ser Val Leu Gln Ala Pro Met
        895                 900                 905 tca acc ctc aac acg ttg aaa gca ggt ggg att ctt aat aga ttc tcc    2907
Ser Thr Leu Asn Thr Leu Lys Ala Gly Gly Ile Leu Asn Arg Phe Ser
910                 915                 920                 925 aaa gat ata gca att ttg gat gac ctt ctg cct ctt acc ata ttt gac    2955
Lys Asp Ile Ala Ile Leu Asp Asp Leu Leu Pro Leu Thr Ile Phe Asp
                930                 935                 940 ttc atc cag ttg tta tta att gtg att gga gct ata gca gtt gtc gca    3003
Phe Ile Gln Leu Leu Leu Ile Val Ile Gly Ala Ile Ala Val Val Ala
                945                 950                 955 gtt tta caa ccc tac atc ttt gtt gca aca gtg cca gtg ata gtg gct    3051
Val Leu Gln Pro Tyr Ile Phe Val Ala Thr Val Pro Val Ile Val Ala
                960                 965                 970 ttt att atg ttg aga gca tat ttc ctc caa acc tca cag caa ctc aaa    3099
Phe Ile Met Leu Arg Ala Tyr Phe Leu Gln Thr Ser Gln Gln Leu Lys
        975                 980                 985 caa ctg gaa tct gaa ggc agg agt cca att ttc act cat ctt gtt aca    3147
Gln Leu Glu Ser Glu Gly Arg Ser Pro Ile Phe Thr His Leu Val Thr
 990                 995                1000                1005 agc tta aaa gga cta tgg aca ctt cgt gcc ttc gga cgg cag cct tac    3195
Ser Leu Lys Gly Leu Trp Thr Leu Arg Ala Phe Gly Arg Gln Pro Tyr
                1010                1015                1020 ttt gaa act ctg ttc cac aaa gct ctg aat tta cat act gcc aac tgg    3243
Phe Glu Thr Leu Phe His Lys Ala Leu Asn Leu His Thr Ala Asn Trp
                1025                1030                1035 ttc ttg tac ctg tca aca ctg cgc tgg ttc caa atg aga ata gaa atg    3291
Phe Leu Tyr Leu Ser Thr Leu Arg Trp Phe Gln Met Arg Ile Glu Met
                1040                1045                1050 att ttt gtc atc ttc ttc att gct gtt acc ttc att tcc att tta aca    3339
Ile Phe Val Ile Phe Phe Ile Ala Val Thr Phe Ile Ser Ile Leu Thr
        1055                1060                1065 aca gga gaa gga gaa gga aga gtt ggt att atc ctg act tta gcc atg    3387
Thr Gly Glu Gly Glu Gly Arg Val Gly Ile Ile Leu Thr Leu Ala Met
1070                1075                1080                1085 aat atc atg agt aca ttg cag tgg gct gta aac tcc agc ata gat gtg    3435
Asn Ile Met Ser Thr Leu Gln Trp Ala Val Asn Ser Ser Ile Asp Val
                1090                1095                1100 gat agc ttg atg cga tct gtg agc cga gtc ttt aag ttc att gac atg    3483
Asp Ser Leu Met Arg Ser Val Ser Arg Val Phe Lys Phe Ile Asp Met
                1105                1110                1115 cca aca gaa ggt aaa cct acc aag tca acc aaa cca tac aag aat ggc    3531
Pro Thr Glu Gly Lys Pro Thr Lys Ser Thr Lys Pro Tyr Lys Asn Gly
                1120                1125                1130 caa ctc tcg aaa gtt atg att att gag aat tca cac gtg aag aaa gat    3579
Gln Leu Ser Lys Val Met Ile Ile Glu Asn Ser His Val Lys Lys Asp
        1135                1140                1145 gac atc tgg ccc tca ggg ggc caa atg act gtc aaa gat ctc aca gca    3627
Asp Ile Trp Pro Ser Gly Gly Gln Met Thr Val Lys Asp Leu Thr Ala
1150                1155                1160                1165 aaa tac aca gaa ggt gga aat gcc ata tta gag aac att tcc ttc tca    3675
Lys Tyr Thr Glu Gly Gly Asn Ala Ile Leu Glu Asn Ile Ser Phe Ser
                1170                1175                1180
```

```
ata agt cct ggc cag agg gtg ggc ctc ttg gga aga act gga tca ggg    3723
Ile Ser Pro Gly Gln Arg Val Gly Leu Leu Gly Arg Thr Gly Ser Gly
        1185                1190                1195 aag agt act ttg tta tca gct ttt ttg aga cta ctg aac act gaa gga    3771
Lys Ser Thr Leu Leu Ser Ala Phe Leu Arg Leu Leu Asn Thr Glu Gly
        1200                1205                1210 gaa atc cag atc gat ggt gtg tct tgg gat tca ata act ttg caa cag    3819
Glu Ile Gln Ile Asp Gly Val Ser Trp Asp Ser Ile Thr Leu Gln Gln
        1215                1220                1225 tgg agg aaa gcc ttt gga gtg ata cca cag aaa gta ttt att ttt tct    3867
Trp Arg Lys Ala Phe Gly Val Ile Pro Gln Lys Val Phe Ile Phe Ser
1230                1235                1240                1245 gga aca ttt aga aaa aac ttg gat ccc tat gaa cag tgg agt gat caa    3915
Gly Thr Phe Arg Lys Asn Leu Asp Pro Tyr Glu Gln Trp Ser Asp Gln
            1250                1255                1260 gaa ata tgg aaa gtt gca gat gag gtt ggg ctc aga tct gtg ata gaa    3963
Glu Ile Trp Lys Val Ala Asp Glu Val Gly Leu Arg Ser Val Ile Glu
        1265                1270                1275 cag ttt cct ggg aag ctt gac ttt gtc ctt gtg gat ggg ggc tgt gtc    4011
Gln Phe Pro Gly Lys Leu Asp Phe Val Leu Val Asp Gly Gly Cys Val
        1280                1285                1290 cta agc cat ggc cac aag cag ttg atg tgc ttg gct aga tct gtt ctc    4059
Leu Ser His Gly His Lys Gln Leu Met Cys Leu Ala Arg Ser Val Leu
        1295                1300                1305 agt aag gcg aag atc ttg ctg ctt gat gaa ccc agt gct cat ttg gat    4107
Ser Lys Ala Lys Ile Leu Leu Leu Asp Glu Pro Ser Ala His Leu Asp
1310                1315                1320                1325 cca gta aca tac caa ata att aga aga act cta aaa caa gca ttt gct    4155
Pro Val Thr Tyr Gln Ile Ile Arg Arg Thr Leu Lys Gln Ala Phe Ala
            1330                1335                1340 gat tgc aca gta att ctc tgt gaa cac agg ata gaa gca atg ctg gaa    4203
Asp Cys Thr Val Ile Leu Cys Glu His Arg Ile Glu Ala Met Leu Glu
        1345                1350                1355 tgc caa caa ttt ttg gtc ata gaa gag aac aaa gtg cgg cag tac gat    4251
Cys Gln Gln Phe Leu Val Ile Glu Glu Asn Lys Val Arg Gln Tyr Asp
        1360                1365                1370 tcc atc cag aaa ctg ctg aac gag agg agc ctc ttc cgg caa gcc atc    4299
Ser Ile Gln Lys Leu Leu Asn Glu Arg Ser Leu Phe Arg Gln Ala Ile
1375                1380                1385 agc ccc tcc gac agg gtg aag ctc ttt ccc cac cgg aac tca agc aag    4347
Ser Pro Ser Asp Arg Val Lys Leu Phe Pro His Arg Asn Ser Ser Lys
1390                1395                1400                1405 tgc aag tct aag ccc cag att gct gct ctg aaa gag gag aca gaa gaa    4395
Cys Lys Ser Lys Pro Gln Ile Ala Ala Leu Lys Glu Glu Thr Glu Glu
            1410                1415                1420 gag gtg caa gat aca agg ctt tag                                    4419
Glu Val Gln Asp Thr Arg Leu  *
        1425

<210> SEQ ID NO 3
<211> LENGTH: 4410
<212> TYPE: DNA
<213> ORGANISM: homo sapiens
<220> FEATURE:
<221> NAME/KEY: CDS
<222> LOCATION: (133)...(4410)

<400> SEQUENCE: 3
aattggaagc aaatgacatc acagcaggtc agagaaaaag ggttgagcgg caggcaccca    60
gagtagtagg tctttggcat taggagcttg agcccagacg gccctagcag ggaccccagc   120
```

-continued

```
gcccgagaga cc atg cag agg tcg cct ctg gaa aag gcc agc gtt gtc tcc          171
           Met Gln Arg Ser Pro Leu Glu Lys Ala Ser Val Val Ser
            1               5                  10 aaa ctt ttt ttc agc tgg acc aga cca att ttg agg aaa gga tac aga            219
Lys Leu Phe Phe Ser Trp Thr Arg Pro Ile Leu Arg Lys Gly Tyr Arg
 15              20                  25 cag cgc ctg gaa ttg tca gac ata tac caa atc cct tct gtt gat tct            267
Gln Arg Leu Glu Leu Ser Asp Ile Tyr Gln Ile Pro Ser Val Asp Ser
 30              35                  40                  45 gct gac aat cta tct gaa aaa ttg gaa aga gaa tgg gat aga gag ctg            315
Ala Asp Asn Leu Ser Glu Lys Leu Glu Arg Glu Trp Asp Arg Glu Leu
                 50                  55                  60 gct tca aag aaa aat cct aaa ctc att aat gcc ctt cgg cga tgt ttt            363
Ala Ser Lys Lys Asn Pro Lys Leu Ile Asn Ala Leu Arg Arg Cys Phe
             65                  70                  75 ttc tgg aga ttt atg ttc tat gga atc ttt tta tat tta ggg gaa gtc            411
Phe Trp Arg Phe Met Phe Tyr Gly Ile Phe Leu Tyr Leu Gly Glu Val
         80                  85                  90 acc aaa gca gta cag cct ctc tta ctg gga aga atc ata gct tcc tat            459
Thr Lys Ala Val Gln Pro Leu Leu Leu Gly Arg Ile Ile Ala Ser Tyr
     95                  100                 105 gac ccg gat aac aag gag gaa cgc tct atc gcg att tat cta ggc ata            507
Asp Pro Asp Asn Lys Glu Glu Arg Ser Ile Ala Ile Tyr Leu Gly Ile
110                 115                 120                 125 ggc tta tgc ctt ctc ttt att gtg agg aca ctg ctc cta cac cca gcc            555
Gly Leu Cys Leu Leu Phe Ile Val Arg Thr Leu Leu Leu His Pro Ala
                 130                 135                 140 att ttt ggc ctt cat cac att gga atg cag atg aga ata gct atg ttt            603
Ile Phe Gly Leu His His Ile Gly Met Gln Met Arg Ile Ala Met Phe
             145                 150                 155 agt ttg att tat aag aag act tta aag ctg tca agc cgt gtt cta gat            651
Ser Leu Ile Tyr Lys Lys Thr Leu Lys Leu Ser Ser Arg Val Leu Asp
         160                 165                 170 aaa ata agt att gga caa ctt gtt agt ctc ctt tcc aac aac ctg aac            699
Lys Ile Ser Ile Gly Gln Leu Val Ser Leu Leu Ser Asn Asn Leu Asn
     175                 180                 185 aaa ttt gat gaa gga ctt gca ttg gca cat ttc gtg tgg atc gct cct            747
Lys Phe Asp Glu Gly Leu Ala Leu Ala His Phe Val Trp Ile Ala Pro
190                 195                 200                 205 ttg caa gtg gca ctc ctc atg ggg cta atc tgg gag ttg tta cag gcg            795
Leu Gln Val Ala Leu Leu Met Gly Leu Ile Trp Glu Leu Leu Gln Ala
                 210                 215                 220 tct gcc ttc tgt gga ctt ggt ttc ctg ata gtc ctt gcc ctt ttt cag            843
Ser Ala Phe Cys Gly Leu Gly Phe Leu Ile Val Leu Ala Leu Phe Gln
             225                 230                 235 gct ggg cta ggg aga atg atg atg aag tac aga gat cag aga gct ggg            891
Ala Gly Leu Gly Arg Met Met Met Lys Tyr Arg Asp Gln Arg Ala Gly
         240                 245                 250 aag atc agt gaa aga ctt gtg att acc tca gaa atg att gaa aat atc            939
Lys Ile Ser Glu Arg Leu Val Ile Thr Ser Glu Met Ile Glu Asn Ile
     255                 260                 265 caa tct gtt aag gca tac tgc tgg gaa gaa gca atg gaa aaa atg att            987
Gln Ser Val Lys Ala Tyr Cys Trp Glu Glu Ala Met Glu Lys Met Ile
270                 275                 280                 285 gaa aac tta aga caa aca gaa ctg aaa ctg act cgg aag gca gcc tat           1035
Glu Asn Leu Arg Gln Thr Glu Leu Lys Leu Thr Arg Lys Ala Ala Tyr
                 290                 295                 300 gtg aga tac ttc aat agc tca gcc ttc ttc ttc tca ggg ttc ttt gtg           1083
Val Arg Tyr Phe Asn Ser Ser Ala Phe Phe Phe Ser Gly Phe Phe Val
```

-continued

```
                     305                 310                 315
gtg ttt tta tct gtg ctt ccc tat gca cta atc aaa gga atc atc ctc    1131
Val Phe Leu Ser Val Leu Pro Tyr Ala Leu Ile Lys Gly Ile Ile Leu
        320                 325                 330 cgg aaa ata ttc acc acc atc tca ttc tgc att gtt ctg cgc atg gcg    1179
Arg Lys Ile Phe Thr Thr Ile Ser Phe Cys Ile Val Leu Arg Met Ala
335                 340                 345 gtc act cgg caa ttt ccc tgg gct gta caa aca tgg tat gac tct ctt    1227
Val Thr Arg Gln Phe Pro Trp Ala Val Gln Thr Trp Tyr Asp Ser Leu
350                 355                 360                 365 gga gca ata aac aaa ata cag gat ttc tta caa aag caa gaa tat aag    1275
Gly Ala Ile Asn Lys Ile Gln Asp Phe Leu Gln Lys Gln Glu Tyr Lys
                370                 375                 380 aca ttg gaa tat aac tta acg act aca gaa gta gtg atg gag aat gta    1323
Thr Leu Glu Tyr Asn Leu Thr Thr Thr Glu Val Val Met Glu Asn Val
            385                 390                 395 aca gcc ttc tgg gag gag gga ttt ggg gaa tta ttt gag aaa gca aaa    1371
Thr Ala Phe Trp Glu Glu Gly Phe Gly Glu Leu Phe Glu Lys Ala Lys
        400                 405                 410 caa aac aat aac aat aga aaa act tct aat ggt gat gac agc ctc ttc    1419
Gln Asn Asn Asn Asn Arg Lys Thr Ser Asn Gly Asp Asp Ser Leu Phe
415                 420                 425 ttc agt aat ttc tca ctt ctt ggt act cct gtc ctg aaa gat att aat    1467
Phe Ser Asn Phe Ser Leu Leu Gly Thr Pro Val Leu Lys Asp Ile Asn
430                 435                 440                 445 ttc aag ata gaa aga gga cag ttg ttg gcg gtt gct gga tcc act gga    1515
Phe Lys Ile Glu Arg Gly Gln Leu Leu Ala Val Ala Gly Ser Thr Gly
                450                 455                 460 gca ggc aag act tca ctt cta atg atg att atg gga gaa ctg gag cct    1563
Ala Gly Lys Thr Ser Leu Leu Met Met Ile Met Gly Glu Leu Glu Pro
            465                 470                 475 tca gag ggt aaa att aag cac agt gga aga att tca ttc tgt tct cag    1611
Ser Glu Gly Lys Ile Lys His Ser Gly Arg Ile Ser Phe Cys Ser Gln
        480                 485                 490 ttt tcc tgg att atg cct ggc acc att aaa gaa aat atc atc ttt ggt    1659
Phe Ser Trp Ile Met Pro Gly Thr Ile Lys Glu Asn Ile Ile Phe Gly
495                 500                 505 gtt tcc tat gat gaa tat aga tac aga agc gtc atc aaa gca tgc caa    1707
Val Ser Tyr Asp Glu Tyr Arg Tyr Arg Ser Val Ile Lys Ala Cys Gln
510                 515                 520                 525 cta gaa gag gac atc tcc aag ttt gca gag aaa gac aat ata gtt ctt    1755
Leu Glu Glu Asp Ile Ser Lys Phe Ala Glu Lys Asp Asn Ile Val Leu
                530                 535                 540 gga gaa ggt gga atc aca ctg agt gga ggt caa cga gca aga att tct    1803
Gly Glu Gly Gly Ile Thr Leu Ser Gly Gly Gln Arg Ala Arg Ile Ser
            545                 550                 555 tta gca aga gca gta tac aaa gat gct gat ttg tat tta tta gac tct    1851
Leu Ala Arg Ala Val Tyr Lys Asp Ala Asp Leu Tyr Leu Leu Asp Ser
        560                 565                 570 cct ttt gga tac cta gat gtt tta aca gaa aaa gaa ata ttt gaa agc    1899
Pro Phe Gly Tyr Leu Asp Val Leu Thr Glu Lys Glu Ile Phe Glu Ser
575                 580                 585 tgt gtc tgt aaa ctg atg gct aac aaa act agg att ttg gtc act tct    1947
Cys Val Cys Lys Leu Met Ala Asn Lys Thr Arg Ile Leu Val Thr Ser
590                 595                 600                 605 aaa atg gaa cat tta aag aaa gct gac aaa ata tta att ttg cat gaa    1995
Lys Met Glu His Leu Lys Lys Ala Asp Lys Ile Leu Ile Leu His Glu
                610                 615                 620 ggt agc agc tat ttt tat ggg aca ttt tca gaa ctc caa aat cta cag    2043
```

```
                Gly Ser Ser Tyr Phe Tyr Gly Thr Phe Ser Glu Leu Gln Asn Leu Gln
                            625                 630                 635 cca gac ttt agc tca aaa ctc atg gga tgt gat tct ttc gac caa ttt          2091
Pro Asp Phe Ser Ser Lys Leu Met Gly Cys Asp Ser Phe Asp Gln Phe
            640                 645                 650 agt gca gaa aga aga aat tca atc cta act gag acc tta cac cgt ttc          2139
Ser Ala Glu Arg Arg Asn Ser Ile Leu Thr Glu Thr Leu His Arg Phe
            655                 660                 665 tca tta gaa gga gat gct cct gtc tcc tgg aca gaa aca aaa aaa caa          2187
Ser Leu Glu Gly Asp Ala Pro Val Ser Trp Thr Glu Thr Lys Lys Gln
670                 675                 680                 685 tct ttt aaa cag act gga gag ttt ggg gaa aaa agg aag aat tct att          2235
Ser Phe Lys Gln Thr Gly Glu Phe Gly Glu Lys Arg Lys Asn Ser Ile
                690                 695                 700 ctc aat cca atc aac tct atc gaa gag gat tct gat gag cct tta gag          2283
Leu Asn Pro Ile Asn Ser Ile Glu Glu Asp Ser Asp Glu Pro Leu Glu
                705                 710                 715 aga agg ctg tcc tta gta cca gat tct gag cag gga gag gcg ata cac          2331
Arg Arg Leu Ser Leu Val Pro Asp Ser Glu Gln Gly Glu Ala Ile His
                720                 725                 730 cga aag aca aca gca tcc aca cga aaa gtg tca ctg gcc cct cag gca          2379
Arg Lys Thr Thr Ala Ser Thr Arg Lys Val Ser Leu Ala Pro Gln Ala
            735                 740                 745 aac ttg act gaa ctg gat ata tat tca aga agg tta tct caa gaa act          2427
Asn Leu Thr Glu Leu Asp Ile Tyr Ser Arg Arg Leu Ser Gln Glu Thr
750                 755                 760                 765 ggc ttg gaa ata agt gaa gaa att aac gaa gaa gac tta aag gag gat          2475
Gly Leu Glu Ile Ser Glu Glu Ile Asn Glu Glu Asp Leu Lys Glu Asp
                770                 775                 780 atg gag agc ata cca gca gtg act aca tgg aac aca tac ctt cga tat          2523
Met Glu Ser Ile Pro Ala Val Thr Thr Trp Asn Thr Tyr Leu Arg Tyr
                785                 790                 795 att act gtc cac aag agc tta att ttt gtg cta att tgg tgc tta gta          2571
Ile Thr Val His Lys Ser Leu Ile Phe Val Leu Ile Trp Cys Leu Val
                800                 805                 810 att ttt ctg gca gag gtg gct gct tct ttg gtt gtg ctg tgg ctc ctt          2619
Ile Phe Leu Ala Glu Val Ala Ala Ser Leu Val Val Leu Trp Leu Leu
            815                 820                 825 gga aac act cct ctt caa gac aaa ggg aat agt act cat agt aga aat          2667
Gly Asn Thr Pro Leu Gln Asp Lys Gly Asn Ser Thr His Ser Arg Asn
830                 835                 840                 845 aac agc tat gca gtg att atc acc agc acc agt tcg tat tat gtg ttt          2715
Asn Ser Tyr Ala Val Ile Ile Thr Ser Thr Ser Ser Tyr Tyr Val Phe
                850                 855                 860 tac att tac gtg gga gta gcc gac act ttg ctt gct atg gga ttc ttc          2763
Tyr Ile Tyr Val Gly Val Ala Asp Thr Leu Leu Ala Met Gly Phe Phe
            865                 870                 875 aga ggt cta cca ctg gtg cat act cta atc aca gtg tcg aaa att tta          2811
Arg Gly Leu Pro Leu Val His Thr Leu Ile Thr Val Ser Lys Ile Leu
            880                 885                 890 cac cac aaa atg tta cat tct gtt ctt caa gca cct atg tca acc ctc          2859
His His Lys Met Leu His Ser Val Leu Gln Ala Pro Met Ser Thr Leu
            895                 900                 905 aac acg ttg aaa gca ggt ggg att ctt aat aga ttc tcc aaa gat ata          2907
Asn Thr Leu Lys Ala Gly Gly Ile Leu Asn Arg Phe Ser Lys Asp Ile
910                 915                 920                 925 gca att ttg gat gac ctt ctg cct ctt acc ata ttt gac ttc atc cag          2955
Ala Ile Leu Asp Asp Leu Leu Pro Leu Thr Ile Phe Asp Phe Ile Gln
                930                 935                 940
```

| | |
|---|---|
| ttg tta tta att gtg att gga gct ata gca gtt gtc gca gtt tta caa<br>Leu Leu Leu Ile Val Ile Gly Ala Ile Ala Val Val Ala Val Leu Gln<br>         945                    950                  955 | 3003 |
| ccc tac atc ttt gtt gca aca gtg cca gtg ata gtg gct ttt att atg<br>Pro Tyr Ile Phe Val Ala Thr Val Pro Val Ile Val Ala Phe Ile Met<br>         960                    965                  970 | 3051 |
| ttg aga gca tat ttc ctc caa acc tca cag caa ctc aaa caa ctg gaa<br>Leu Arg Ala Tyr Phe Leu Gln Thr Ser Gln Gln Leu Lys Gln Leu Glu<br>975                    980                  985 | 3099 |
| tct gaa ggc agg agt cca att ttc act cat ctt gtt aca agc tta aaa<br>Ser Glu Gly Arg Ser Pro Ile Phe Thr His Leu Val Thr Ser Leu Lys<br> 990                 995               1000            1005 | 3147 |
| gga cta tgg aca ctt cgt gcc ttc gga cgg cag cct tac ttt gaa act<br>Gly Leu Trp Thr Leu Arg Ala Phe Gly Arg Gln Pro Tyr Phe Glu Thr<br>        1010                   1015                1020 | 3195 |
| ctg ttc cac aaa gct ctg aat tta cat act gcc aac tgg ttc ttg tac<br>Leu Phe His Lys Ala Leu Asn Leu His Thr Ala Asn Trp Phe Leu Tyr<br>        1025                   1030                1035 | 3243 |
| ctg tca aca ctg cgc tgg ttc caa atg aga ata gaa atg att ttt gtc<br>Leu Ser Thr Leu Arg Trp Phe Gln Met Arg Ile Glu Met Ile Phe Val<br>        1040                   1045                1050 | 3291 |
| atc ttc ttc att gct gtt acc ttc att tcc att tta aca aca gga gaa<br>Ile Phe Phe Ile Ala Val Thr Phe Ile Ser Ile Leu Thr Thr Gly Glu<br>        1055                   1060                1065 | 3339 |
| gga gaa gga aga gtt ggt att atc ctg act tta gcc atg aat atc atg<br>Gly Glu Gly Arg Val Gly Ile Ile Leu Thr Leu Ala Met Asn Ile Met<br>1070                 1075                1080            1085 | 3387 |
| agt aca ttg cag tgg gct gta aac tcc agc ata gat gtg gat agc ttg<br>Ser Thr Leu Gln Trp Ala Val Asn Ser Ser Ile Asp Val Asp Ser Leu<br>        1090                   1095                1100 | 3435 |
| atg cga tct gtg agc cga gtc ttt aag ttc att gac atg cca aca gaa<br>Met Arg Ser Val Ser Arg Val Phe Lys Phe Ile Asp Met Pro Thr Glu<br>        1105                   1110                1115 | 3483 |
| ggt aaa cct acc aag tca acc aaa cca tac aag aat ggc caa ctc tcg<br>Gly Lys Pro Thr Lys Ser Thr Lys Pro Tyr Lys Asn Gly Gln Leu Ser<br>        1120                   1125                1130 | 3531 |
| aaa gtt atg att att gag aat tca cac gtg aag aaa gat gac atc tgg<br>Lys Val Met Ile Ile Glu Asn Ser His Val Lys Lys Asp Asp Ile Trp<br>        1135                   1140                1145 | 3579 |
| ccc tca ggg ggc caa atg act gtc aaa gat ctc aca gca aaa tac aca<br>Pro Ser Gly Gly Gln Met Thr Val Lys Asp Leu Thr Ala Lys Tyr Thr<br>1150                 1155                1160            1165 | 3627 |
| gaa ggt gga aat gcc ata tta gag aac att tcc ttc tca ata agt cct<br>Glu Gly Gly Asn Ala Ile Leu Glu Asn Ile Ser Phe Ser Ile Ser Pro<br>                              1170                1175            1180 | 3675 |
| ggc cag agg gtg ggc ctc ttg gga aga act gga tca ggg aag agt act<br>Gly Gln Arg Val Gly Leu Leu Gly Arg Thr Gly Ser Gly Lys Ser Thr<br>        1185                   1190                1195 | 3723 |
| ttg tta tca gct ttt ttg aga cta ctg aac act gaa gga gaa atc cag<br>Leu Leu Ser Ala Phe Leu Arg Leu Leu Asn Thr Glu Gly Glu Ile Gln<br>        1200                   1205                1210 | 3771 |
| atc gat ggt gtg tct tgg gat tca ata act ttg caa cag tgg agg aaa<br>Ile Asp Gly Val Ser Trp Asp Ser Ile Thr Leu Gln Gln Trp Arg Lys<br>        1215                   1220                1225 | 3819 |
| gcc ttt gga gtg ata cca cag aaa gta ttt att ttt tct gga aca ttt<br>Ala Phe Gly Val Ile Pro Gln Lys Val Phe Ile Phe Ser Gly Thr Phe<br>1230                 1235                1240            1245 | 3867 |
| aga aaa aac ttg gat ccc tat gaa cag tgg agt gat caa gaa ata tgg<br>Arg Lys Asn Leu Asp Pro Tyr Glu Gln Trp Ser Asp Gln Glu Ile Trp<br>        1250                   1255                1260 | 3915 |

-continued

```
aaa gtt gca gat gag gtt ggg ctc aga tct gtg ata gaa cag ttt cct      3963
Lys Val Ala Asp Glu Val Gly Leu Arg Ser Val Ile Glu Gln Phe Pro
            1265                1270                1275 ggg aag ctt gac ttt gtc ctt gtg gat ggg ggc tgt gtc cta agc cat      4011
Gly Lys Leu Asp Phe Val Leu Val Asp Gly Gly Cys Val Leu Ser His
        1280                1285                1290 ggc cac aag cag ttg atg tgc ttg gct aga tct gtt ctc agt aag gcg      4059
Gly His Lys Gln Leu Met Cys Leu Ala Arg Ser Val Leu Ser Lys Ala
    1295                1300                1305 aag atc ttg ctg ctt gat gaa ccc agt gct cat ttg gat cca gta aca      4107
Lys Ile Leu Leu Leu Asp Glu Pro Ser Ala His Leu Asp Pro Val Thr
1310                1315                1320                1325 tac caa ata att aga aga act cta aaa caa gca ttt gct gat tgc aca      4155
Tyr Gln Ile Ile Arg Arg Thr Leu Lys Gln Ala Phe Ala Asp Cys Thr
                1330                1335                1340 gta att ctc tgt gaa cac agg ata gaa gca atg ctg gaa tgc caa caa      4203
Val Ile Leu Cys Glu His Arg Ile Glu Ala Met Leu Glu Cys Gln Gln
            1345                1350                1355 ttt ttg gtc ata gaa gag aac aaa gtg cgg cag tac gat tcc atc cag      4251
Phe Leu Val Ile Glu Glu Asn Lys Val Arg Gln Tyr Asp Ser Ile Gln
        1360                1365                1370 aaa ctg ctg aac gag agg agc ctc ttc cgg caa gcc atc agc ccc tcc      4299
Lys Leu Leu Asn Glu Arg Ser Leu Phe Arg Gln Ala Ile Ser Pro Ser
    1375                1380                1385 gac agg gtg aag ctc ttt ccc cac cgg aac tca agc aag tgc aag tct      4347
Asp Arg Val Lys Leu Phe Pro His Arg Asn Ser Ser Lys Cys Lys Ser
1390                1395                1400                1405 aag ccc cag att gct gct ctg aaa gag gag aca gaa gaa gag gtg caa      4395
Lys Pro Gln Ile Ala Ala Leu Lys Glu Glu Thr Glu Glu Glu Val Gln
                1410                1415                1420 gat aca agg ctt tag                                                   4410
Asp Thr Arg Leu *
            1425

<210> SEQ ID NO 4
<211> LENGTH: 4371
<212> TYPE: DNA
<213> ORGANISM: homo sapiens
<220> FEATURE:
<221> NAME/KEY: CDS
<222> LOCATION: (133)...(4371)

<400> SEQUENCE: 4
aattggaagc aaatgacatc acagcaggtc agagaaaaag ggttgagcgg caggcaccca     60
gagtagtagg tctttggcat taggagcttg agcccagacg gccctagcag ggaccccagc    120
gcccgagaga cc atg cag agg tcg cct ctg gaa aag gcc agc gtt gtc tcc    171
             Met Gln Arg Ser Pro Leu Glu Lys Ala Ser Val Val Ser
               1               5                  10 aaa ctt ttt ttc agc tgg acc aga cca att ttg agg aaa gga tac aga      219
Lys Leu Phe Phe Ser Trp Thr Arg Pro Ile Leu Arg Lys Gly Tyr Arg
 15                  20                  25 cag cgc ctg gaa ttg tca gac ata tac caa atc cct tct gtt gat tct      267
Gln Arg Leu Glu Leu Ser Asp Ile Tyr Gln Ile Pro Ser Val Asp Ser
 30                  35                  40                  45 gct gac aat cta tct gaa aaa ttg gaa aga gaa tgg gat aga gag ctg      315
Ala Asp Asn Leu Ser Glu Lys Leu Glu Arg Glu Trp Asp Arg Glu Leu
                 50                  55                  60 gct tca aag aaa aat cct aaa ctc att aat gcc ctt cgg cga tgt ttt      363
Ala Ser Lys Lys Asn Pro Lys Leu Ile Asn Ala Leu Arg Arg Cys Phe
             65                  70                  75
```

-continued

| | |
|---|---|
| ttc tgg aga ttt atg ttc tat gga atc ttt tta tat tta ggg aa gtc<br>Phe Trp Arg Phe Met Phe Tyr Gly Ile Phe Leu Tyr Leu Gly Glu Val<br>      80                        85                        90 | 411 |
| acc aaa gca gta cag cct ctc tta ctg gga aga atc ata gct tcc tat<br>Thr Lys Ala Val Gln Pro Leu Leu Leu Gly Arg Ile Ile Ala Ser Tyr<br>      95                      100                       105 | 459 |
| gac ccg gat aac aag gag gaa cgc tct atc gcg att tat cta ggc ata<br>Asp Pro Asp Asn Lys Glu Glu Arg Ser Ile Ala Ile Tyr Leu Gly Ile<br>110                  115                      120                   125 | 507 |
| ggc tta tgc ctt ctc ttt att gtg agg aca ctg ctc cta cac cca gcc<br>Gly Leu Cys Leu Leu Phe Ile Val Arg Thr Leu Leu Leu His Pro Ala<br>             130                       135                   140 | 555 |
| att ttt ggc ctt cat cac att gga atg cag atg aga ata gct atg ttt<br>Ile Phe Gly Leu His His Ile Gly Met Gln Met Arg Ile Ala Met Phe<br>             145                       150                   155 | 603 |
| agt ttg att tat aag aag act tta aag ctg tca agc cgt gtt cta gat<br>Ser Leu Ile Tyr Lys Lys Thr Leu Lys Leu Ser Ser Arg Val Leu Asp<br>             160                       165                   170 | 651 |
| aaa ata agt att gga caa ctt gtt agt ctc ctt tcc aac aac ctg aac<br>Lys Ile Ser Ile Gly Gln Leu Val Ser Leu Leu Ser Asn Asn Leu Asn<br>175                  180                      185 | 699 |
| aaa ttt gat gaa gga ctt gca ttg gca cat ttc gtg tgg atc gct cct<br>Lys Phe Asp Glu Gly Leu Ala Leu Ala His Phe Val Trp Ile Ala Pro<br>190                  195                      200                   205 | 747 |
| ttg caa gtg gca ctc ctc atg ggg cta atc tgg gag ttg tta cag gcg<br>Leu Gln Val Ala Leu Leu Met Gly Leu Ile Trp Glu Leu Leu Gln Ala<br>             210                       215                   220 | 795 |
| tct gcc ttc tgt gga ctt ggt ttc ctg ata gtc ctt gcc ctt ttt cag<br>Ser Ala Phe Cys Gly Leu Gly Phe Leu Ile Val Leu Ala Leu Phe Gln<br>             225                       230                   235 | 843 |
| gct ggg cta ggg aga atg atg atg aag tac aga gat cag aga gct ggg<br>Ala Gly Leu Gly Arg Met Met Met Lys Tyr Arg Asp Gln Arg Ala Gly<br>             240                       245                   250 | 891 |
| aag atc agt gaa aga ctt gtg att acc tca gaa atg att gaa aat atc<br>Lys Ile Ser Glu Arg Leu Val Ile Thr Ser Glu Met Ile Glu Asn Ile<br>255                  260                      265 | 939 |
| caa tct gtt aag gca tac tgc tgg gaa gaa gca atg gaa aaa atg att<br>Gln Ser Val Lys Ala Tyr Cys Trp Glu Glu Ala Met Glu Lys Met Ile<br>270                  275                      280                   285 | 987 |
| gaa aac tta aga caa aca gaa ctg aaa ctg act cgg aag gca gcc tat<br>Glu Asn Leu Arg Gln Thr Glu Leu Lys Leu Thr Arg Lys Ala Ala Tyr<br>                  290                      295                   300 | 1035 |
| gtg aga tac ttc aat agc tca gcc ttc ttc ttc tca ggg ttc ttt gtg<br>Val Arg Tyr Phe Asn Ser Ser Ala Phe Phe Phe Ser Gly Phe Phe Val<br>305                  310                      315 | 1083 |
| gtg ttt tta tct gtg ctt ccc tat gca cta atc aaa gga atc atc ctc<br>Val Phe Leu Ser Val Leu Pro Tyr Ala Leu Ile Lys Gly Ile Ile Leu<br>             320                       325                   330 | 1131 |
| cgg aaa ata ttc acc acc atc tca ttc tgc att gtt ctg cgc atg gcg<br>Arg Lys Ile Phe Thr Thr Ile Ser Phe Cys Ile Val Leu Arg Met Ala<br>335                  340                      345 | 1179 |
| gtc act cgg caa ttt ccc tgg gct gta caa aca tgg tat gac tct ctt<br>Val Thr Arg Gln Phe Pro Trp Ala Val Gln Thr Trp Tyr Asp Ser Leu<br>350                  355                      360                   365 | 1227 |
| gga gca ata aac aaa ata cag gat ttc tta caa aag caa gaa tat aag<br>Gly Ala Ile Asn Lys Ile Gln Asp Phe Leu Gln Lys Gln Glu Tyr Lys<br>                  370                      375                   380 | 1275 |
| aca ttg gaa tat aac tta acg act aca gaa gta gtg atg gag aat gta<br>Thr Leu Glu Tyr Asn Leu Thr Thr Thr Glu Val Val Met Glu Asn Val | 1323 |

-continued

|  |  |  | 385 |  |  |  | 390 |  |  |  | 395 |  |  |  |  |
|---|---|---|---|---|---|---|---|---|---|---|---|---|---|---|---|
| aca | gcc | ttc | tgg | gag | gag | gga | ttt | ggg | gaa | tta | ttt | gag | aaa | gca | aaa | 1371 |
| Thr | Ala | Phe | Trp | Glu | Glu | Gly | Phe | Gly | Glu | Leu | Phe | Glu | Lys | Ala | Lys |  |
|  |  |  | 400 |  |  |  | 405 |  |  |  | 410 |  |  |  |  |

```
caa aac aat aac aat aga aaa act tct aat ggt gat gac agc ctc ttc      1419
Gln Asn Asn Asn Asn Arg Lys Thr Ser Asn Gly Asp Asp Ser Leu Phe
        415                 420                 425 ttc agt aat ttc tca ctt ctt ggt act cct gtc ctg aaa gat att aat      1467
Phe Ser Asn Phe Ser Leu Leu Gly Thr Pro Val Leu Lys Asp Ile Asn
430                 435                 440                 445 ttc aag ata gaa aga gga cag ttg ttg gcg gtt gct gga tcc act gga      1515
Phe Lys Ile Glu Arg Gly Gln Leu Leu Ala Val Ala Gly Ser Thr Gly
                450                 455                 460 gca ggc aag act tca ctt cta atg atg att atg gga gaa ctg gag cct      1563
Ala Gly Lys Thr Ser Leu Leu Met Met Ile Met Gly Glu Leu Glu Pro
            465                 470                 475 tca gag ggt aaa att aag cac agt gga aga att tca ttc tgt tct cag      1611
Ser Glu Gly Lys Ile Lys His Ser Gly Arg Ile Ser Phe Cys Ser Gln
        480                 485                 490 ttt tcc tgg att atg cct ggc acc att aaa gaa aat atc atc ttt ggt      1659
Phe Ser Trp Ile Met Pro Gly Thr Ile Lys Glu Asn Ile Ile Phe Gly
    495                 500                 505 gtt tcc tat gat gaa tat aga tac aga agc gtc atc aaa gca tgc caa      1707
Val Ser Tyr Asp Glu Tyr Arg Tyr Arg Ser Val Ile Lys Ala Cys Gln
510                 515                 520                 525 cta gaa gag gac atc tcc aag ttt gca gag aaa gac aat ata gtt ctt      1755
Leu Glu Glu Asp Ile Ser Lys Phe Ala Glu Lys Asp Asn Ile Val Leu
                530                 535                 540 gga gaa ggt gga atc aca ctg agt gga ggt caa cga gca aga att tct      1803
Gly Glu Gly Gly Ile Thr Leu Ser Gly Gly Gln Arg Ala Arg Ile Ser
            545                 550                 555 tta gca aga gca gta tac aaa gat gct gat ttg tat tta tta gac tct      1851
Leu Ala Arg Ala Val Tyr Lys Asp Ala Asp Leu Tyr Leu Leu Asp Ser
        560                 565                 570 cct ttt gga tac cta gat gtt tta aca gaa aaa gaa ata ttt gaa agc      1899
Pro Phe Gly Tyr Leu Asp Val Leu Thr Glu Lys Glu Ile Phe Glu Ser
575                 580                 585 tgt gtc tgt aaa ctg atg gct aac aaa act agg att ttg gtc act tct      1947
Cys Val Cys Lys Leu Met Ala Asn Lys Thr Arg Ile Leu Val Thr Ser
590                 595                 600                 605 aaa atg gaa cat tta aag aaa gct gac aaa ata tta att ttg cat gaa      1995
Lys Met Glu His Leu Lys Lys Ala Asp Lys Ile Leu Ile Leu His Glu
                610                 615                 620 ggt agc agc tat ttt tat ggg aca ttt tca gaa ctc caa aat cta cag      2043
Gly Ser Ser Tyr Phe Tyr Gly Thr Phe Ser Glu Leu Gln Asn Leu Gln
            625                 630                 635 cca gac ttt agc tca aaa ctc atg gga tgt gat tct ttc gac caa ttt      2091
Pro Asp Phe Ser Ser Lys Leu Met Gly Cys Asp Ser Phe Asp Gln Phe
        640                 645                 650 agt gca gaa aga aga aat tca atc cta act gag acc tta cac cgt ttc      2139
Ser Ala Glu Arg Arg Asn Ser Ile Leu Thr Glu Thr Leu His Arg Phe
655                 660                 665 tca tta gaa gga gat gct cct gtc tcc tgg aca gaa aca aaa aaa caa      2187
Ser Leu Glu Gly Asp Ala Pro Val Ser Trp Thr Glu Thr Lys Lys Gln
670                 675                 680                 685 tct ttt aaa cag act gga gag ttt ggg gaa aaa agg aag aat tct att      2235
Ser Phe Lys Gln Thr Gly Glu Phe Gly Glu Lys Arg Lys Asn Ser Ile
                690                 695                 700 ctc aat cca atc aac tct atc gaa gag gat tct gat gag cct tta gag      2283
```

```
Leu Asn Pro Ile Asn Ser Ile Glu Glu Asp Ser Asp Glu Pro Leu Glu
            705                 710                 715 aga agg ctg tcc tta gta cca gat tct gag cag gga gag gcg ata cac    2331
Arg Arg Leu Ser Leu Val Pro Asp Ser Glu Gln Gly Glu Ala Ile His
        720                 725                 730 cga aag aca aca gca tcc aca cga aaa gtg tca ctg gcc cct cag gca    2379
Arg Lys Thr Thr Ala Ser Thr Arg Lys Val Ser Leu Ala Pro Gln Ala
735                 740                 745 aac ttg act gaa ctg gat ata tat tca aga agg tta tct caa gaa act    2427
Asn Leu Thr Glu Leu Asp Ile Tyr Ser Arg Arg Leu Ser Gln Glu Thr
750                 755                 760                 765 ggc ttg gat atg gag agc ata cca gca gtg act aca tgg aac aca tac    2475
Gly Leu Asp Met Glu Ser Ile Pro Ala Val Thr Thr Trp Asn Thr Tyr
                770                 775                 780 ctt cga tat att act gtc cac aag agc tta att ttt gtg cta att tgg    2523
Leu Arg Tyr Ile Thr Val His Lys Ser Leu Ile Phe Val Leu Ile Trp
            785                 790                 795 tgc tta gta att ttt ctg gca gag gtg gct gct tct ttg gtt gtg ctg    2571
Cys Leu Val Ile Phe Leu Ala Glu Val Ala Ala Ser Leu Val Val Leu
        800                 805                 810 tgg ctc ctt gga aac act cct ctt caa gac aaa ggg aat agt act cat    2619
Trp Leu Leu Gly Asn Thr Pro Leu Gln Asp Lys Gly Asn Ser Thr His
815                 820                 825 agt aga aat aac agc tat gca gtg att atc acc agc acc agt tcg tat    2667
Ser Arg Asn Asn Ser Tyr Ala Val Ile Ile Thr Ser Thr Ser Ser Tyr
830                 835                 840                 845 tat gtg ttt tac att tac gtg gga gta gcc gac act ttg ctt gct atg    2715
Tyr Val Phe Tyr Ile Tyr Val Gly Val Ala Asp Thr Leu Leu Ala Met
                850                 855                 860 gga ttc ttc aga ggt cta cca ctg gtg cat act cta atc aca gtg tcg    2763
Gly Phe Phe Arg Gly Leu Pro Leu Val His Thr Leu Ile Thr Val Ser
            865                 870                 875 aaa att tta cac cac aaa atg tta cat tct gtt ctt caa gca cct atg    2811
Lys Ile Leu His His Lys Met Leu His Ser Val Leu Gln Ala Pro Met
        880                 885                 890 tca acc ctc aac acg ttg aaa gca ggt ggg att ctt aat aga ttc tcc    2859
Ser Thr Leu Asn Thr Leu Lys Ala Gly Gly Ile Leu Asn Arg Phe Ser
895                 900                 905 aaa gat ata gca att ttg gat gac ctt ctg cct ctt acc ata ttt gac    2907
Lys Asp Ile Ala Ile Leu Asp Asp Leu Leu Pro Leu Thr Ile Phe Asp
910                 915                 920                 925 ttc atc cag ttg tta tta att gtg att gga gct ata gca gtt gtc gca    2955
Phe Ile Gln Leu Leu Leu Ile Val Ile Gly Ala Ile Ala Val Val Ala
                930                 935                 940 gtt tta caa ccc tac atc ttt gtt gca aca gtg cca gtg ata gtg gct    3003
Val Leu Gln Pro Tyr Ile Phe Val Ala Thr Val Pro Val Ile Val Ala
            945                 950                 955 ttt att atg ttg aga gca tat ttc ctc caa acc tca cag caa ctc aaa    3051
Phe Ile Met Leu Arg Ala Tyr Phe Leu Gln Thr Ser Gln Gln Leu Lys
        960                 965                 970 caa ctg gaa tct gaa ggc agg agt cca att ttc act cat ctt gtt aca    3099
Gln Leu Glu Ser Glu Gly Arg Ser Pro Ile Phe Thr His Leu Val Thr
975                 980                 985 agc tta aaa gga cta tgg aca ctt cgt gcc ttc gga cgg cag cct tac    3147
Ser Leu Lys Gly Leu Trp Thr Leu Arg Ala Phe Gly Arg Gln Pro Tyr
990                 995                 1000                1005 ttt gaa act ctg ttc cac aaa gct ctg aat tta cat act gcc aac tgg    3195
Phe Glu Thr Leu Phe His Lys Ala Leu Asn Leu His Thr Ala Asn Trp
                1010                1015                1020
```

```
ttc ttg tac ctg tca aca ctg cgc tgg ttc caa atg aga ata gaa atg      3243
Phe Leu Tyr Leu Ser Thr Leu Arg Trp Phe Gln Met Arg Ile Glu Met
             1025                1030                1035 att ttt gtc atc ttc ttc att gct gtt acc ttc att tcc att tta aca      3291
Ile Phe Val Ile Phe Phe Ile Ala Val Thr Phe Ile Ser Ile Leu Thr
    1040                1045                1050 aca gga gaa gga gaa gga aga gtt ggt att atc ctg act tta gcc atg      3339
Thr Gly Glu Gly Glu Gly Arg Val Gly Ile Ile Leu Thr Leu Ala Met
1055                1060                1065 aat atc atg agt aca ttg cag tgg gct gta aac tcc agc ata gat gtg      3387
Asn Ile Met Ser Thr Leu Gln Trp Ala Val Asn Ser Ser Ile Asp Val
1070            1075                1080                1085 gat agc ttg atg cga tct gtg agc cga gtc ttt aag ttc att gac atg      3435
Asp Ser Leu Met Arg Ser Val Ser Arg Val Phe Lys Phe Ile Asp Met
                1090                1095                1100 cca aca gaa ggt aaa cct acc aag tca acc aaa cca tac aag aat ggc      3483
Pro Thr Glu Gly Lys Pro Thr Lys Ser Thr Lys Pro Tyr Lys Asn Gly
             1105                1110                1115 caa ctc tcg aaa gtt atg att att gag aat tca cac gtg aag aaa gat      3531
Gln Leu Ser Lys Val Met Ile Ile Glu Asn Ser His Val Lys Lys Asp
         1120                1125                1130 gac atc tgg ccc tca ggg ggc caa atg act gtc aaa gat ctc aca gca      3579
Asp Ile Trp Pro Ser Gly Gly Gln Met Thr Val Lys Asp Leu Thr Ala
     1135                1140                1145 aaa tac aca gaa ggt gga aat gcc ata tta gag aac att tcc ttc tca      3627
Lys Tyr Thr Glu Gly Gly Asn Ala Ile Leu Glu Asn Ile Ser Phe Ser
1150                1155                1160                1165 ata agt cct ggc cag agg gtg ggc ctc ttg gga aga act gga tca ggg      3675
Ile Ser Pro Gly Gln Arg Val Gly Leu Leu Gly Arg Thr Gly Ser Gly
                1170                1175                1180 aag agt act ttg tta tca gct ttt ttg aga cta ctg aac act gaa gga      3723
Lys Ser Thr Leu Leu Ser Ala Phe Leu Arg Leu Leu Asn Thr Glu Gly
             1185                1190                1195 gaa atc cag atc gat ggt gtg tct tgg gat tca ata act ttg caa cag      3771
Glu Ile Gln Ile Asp Gly Val Ser Trp Asp Ser Ile Thr Leu Gln Gln
         1200                1205                1210 tgg agg aaa gcc ttt gga gtg ata cca cag aaa gta ttt att ttt tct      3819
Trp Arg Lys Ala Phe Gly Val Ile Pro Gln Lys Val Phe Ile Phe Ser
     1215                1220                1225 gga aca ttt aga aaa aac ttg gat ccc tat gaa cag tgg agt gat caa      3867
Gly Thr Phe Arg Lys Asn Leu Asp Pro Tyr Glu Gln Trp Ser Asp Gln
1230                1235                1240                1245 gaa ata tgg aaa gtt gca gat gag gtt ggg ctc aga tct gtg ata gaa      3915
Glu Ile Trp Lys Val Ala Asp Glu Val Gly Leu Arg Ser Val Ile Glu
                1250                1255                1260 cag ttt cct ggg aag ctt gac ttt gtc ctt gtg gat ggg ggc tgt gtc      3963
Gln Phe Pro Gly Lys Leu Asp Phe Val Leu Val Asp Gly Gly Cys Val
             1265                1270                1275 cta agc cat ggc cac aag cag ttg atg tgc ttg gct aga tct gtt ctc      4011
Leu Ser His Gly His Lys Gln Leu Met Cys Leu Ala Arg Ser Val Leu
         1280                1285                1290 agt aag gcg aag atc ttg ctg ctt gat gaa ccc agt gct cat ttg gat      4059
Ser Lys Ala Lys Ile Leu Leu Leu Asp Glu Pro Ser Ala His Leu Asp
     1295                1300                1305 cca gta aca tac caa ata att aga aga act cta aaa caa gca ttt gct      4107
Pro Val Thr Tyr Gln Ile Ile Arg Arg Thr Leu Lys Gln Ala Phe Ala
1310                1315                1320                1325 gat tgc aca gta att ctc tgt gaa cac agg ata gaa gca atg ctg gaa      4155
Asp Cys Thr Val Ile Leu Cys Glu His Arg Ile Glu Ala Met Leu Glu
                1330                1335                1340
```

-continued

```
tgc caa caa ttt ttg gtc ata gaa gag aac aaa gtg cgg cag tac gat      4203
Cys Gln Gln Phe Leu Val Ile Glu Glu Asn Lys Val Arg Gln Tyr Asp
            1345                1350                1355 tcc atc cag aaa ctg ctg aac gag agg agc ctc ttc cgg caa gcc atc      4251
Ser Ile Gln Lys Leu Leu Asn Glu Arg Ser Leu Phe Arg Gln Ala Ile
    1360                1365                1370 agc ccc tcc gac agg gtg aag ctc ttt ccc cac cgg aac tca agc aag      4299
Ser Pro Ser Asp Arg Val Lys Leu Phe Pro His Arg Asn Ser Ser Lys
1375                1380                1385 tgc aag tct aag ccc cag att gct gct ctg aaa gag gag aca gaa gaa      4347
Cys Lys Ser Lys Pro Gln Ile Ala Ala Leu Lys Glu Glu Thr Glu Glu
1390                1395                1400                1405 gag gtg caa gat aca agg ctt tag                                      4371
Glu Val Gln Asp Thr Arg Leu *
            1410

<210> SEQ ID NO 5
<211> LENGTH: 4368
<212> TYPE: DNA
<213> ORGANISM: homo sapiens
<220> FEATURE:
<221> NAME/KEY: CDS
<222> LOCATION: (133)...(4368)

<400> SEQUENCE: 5
aattggaagc aaatgacatc acagcaggtc agagaaaaag ggttgagcgg caggcaccca       60
gagtagtagg tctttggcat taggagcttg agcccagacg gccctagcag ggaccccagc      120
gcccgagaga cc atg cag agg tcg cct ctg gaa aag gcc agc gtt gtc tcc      171
              Met Gln Arg Ser Pro Leu Glu Lys Ala Ser Val Val Ser
                1               5                   10 aaa ctt ttt ttc agc tgg acc aga cca att ttg agg aaa gga tac aga       219
Lys Leu Phe Phe Ser Trp Thr Arg Pro Ile Leu Arg Lys Gly Tyr Arg
        15                  20                  25 cag cgc ctg gaa ttg tca gac ata tac caa atc cct tct gtt gat tct       267
Gln Arg Leu Glu Leu Ser Asp Ile Tyr Gln Ile Pro Ser Val Asp Ser
30                  35                  40                  45 gct gac aat cta tct gaa aaa ttg gaa aga gaa tgg gat aga gag ctg       315
Ala Asp Asn Leu Ser Glu Lys Leu Glu Arg Glu Trp Asp Arg Glu Leu
                50                  55                  60 gct tca aag aaa aat cct aaa ctc att aat gcc ctt cgg cga tgt ttt       363
Ala Ser Lys Lys Asn Pro Lys Leu Ile Asn Ala Leu Arg Arg Cys Phe
            65                  70                  75 ttc tgg aga ttt atg ttc tat gga atc ttt tta tat tta ggg gaa gtc       411
Phe Trp Arg Phe Met Phe Tyr Gly Ile Phe Leu Tyr Leu Gly Glu Val
        80                  85                  90 acc aaa gca gta cag cct ctc tta ctg gga aga atc ata gct tcc tat       459
Thr Lys Ala Val Gln Pro Leu Leu Leu Gly Arg Ile Ile Ala Ser Tyr
    95                  100                 105 gac ccg gat aac aag gag gaa cgc tct atc gcg att tat cta ggc ata       507
Asp Pro Asp Asn Lys Glu Glu Arg Ser Ile Ala Ile Tyr Leu Gly Ile
110                 115                 120                 125 ggc tta tgc ctt ctc ttt att gtg agg aca ctg ctc cta cac cca gcc       555
Gly Leu Cys Leu Leu Phe Ile Val Arg Thr Leu Leu Leu His Pro Ala
                130                 135                 140 att ttt ggc ctt cat cac att gga atg cag atg aga ata gct atg ttt       603
Ile Phe Gly Leu His His Ile Gly Met Gln Met Arg Ile Ala Met Phe
            145                 150                 155 agt ttg att tat aag aag act tta aag ctg tca agc cgt gtt cta gat       651
Ser Leu Ile Tyr Lys Lys Thr Leu Lys Leu Ser Ser Arg Val Leu Asp
        160                 165                 170
```

-continued

```
aaa ata agt att gga caa ctt gtt agt ctc ctt tcc aac aac ctg aac      699
Lys Ile Ser Ile Gly Gln Leu Val Ser Leu Leu Ser Asn Asn Leu Asn
    175                 180                 185 aaa ttt gat gaa gga ctt gca ttg gca cat ttc gtg tgg atc gct cct      747
Lys Phe Asp Glu Gly Leu Ala Leu Ala His Phe Val Trp Ile Ala Pro
190                 195                 200                 205 ttg caa gtg gca ctc ctc atg ggg cta atc tgg gag ttg tta cag gcg      795
Leu Gln Val Ala Leu Leu Met Gly Leu Ile Trp Glu Leu Leu Gln Ala
                210                 215                 220 tct gcc ttc tgt gga ctt ggt ttc ctg ata gtc ctt gcc ctt ttt cag      843
Ser Ala Phe Cys Gly Leu Gly Phe Leu Ile Val Leu Ala Leu Phe Gln
            225                 230                 235 gct ggg cta ggg aga atg atg atg aag tac aga gat cag aga gct ggg      891
Ala Gly Leu Gly Arg Met Met Met Lys Tyr Arg Asp Gln Arg Ala Gly
        240                 245                 250 aag atc agt gaa aga ctt gtg att acc tca gaa atg att gaa aat atc      939
Lys Ile Ser Glu Arg Leu Val Ile Thr Ser Glu Met Ile Glu Asn Ile
    255                 260                 265 caa tct gtt aag gca tac tgc tgg gaa gaa gca atg gaa aaa atg att      987
Gln Ser Val Lys Ala Tyr Cys Trp Glu Glu Ala Met Glu Lys Met Ile
270                 275                 280                 285 gaa aac tta aga caa aca gaa ctg aaa ctg act cgg aag gca gcc tat     1035
Glu Asn Leu Arg Gln Thr Glu Leu Lys Leu Thr Arg Lys Ala Ala Tyr
                290                 295                 300 gtg aga tac ttc aat agc tca gcc ttc ttc ttc tca ggg ttc ttt gtg     1083
Val Arg Tyr Phe Asn Ser Ser Ala Phe Phe Phe Ser Gly Phe Phe Val
            305                 310                 315 gtg ttt tta tct gtg ctt ccc tat gca cta atc aaa gga atc atc ctc     1131
Val Phe Leu Ser Val Leu Pro Tyr Ala Leu Ile Lys Gly Ile Ile Leu
        320                 325                 330 cgg aaa ata ttc acc acc atc tca ttc tgc att gtt ctg cgc atg gcg     1179
Arg Lys Ile Phe Thr Thr Ile Ser Phe Cys Ile Val Leu Arg Met Ala
    335                 340                 345 gtc act cgg caa ttt ccc tgg gct gta caa aca tgg tat gac tct ctt     1227
Val Thr Arg Gln Phe Pro Trp Ala Val Gln Thr Trp Tyr Asp Ser Leu
350                 355                 360                 365 gga gca ata aac aaa ata cag gat ttc tta caa aag caa gaa tat aag     1275
Gly Ala Ile Asn Lys Ile Gln Asp Phe Leu Gln Lys Gln Glu Tyr Lys
                370                 375                 380 aca ttg gaa tat aac tta acg act aca gaa gta gtg atg gag aat gta     1323
Thr Leu Glu Tyr Asn Leu Thr Thr Thr Glu Val Val Met Glu Asn Val
            385                 390                 395 aca gcc ttc tgg gag gag gga ttt ggg gaa tta ttt gag aaa gca aaa     1371
Thr Ala Phe Trp Glu Glu Gly Phe Gly Glu Leu Phe Glu Lys Ala Lys
        400                 405                 410 caa aac aat aac aat aga aaa act tct aat ggt gat gac agc ctc ttc     1419
Gln Asn Asn Asn Asn Arg Lys Thr Ser Asn Gly Asp Asp Ser Leu Phe
    415                 420                 425 ttc agt aat ttc tca ctt ctt ggt act cct gtc ctg aaa gat att aat     1467
Phe Ser Asn Phe Ser Leu Leu Gly Thr Pro Val Leu Lys Asp Ile Asn
430                 435                 440                 445 ttc aag ata gaa aga gga cag ttg ttg gcg gtt gct gga tcc act gga     1515
Phe Lys Ile Glu Arg Gly Gln Leu Leu Ala Val Ala Gly Ser Thr Gly
                450                 455                 460 gca ggc aag act tca ctt cta atg atg att atg gga gaa ctg gag cct     1563
Ala Gly Lys Thr Ser Leu Leu Met Met Ile Met Gly Glu Leu Glu Pro
            465                 470                 475 tca gag ggt aaa att aag cac agt gga aga att tca ttc tgt tct cag     1611
Ser Glu Gly Lys Ile Lys His Ser Gly Arg Ile Ser Phe Cys Ser Gln
```

-continued

```
                480                 485                 490
ttt tcc tgg att atg cct ggc acc att aaa gaa aat atc atc ttt ggt      1659
Phe Ser Trp Ile Met Pro Gly Thr Ile Lys Glu Asn Ile Ile Phe Gly
    495                 500                 505 gtt tcc tat gat gaa tat aga tac aga agc gtc atc aaa gca tgc caa      1707
Val Ser Tyr Asp Glu Tyr Arg Tyr Arg Ser Val Ile Lys Ala Cys Gln
510                 515                 520                 525 cta gaa gag gac atc tcc aag ttt gca gag aaa gac aat ata gtt ctt      1755
Leu Glu Glu Asp Ile Ser Lys Phe Ala Glu Lys Asp Asn Ile Val Leu
                530                 535                 540 gga gaa ggt gga atc aca ctg agt gga ggt caa cga gca aga att tct      1803
Gly Glu Gly Gly Ile Thr Leu Ser Gly Gly Gln Arg Ala Arg Ile Ser
            545                 550                 555 tta gca aga gca gta tac aaa gat gct gat ttg tat tta tta gac tct      1851
Leu Ala Arg Ala Val Tyr Lys Asp Ala Asp Leu Tyr Leu Leu Asp Ser
        560                 565                 570 cct ttt gga tac cta gat gtt tta aca gaa aaa gaa ata ttt gaa agc      1899
Pro Phe Gly Tyr Leu Asp Val Leu Thr Glu Lys Glu Ile Phe Glu Ser
    575                 580                 585 tgt gtc tgt aaa ctg atg gct aac aaa act agg att ttg gtc act tct      1947
Cys Val Cys Lys Leu Met Ala Asn Lys Thr Arg Ile Leu Val Thr Ser
590                 595                 600                 605 aaa atg gaa cat tta aag aaa gct gac aaa ata tta att ttg cat gaa      1995
Lys Met Glu His Leu Lys Lys Ala Asp Lys Ile Leu Ile Leu His Glu
                610                 615                 620 ggt agc agc tat ttt tat ggg aca ttt tca gaa ctc caa aat cta cag      2043
Gly Ser Ser Tyr Phe Tyr Gly Thr Phe Ser Glu Leu Gln Asn Leu Gln
            625                 630                 635 cca gac ttt agc tca aaa ctc atg gga tgt gat tct ttc gac caa ttt      2091
Pro Asp Phe Ser Ser Lys Leu Met Gly Cys Asp Ser Phe Asp Gln Phe
        640                 645                 650 agt gca gaa aga aga aat tca atc cta act gag acc tta cac cgt ttc      2139
Ser Ala Glu Arg Arg Asn Ser Ile Leu Thr Glu Thr Leu His Arg Phe
    655                 660                 665 tca tta gaa gga gat gct cct gtc tcc tgg aca gaa aca aaa aaa caa      2187
Ser Leu Glu Gly Asp Ala Pro Val Ser Trp Thr Glu Thr Lys Lys Gln
670                 675                 680                 685 tct ttt aaa cag act gga gag ttt ggg gaa aaa agg aag aat tct att      2235
Ser Phe Lys Gln Thr Gly Glu Phe Gly Glu Lys Arg Lys Asn Ser Ile
                690                 695                 700 ctc aat cca atc aac tct acg ctt cag gca cga agg agg cag tct gtc      2283
Leu Asn Pro Ile Asn Ser Thr Leu Gln Ala Arg Arg Arg Gln Ser Val
            705                 710                 715 ctg aac ctg atg aca cac tca gtt aac caa ggt cag aac att cac cga      2331
Leu Asn Leu Met Thr His Ser Val Asn Gln Gly Gln Asn Ile His Arg
        720                 725                 730 aag aca aca gca tcc aca cga aaa gtg tca ctg gcc cct cag gca aac      2379
Lys Thr Thr Ala Ser Thr Arg Lys Val Ser Leu Ala Pro Gln Ala Asn
    735                 740                 745 ttg act gaa ctg gat ata tat tca aga agg tta tct caa gaa act ggc      2427
Leu Thr Glu Leu Asp Ile Tyr Ser Arg Arg Leu Ser Gln Glu Thr Gly
750                 755                 760                 765 ttg gat atg gag agc ata cca gca gtg act aca tgg aac aca tac ctt      2475
Leu Asp Met Glu Ser Ile Pro Ala Val Thr Thr Trp Asn Thr Tyr Leu
                770                 775                 780 cga tat att act gtc cac aag agc tta att ttt gtg cta att tgg tgc      2523
Arg Tyr Ile Thr Val His Lys Ser Leu Ile Phe Val Leu Ile Trp Cys
            785                 790                 795 tta gta att ttt ctg gca gag gtg gct gct tct ttg gtt gtg ctg tgg      2571
```

```
Leu Val Ile Phe Leu Ala Glu Val Ala Ser Leu Val Val Leu Trp
        800                 805                 810 ctc ctt gga aac act cct ctt caa gac aaa ggg aat agt act cat agt    2619
Leu Leu Gly Asn Thr Pro Leu Gln Asp Lys Gly Asn Ser Thr His Ser
    815                 820                 825 aga aat aac agc tat gca gtg att atc acc agc acc agt tcg tat tat    2667
Arg Asn Asn Ser Tyr Ala Val Ile Ile Thr Ser Thr Ser Ser Tyr Tyr
830                 835                 840                 845 gtg ttt tac att tac gtg gga gta gcc gac act ttg ctt gct atg gga    2715
Val Phe Tyr Ile Tyr Val Gly Val Ala Asp Thr Leu Leu Ala Met Gly
                850                 855                 860 ttc ttc aga ggt cta cca ctg gtg cat act cta atc aca gtg tcg aaa    2763
Phe Phe Arg Gly Leu Pro Leu Val His Thr Leu Ile Thr Val Ser Lys
            865                 870                 875 att tta cac cac aaa atg tta cat tct gtt ctt caa gca cct atg tca    2811
Ile Leu His His Lys Met Leu His Ser Val Leu Gln Ala Pro Met Ser
        880                 885                 890 acc ctc aac acg ttg aaa gca ggt ggg att ctt aat aga ttc tcc aaa    2859
Thr Leu Asn Thr Leu Lys Ala Gly Gly Ile Leu Asn Arg Phe Ser Lys
    895                 900                 905 gat ata gca att ttg gat gac ctt ctg cct ctt acc ata ttt gac ttc    2907
Asp Ile Ala Ile Leu Asp Asp Leu Leu Pro Leu Thr Ile Phe Asp Phe
910                 915                 920                 925 atc cag ttg tta tta att gtg att gga gct ata gca gtt gtc gca gtt    2955
Ile Gln Leu Leu Leu Ile Val Ile Gly Ala Ile Ala Val Val Ala Val
                930                 935                 940 tta caa ccc tac atc ttt gtt gca aca gtg cca gtg ata gtg gct ttt    3003
Leu Gln Pro Tyr Ile Phe Val Ala Thr Val Pro Val Ile Val Ala Phe
            945                 950                 955 att atg ttg aga gca tat ttc ctc caa acc tca cag caa ctc aaa caa    3051
Ile Met Leu Arg Ala Tyr Phe Leu Gln Thr Ser Gln Gln Leu Lys Gln
        960                 965                 970 ctg gaa tct gaa ggc agg agt cca att ttc act cat ctt gtt aca agc    3099
Leu Glu Ser Glu Gly Arg Ser Pro Ile Phe Thr His Leu Val Thr Ser
    975                 980                 985 tta aaa gga cta tgg aca ctt cgt gcc ttc gga cgg cag cct tac ttt    3147
Leu Lys Gly Leu Trp Thr Leu Arg Ala Phe Gly Arg Gln Pro Tyr Phe
 990                 995                 1000                1005 gaa act ctg ttc cac aaa gct ctg aat tta cat act gcc aac tgg ttc    3195
Glu Thr Leu Phe His Lys Ala Leu Asn Leu His Thr Ala Asn Trp Phe
                1010                1015                1020 ttg tac ctg tca aca ctg cgc tgg ttc caa atg aga ata gaa atg att    3243
Leu Tyr Leu Ser Thr Leu Arg Trp Phe Gln Met Arg Ile Glu Met Ile
            1025                1030                1035 ttt gtc atc ttc ttc att gct gtt acc ttc att tcc att tta aca aca    3291
Phe Val Ile Phe Phe Ile Ala Val Thr Phe Ile Ser Ile Leu Thr Thr
        1040                1045                1050 gga gaa gga gaa gga aga gtt ggt att atc ctg act tta gcc atg aat    3339
Gly Glu Gly Glu Gly Arg Val Gly Ile Ile Leu Thr Leu Ala Met Asn
    1055                1060                1065 atc atg agt aca ttg cag tgg gct gta aac tcc agc ata gat gtg gat    3387
Ile Met Ser Thr Leu Gln Trp Ala Val Asn Ser Ser Ile Asp Val Asp
1070                1075                1080                1085 agc ttg atg cga tct gtg agc cga gtc ttt aag ttc att gac atg cca    3435
Ser Leu Met Arg Ser Val Ser Arg Val Phe Lys Phe Ile Asp Met Pro
                1090                1095                1100 aca gaa ggt aaa cct acc aag tca acc aaa cca tac aag aat ggc caa    3483
Thr Glu Gly Lys Pro Thr Lys Ser Thr Lys Pro Tyr Lys Asn Gly Gln
            1105                1110                1115
```

```
ctc tcg aaa gtt atg att att gag aat tca cac gtg aag aaa gat gac      3531
Leu Ser Lys Val Met Ile Ile Glu Asn Ser His Val Lys Lys Asp Asp
        1120                1125                1130 atc tgg ccc tca ggg ggc caa atg act gtc aaa gat ctc aca gca aaa      3579
Ile Trp Pro Ser Gly Gly Gln Met Thr Val Lys Asp Leu Thr Ala Lys
    1135                1140                1145 tac aca gaa ggt gga aat gcc ata tta gag aac att tcc ttc tca ata      3627
Tyr Thr Glu Gly Gly Asn Ala Ile Leu Glu Asn Ile Ser Phe Ser Ile
1150                1155                1160                1165 agt cct ggc cag agg gtg ggc ctc ttg gga aga act gga tca ggg aag      3675
Ser Pro Gly Gln Arg Val Gly Leu Leu Gly Arg Thr Gly Ser Gly Lys
            1170                1175                1180 agt act ttg tta tca gct ttt ttg aga cta ctg aac act gaa gga gaa      3723
Ser Thr Leu Leu Ser Ala Phe Leu Arg Leu Leu Asn Thr Glu Gly Glu
        1185                1190                1195 atc cag atc gat ggt gtg tct tgg gat tca ata act ttg caa cag tgg      3771
Ile Gln Ile Asp Gly Val Ser Trp Asp Ser Ile Thr Leu Gln Gln Trp
    1200                1205                1210 agg aaa gcc ttt gga gtg ata cca cag aaa gta ttt att ttt tct gga      3819
Arg Lys Ala Phe Gly Val Ile Pro Gln Lys Val Phe Ile Phe Ser Gly
1215                1220                1225 aca ttt aga aaa aac ttg gat ccc tat gaa cag tgg agt gat caa gaa      3867
Thr Phe Arg Lys Asn Leu Asp Pro Tyr Glu Gln Trp Ser Asp Gln Glu
1230                1235                1240                1245 ata tgg aaa gtt gca gat gag gtt ggg ctc aga tct gtg ata gaa cag      3915
Ile Trp Lys Val Ala Asp Glu Val Gly Leu Arg Ser Val Ile Glu Gln
            1250                1255                1260 ttt cct ggg aag ctt gac ttt gtc ctt gtg gat ggg ggc tgt gtc cta      3963
Phe Pro Gly Lys Leu Asp Phe Val Leu Val Asp Gly Gly Cys Val Leu
        1265                1270                1275 agc cat ggc cac aag cag ttg atg tgc ttg gct aga tct gtt ctc agt      4011
Ser His Gly His Lys Gln Leu Met Cys Leu Ala Arg Ser Val Leu Ser
    1280                1285                1290 aag gcg aag atc ttg ctg ctt gat gaa ccc agt gct cat ttg gat cca      4059
Lys Ala Lys Ile Leu Leu Leu Asp Glu Pro Ser Ala His Leu Asp Pro
1295                1300                1305 gta aca tac caa ata att aga aga act cta aaa caa gca ttt gct gat      4107
Val Thr Tyr Gln Ile Ile Arg Arg Thr Leu Lys Gln Ala Phe Ala Asp
1310                1315                1320                1325 tgc aca gta att ctc tgt gaa cac agg ata gaa gca atg ctg gaa tgc      4155
Cys Thr Val Ile Leu Cys Glu His Arg Ile Glu Ala Met Leu Glu Cys
            1330                1335                1340 caa caa ttt ttg gtc ata gaa gag aac aaa gtg cgg cag tac gat tcc      4203
Gln Gln Phe Leu Val Ile Glu Glu Asn Lys Val Arg Gln Tyr Asp Ser
        1345                1350                1355 atc cag aaa ctg ctg aac gag agg agc ctc ttc cgg caa gcc atc agc      4251
Ile Gln Lys Leu Leu Asn Glu Arg Ser Leu Phe Arg Gln Ala Ile Ser
    1360                1365                1370 ccc tcc gac agg gtg aag ctc ttt ccc cac cgg aac tca agc aag tgc      4299
Pro Ser Asp Arg Val Lys Leu Phe Pro His Arg Asn Ser Ser Lys Cys
1375                1380                1385 aag tct aag ccc cag att gct gct ctg aaa gag gag aca gaa gaa gag      4347
Lys Ser Lys Pro Gln Ile Ala Ala Leu Lys Glu Glu Thr Glu Glu Glu
1390                1395                1400                1405 gtg caa gat aca agg ctt tag                                          4368
Val Gln Asp Thr Arg Leu *
            1410

<210> SEQ ID NO 6
<211> LENGTH: 4347
```

```
<212> TYPE: DNA
<213> ORGANISM: homo sapiens
<220> FEATURE:
<221> NAME/KEY: CDS
<222> LOCATION: (133)...(4347)

<400> SEQUENCE: 6
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga cc atg cag agg tcg cct ctg gaa aag gcc agc gtt gtc tcc     171
              Met Gln Arg Ser Pro Leu Glu Lys Ala Ser Val Val Ser
                1               5                  10 aaa ctt ttt ttc agc tgg acc aga cca att ttg agg aaa gga tac aga       219
Lys Leu Phe Phe Ser Trp Thr Arg Pro Ile Leu Arg Lys Gly Tyr Arg
 15                  20                  25 cag cgc ctg gaa ttg tca gac ata tac caa atc cct tct gtt gat tct       267
Gln Arg Leu Glu Leu Ser Asp Ile Tyr Gln Ile Pro Ser Val Asp Ser
 30                  35                  40                  45 gct gac aat cta tct gaa aaa ttg gaa aga gaa tgg gat aga gag ctg       315
Ala Asp Asn Leu Ser Glu Lys Leu Glu Arg Glu Trp Asp Arg Glu Leu
                 50                  55                  60 gct tca aag aaa aat cct aaa ctc att aat gcc ctt cgg cga tgt ttt       363
Ala Ser Lys Lys Asn Pro Lys Leu Ile Asn Ala Leu Arg Arg Cys Phe
             65                  70                  75 ttc tgg aga ttt atg ttc tat gga atc ttt tta tat tta ggg gaa gtc       411
Phe Trp Arg Phe Met Phe Tyr Gly Ile Phe Leu Tyr Leu Gly Glu Val
 80                  85                  90 acc aaa gca gta cag cct ctc tta ctg gga aga atc ata gct tcc tat       459
Thr Lys Ala Val Gln Pro Leu Leu Leu Gly Arg Ile Ile Ala Ser Tyr
 95                 100                 105 gac ccg gat aac aag gag gaa cgc tct atc gcg att tat cta ggc ata       507
Asp Pro Asp Asn Lys Glu Glu Arg Ser Ile Ala Ile Tyr Leu Gly Ile
110                 115                 120                 125 ggc tta tgc ctt ctc ttt att gtg agg aca ctg ctc cta cac cca gcc       555
Gly Leu Cys Leu Leu Phe Ile Val Arg Thr Leu Leu Leu His Pro Ala
                130                 135                 140 att ttt ggc ctt cat cac att gga atg cag atg aga ata gct atg ttt       603
Ile Phe Gly Leu His His Ile Gly Met Gln Met Arg Ile Ala Met Phe
            145                 150                 155 agt ttg att tat aag aag act tta aag ctg tca agc cgt gtt cta gat       651
Ser Leu Ile Tyr Lys Lys Thr Leu Lys Leu Ser Ser Arg Val Leu Asp
        160                 165                 170 aaa ata agt att gga caa ctt gtt agt ctc ctt tcc aac aac ctg aac       699
Lys Ile Ser Ile Gly Gln Leu Val Ser Leu Leu Ser Asn Asn Leu Asn
175                 180                 185 aaa ttt gat gaa gga ctt gca ttg gca cat ttc gtg tgg atc gct cct       747
Lys Phe Asp Glu Gly Leu Ala Leu Ala His Phe Val Trp Ile Ala Pro
190                 195                 200                 205 ttg caa gtg gca ctc ctc atg ggg cta atc tgg gag ttg tta cag gcg       795
Leu Gln Val Ala Leu Leu Met Gly Leu Ile Trp Glu Leu Leu Gln Ala
                210                 215                 220 tct gcc ttc tgt gga ctt ggt ttc ctg ata gtc ctt gcc ctt ttt cag       843
Ser Ala Phe Cys Gly Leu Gly Phe Leu Ile Val Leu Ala Leu Phe Gln
            225                 230                 235 gct ggg cta ggg aga atg atg atg aag tac aga gat cag aga gct ggg       891
Ala Gly Leu Gly Arg Met Met Met Lys Tyr Arg Asp Gln Arg Ala Gly
        240                 245                 250 aag atc agt gaa aga ctt gtg att acc tca gaa atg att gaa aat atc       939
Lys Ile Ser Glu Arg Leu Val Ile Thr Ser Glu Met Ile Glu Asn Ile
255                 260                 265
```

| | | |
|---|---|---|
| caa tct gtt aag gca tac tgc tgg gaa gaa gca atg gaa aaa atg att | | 987 |
| Gln Ser Val Lys Ala Tyr Cys Trp Glu Glu Ala Met Glu Lys Met Ile | | |
| 270 275 280 285 | | |
| gaa aac tta aga caa aca gaa ctg aaa ctg act cgg aag gca gcc tat | | 1035 |
| Glu Asn Leu Arg Gln Thr Glu Leu Lys Leu Thr Arg Lys Ala Ala Tyr | | |
| 290 295 300 | | |
| gtg aga tac ttc aat agc tca gcc ttc ttc ttc tca ggg ttc ttt gtg | | 1083 |
| Val Arg Tyr Phe Asn Ser Ser Ala Phe Phe Phe Ser Gly Phe Phe Val | | |
| 305 310 315 | | |
| gtg ttt tta tct gtg ctt ccc tat gca cta atc aaa gga atc atc ctc | | 1131 |
| Val Phe Leu Ser Val Leu Pro Tyr Ala Leu Ile Lys Gly Ile Ile Leu | | |
| 320 325 330 | | |
| cgg aaa ata ttc acc acc atc tca ttc tgc att gtt ctg cgc atg gcg | | 1179 |
| Arg Lys Ile Phe Thr Thr Ile Ser Phe Cys Ile Val Leu Arg Met Ala | | |
| 335 340 345 | | |
| gtc act cgg caa ttt ccc tgg gct gta caa aca tgg tat gac tct ctt | | 1227 |
| Val Thr Arg Gln Phe Pro Trp Ala Val Gln Thr Trp Tyr Asp Ser Leu | | |
| 350 355 360 365 | | |
| gga gca ata aac aaa ata cag gat ttc tta caa aag caa gaa tat aag | | 1275 |
| Gly Ala Ile Asn Lys Ile Gln Asp Phe Leu Gln Lys Gln Glu Tyr Lys | | |
| 370 375 380 | | |
| aca ttg gaa tat aac tta acg act aca gaa gta gtg atg gag aat gta | | 1323 |
| Thr Leu Glu Tyr Asn Leu Thr Thr Thr Glu Val Val Met Glu Asn Val | | |
| 385 390 395 | | |
| aca gcc ttc tgg gag gag gga ttt ggg gaa tta ttt gag aaa gca aaa | | 1371 |
| Thr Ala Phe Trp Glu Glu Gly Phe Gly Glu Leu Phe Glu Lys Ala Lys | | |
| 400 405 410 | | |
| caa aac aat aac aat aga aaa act tct aat ggt gat gac agc ctc ttc | | 1419 |
| Gln Asn Asn Asn Asn Arg Lys Thr Ser Asn Gly Asp Asp Ser Leu Phe | | |
| 415 420 425 | | |
| ttc agt aat ttc tca ctt ctt ggt act cct gtc ctg aaa gat att aat | | 1467 |
| Phe Ser Asn Phe Ser Leu Leu Gly Thr Pro Val Leu Lys Asp Ile Asn | | |
| 430 435 440 445 | | |
| ttc aag ata gaa aga gga cag ttg ttg gcg gtt gct gga tcc act gga | | 1515 |
| Phe Lys Ile Glu Arg Gly Gln Leu Leu Ala Val Ala Gly Ser Thr Gly | | |
| 450 455 460 | | |
| gca ggc aag act tca ctt cta atg atg att atg gga gaa ctg gag cct | | 1563 |
| Ala Gly Lys Thr Ser Leu Leu Met Met Ile Met Gly Glu Leu Glu Pro | | |
| 465 470 475 | | |
| tca gag ggt aaa att aag cac agt gga aga att tca ttc tgt tct cag | | 1611 |
| Ser Glu Gly Lys Ile Lys His Ser Gly Arg Ile Ser Phe Cys Ser Gln | | |
| 480 485 490 | | |
| ttt tcc tgg att atg cct ggc acc att aaa gaa aat atc atc ttt ggt | | 1659 |
| Phe Ser Trp Ile Met Pro Gly Thr Ile Lys Glu Asn Ile Ile Phe Gly | | |
| 495 500 505 | | |
| gtt tcc tat gat gaa tat aga tac aga agc gtc atc aaa gca tgc caa | | 1707 |
| Val Ser Tyr Asp Glu Tyr Arg Tyr Arg Ser Val Ile Lys Ala Cys Gln | | |
| 510 515 520 525 | | |
| cta gaa gag gac atc tcc aag ttt gca gag aaa gac aat ata gtt ctt | | 1755 |
| Leu Glu Glu Asp Ile Ser Lys Phe Ala Glu Lys Asp Asn Ile Val Leu | | |
| 530 535 540 | | |
| gga gaa ggt gga atc aca ctg agt gga ggt caa cga gca aga att tct | | 1803 |
| Gly Glu Gly Gly Ile Thr Leu Ser Gly Gly Gln Arg Ala Arg Ile Ser | | |
| 545 550 555 | | |
| tta gca aga gca gta tac aaa gat gct gat ttg tat tta tta gac tct | | 1851 |
| Leu Ala Arg Ala Val Tyr Lys Asp Ala Asp Leu Tyr Leu Leu Asp Ser | | |
| 560 565 570 | | |
| cct ttt gga tac cta gat gtt tta aca gaa aaa gaa ata ttt gaa agc | | 1899 |
| Pro Phe Gly Tyr Leu Asp Val Leu Thr Glu Lys Glu Ile Phe Glu Ser | | |

```
                575                 580                 585
tgt gtc tgt aaa ctg atg gct aac aaa act agg att ttg gtc act tct      1947
Cys Val Cys Lys Leu Met Ala Asn Lys Thr Arg Ile Leu Val Thr Ser
590                 595                 600                 605 aaa atg gaa cat tta aag aaa gct gac aaa ata tta att ttg cat gaa      1995
Lys Met Glu His Leu Lys Lys Ala Asp Lys Ile Leu Ile Leu His Glu
                610                 615                 620 ggt agc agc tat ttt tat ggg aca ttt tca gaa ctc caa aat cta cag      2043
Gly Ser Ser Tyr Phe Tyr Gly Thr Phe Ser Glu Leu Gln Asn Leu Gln
                625                 630                 635 cca gac ttt agc tca aaa ctc atg gga tgt gat tct ttc gac caa ttt      2091
Pro Asp Phe Ser Ser Lys Leu Met Gly Cys Asp Ser Phe Asp Gln Phe
            640                 645                 650 agt gca gaa aga aga aat tca atc cta act gag acc tta cac cgt ttc      2139
Ser Ala Glu Arg Arg Asn Ser Ile Leu Thr Glu Thr Leu His Arg Phe
            655                 660                 665 tca tta gaa gga gat gct cct gtc tcc tgg aca gaa aca aaa aaa caa      2187
Ser Leu Glu Gly Asp Ala Pro Val Ser Trp Thr Glu Thr Lys Lys Gln
670                 675                 680                 685 tct ttt aaa cag act gga gag ttt ggg gaa aaa agg aag aat tct att      2235
Ser Phe Lys Gln Thr Gly Glu Phe Gly Glu Lys Arg Lys Asn Ser Ile
                690                 695                 700 ctc aat cca atc aac tct ata cga aaa ttt tcc att gtg caa aag act      2283
Leu Asn Pro Ile Asn Ser Ile Arg Lys Phe Ser Ile Val Gln Lys Thr
            705                 710                 715 ccc tta caa atg aat ggc atc gaa gag gat tct gat gag cct tta gag      2331
Pro Leu Gln Met Asn Gly Ile Glu Glu Asp Ser Asp Glu Pro Leu Glu
            720                 725                 730 aga agg ctg tcc tta gta cca gat tct gag cag gga gag gcg ata ctg      2379
Arg Arg Leu Ser Leu Val Pro Asp Ser Glu Gln Gly Glu Ala Ile Leu
735                 740                 745 cct cgc atc agc gtg atc agc act ggc ccc gat atg gag agc ata cca      2427
Pro Arg Ile Ser Val Ile Ser Thr Gly Pro Asp Met Glu Ser Ile Pro
750                 755                 760                 765 gca gtg act aca tgg aac aca tac ctt cga tat att act gtc cac aag      2475
Ala Val Thr Thr Trp Asn Thr Tyr Leu Arg Tyr Ile Thr Val His Lys
                770                 775                 780 agc tta att ttt gtg cta att tgg tgc tta gta att ttt ctg gca gag      2523
Ser Leu Ile Phe Val Leu Ile Trp Cys Leu Val Ile Phe Leu Ala Glu
            785                 790                 795 gtg gct gct tct ttg gtt gtg ctg tgg ctc ctt gga aac act cct ctt      2571
Val Ala Ala Ser Leu Val Val Leu Trp Leu Leu Gly Asn Thr Pro Leu
800                 805                 810 caa gac aaa ggg aat agt act cat agt aga aat aac agc tat gca gtg      2619
Gln Asp Lys Gly Asn Ser Thr His Ser Arg Asn Asn Ser Tyr Ala Val
815                 820                 825 att atc acc agc acc agt tcg tat tat gtg ttt tac att tac gtg gga      2667
Ile Ile Thr Ser Thr Ser Ser Tyr Tyr Val Phe Tyr Ile Tyr Val Gly
830                 835                 840                 845 gta gcc gac act ttg ctt gct atg gga ttc ttc aga ggt cta cca ctg      2715
Val Ala Asp Thr Leu Leu Ala Met Gly Phe Phe Arg Gly Leu Pro Leu
            850                 855                 860 gtg cat act cta atc aca gtg tcg aaa att tta cac cac aaa atg tta      2763
Val His Thr Leu Ile Thr Val Ser Lys Ile Leu His His Lys Met Leu
            865                 870                 875 cat tct gtt ctt caa gca cct atg tca acc ctc aac acg ttg aaa gca      2811
His Ser Val Leu Gln Ala Pro Met Ser Thr Leu Asn Thr Leu Lys Ala
            880                 885                 890 ggt ggg att ctt aat aga ttc tcc aaa gat ata gca att ttg gat gac      2859
```

```
Gly Gly Ile Leu Asn Arg Phe Ser Lys Asp Ile Ala Ile Leu Asp Asp
        895                 900                 905 ctt ctg cct ctt acc ata ttt gac ttc atc cag ttg tta tta att gtg      2907
Leu Leu Pro Leu Thr Ile Phe Asp Phe Ile Gln Leu Leu Leu Ile Val
910                 915                 920                 925 att gga gct ata gca gtt gtc gca gtt tta caa ccc tac atc ttt gtt      2955
Ile Gly Ala Ile Ala Val Val Ala Val Leu Gln Pro Tyr Ile Phe Val
                930                 935                 940 gca aca gtg cca gtg ata gtg gct ttt att atg ttg aga gca tat ttc      3003
Ala Thr Val Pro Val Ile Val Ala Phe Ile Met Leu Arg Ala Tyr Phe
            945                 950                 955 ctc caa acc tca cag caa ctc aaa caa ctg gaa tct gaa ggc agg agt      3051
Leu Gln Thr Ser Gln Gln Leu Lys Gln Leu Glu Ser Glu Gly Arg Ser
        960                 965                 970 cca att ttc act cat ctt gtt aca agc tta aaa gga cta tgg aca ctt      3099
Pro Ile Phe Thr His Leu Val Thr Ser Leu Lys Gly Leu Trp Thr Leu
    975                 980                 985 cgt gcc ttc gga cgg cag cct tac ttt gaa act ctg ttc cac aaa gct      3147
Arg Ala Phe Gly Arg Gln Pro Tyr Phe Glu Thr Leu Phe His Lys Ala
990                 995                 1000                1005 ctg aat tta cat act gcc aac tgg ttc ttg tac ctg tca aca ctg cgc      3195
Leu Asn Leu His Thr Ala Asn Trp Phe Leu Tyr Leu Ser Thr Leu Arg
                1010                1015                1020 tgg ttc caa atg aga ata gaa atg att ttt gtc atc ttc ttc att gct      3243
Trp Phe Gln Met Arg Ile Glu Met Ile Phe Val Ile Phe Phe Ile Ala
            1025                1030                1035 gtt acc ttc att tcc att tta aca aca gga gaa gga gaa gga aga gtt      3291
Val Thr Phe Ile Ser Ile Leu Thr Thr Gly Glu Gly Glu Gly Arg Val
        1040                1045                1050 ggt att atc ctg act tta gcc atg aat atc atg agt aca ttg cag tgg      3339
Gly Ile Ile Leu Thr Leu Ala Met Asn Ile Met Ser Thr Leu Gln Trp
    1055                1060                1065 gct gta aac tcc agc ata gat gtg gat agc ttg atg cga tct gtg agc      3387
Ala Val Asn Ser Ser Ile Asp Val Asp Ser Leu Met Arg Ser Val Ser
1070                1075                1080                1085 cga gtc ttt aag ttc att gac atg cca aca gaa ggt aaa cct acc aag      3435
Arg Val Phe Lys Phe Ile Asp Met Pro Thr Glu Gly Lys Pro Thr Lys
                1090                1095                1100 tca acc aaa cca tac aag aat ggc caa ctc tcg aaa gtt atg att att      3483
Ser Thr Lys Pro Tyr Lys Asn Gly Gln Leu Ser Lys Val Met Ile Ile
            1105                1110                1115 gag aat tca cac gtg aag aaa gat gac atc tgg ccc tca ggg ggc caa      3531
Glu Asn Ser His Val Lys Lys Asp Asp Ile Trp Pro Ser Gly Gly Gln
        1120                1125                1130 atg act gtc aaa gat ctc aca gca aaa tac aca gaa ggt gga aat gcc      3579
Met Thr Val Lys Asp Leu Thr Ala Lys Tyr Thr Glu Gly Gly Asn Ala
    1135                1140                1145 ata tta gag aac att tcc ttc tca ata agt cct ggc cag agg tgg ggc      3627
Ile Leu Glu Asn Ile Ser Phe Ser Ile Ser Pro Gly Gln Arg Val Gly
1150                1155                1160                1165 ctc ttg gga aga act gga tca ggg aag agt act ttg tta tca gct ttt      3675
Leu Leu Gly Arg Thr Gly Ser Gly Lys Ser Thr Leu Leu Ser Ala Phe
                1170                1175                1180 ttg aga cta ctg aac act gaa gga gaa atc cag atc gat ggt gtg tct      3723
Leu Arg Leu Leu Asn Thr Glu Gly Glu Ile Gln Ile Asp Gly Val Ser
            1185                1190                1195 tgg gat tca ata act ttg caa cag tgg agg aaa gcc ttt gga gtg ata      3771
Trp Asp Ser Ile Thr Leu Gln Gln Trp Arg Lys Ala Phe Gly Val Ile
        1200                1205                1210
```

-continued

```
cca cag aaa gta ttt att ttt tct gga aca ttt aga aaa aac ttg gat      3819
Pro Gln Lys Val Phe Ile Phe Ser Gly Thr Phe Arg Lys Asn Leu Asp
    1215                1220                1225 ccc tat gaa cag tgg agt gat caa gaa ata tgg aaa gtt gca gat gag      3867
Pro Tyr Glu Gln Trp Ser Asp Gln Glu Ile Trp Lys Val Ala Asp Glu
1230                1235                1240                1245 gtt ggg ctc aga tct gtg ata gaa cag ttt cct ggg aag ctt gac ttt      3915
Val Gly Leu Arg Ser Val Ile Glu Gln Phe Pro Gly Lys Leu Asp Phe
                1250                1255                1260 gtc ctt gtg gat ggg ggc tgt gtc cta agc cat ggc cac aag cag ttg      3963
Val Leu Val Asp Gly Gly Cys Val Leu Ser His Gly His Lys Gln Leu
            1265                1270                1275 atg tgc ttg gct aga tct gtt ctc agt aag gcg aag atc ttg ctg ctt      4011
Met Cys Leu Ala Arg Ser Val Leu Ser Lys Ala Lys Ile Leu Leu Leu
        1280                1285                1290 gat gaa ccc agt gct cat ttg gat cca gta aca tac caa ata att aga      4059
Asp Glu Pro Ser Ala His Leu Asp Pro Val Thr Tyr Gln Ile Ile Arg
    1295                1300                1305 aga act cta aaa caa gca ttt gct gat tgc aca gta att ctc tgt gaa      4107
Arg Thr Leu Lys Gln Ala Phe Ala Asp Cys Thr Val Ile Leu Cys Glu
1310                1315                1320                1325 cac agg ata gaa gca atg ctg gaa tgc caa caa ttt ttg gtc ata gaa      4155
His Arg Ile Glu Ala Met Leu Glu Cys Gln Gln Phe Leu Val Ile Glu
                1330                1335                1340 gag aac aaa gtg cgg cag tac gat tcc atc cag aaa ctg ctg aac gag      4203
Glu Asn Lys Val Arg Gln Tyr Asp Ser Ile Gln Lys Leu Leu Asn Glu
            1345                1350                1355 agg agc ctc ttc cgg caa gcc atc agc ccc tcc gac agg gtg aag ctc      4251
Arg Ser Leu Phe Arg Gln Ala Ile Ser Pro Ser Asp Arg Val Lys Leu
        1360                1365                1370 ttt ccc cac cgg aac tca agc aag tgc aag tct aag ccc cag att gct      4299
Phe Pro His Arg Asn Ser Ser Lys Cys Lys Ser Lys Pro Gln Ile Ala
    1375                1380                1385 gct ctg aaa gag gag aca gaa gaa gag gtg caa gat aca agg ctt tag      4347
Ala Leu Lys Glu Glu Thr Glu Glu Glu Val Gln Asp Thr Arg Leu  *
1390                1395                1400

<210> SEQ ID NO 7
<211> LENGTH: 4347
<212> TYPE: DNA
<213> ORGANISM: homo sapiens
<220> FEATURE:
<221> NAME/KEY: CDS
<222> LOCATION: (133)...(4347)

<400> SEQUENCE: 7
aattggaagc aaatgacatc acagcaggtc agagaaaaag ggttgagcgg caggcaccca      60
gagtagtagg tctttggcat taggagcttg agcccagacg gccctagcag ggaccccagc     120
gcccgagaga cc atg cag agg tcg cct ctg gaa aag gcc agc gtt gtc tcc     171
           Met Gln Arg Ser Pro Leu Glu Lys Ala Ser Val Val Ser
             1               5                  10 aaa ctt ttt ttc agc tgg acc aga cca att ttg agg aaa gga tac aga      219
Lys Leu Phe Phe Ser Trp Thr Arg Pro Ile Leu Arg Lys Gly Tyr Arg
     15                  20                  25 cag cgc ctg gaa ttg tca gac ata tac caa atc cct tct gtt gat tct      267
Gln Arg Leu Glu Leu Ser Asp Ile Tyr Gln Ile Pro Ser Val Asp Ser
 30                  35                  40                  45 gct gac aat cta tct gaa aaa ttg gaa aga gaa tgg gat aga gag ctg      315
Ala Asp Asn Leu Ser Glu Lys Leu Glu Arg Glu Trp Asp Arg Glu Leu
             50                  55                  60
```

-continued

```
gct tca aag aaa aat cct aaa ctc att aat gcc ctt cgg cga tgt ttt       363
Ala Ser Lys Lys Asn Pro Lys Leu Ile Asn Ala Leu Arg Arg Cys Phe
         65                  70                  75 ttc tgg aga ttt atg ttc tat gga atc ttt tta tat tta ggg gaa gtc       411
Phe Trp Arg Phe Met Phe Tyr Gly Ile Phe Leu Tyr Leu Gly Glu Val
     80                  85                  90 acc aaa gca gta cag cct ctc tta ctg gga aga atc ata gct tcc tat       459
Thr Lys Ala Val Gln Pro Leu Leu Leu Gly Arg Ile Ile Ala Ser Tyr
 95                 100                 105 gac ccg gat aac aag gag gaa cgc tct atc gcg att tat cta ggc ata       507
Asp Pro Asp Asn Lys Glu Glu Arg Ser Ile Ala Ile Tyr Leu Gly Ile
110                 115                 120                 125 ggc tta tgc ctt ctc ttt att gtg agg aca ctg ctc cta cac cca gcc       555
Gly Leu Cys Leu Leu Phe Ile Val Arg Thr Leu Leu Leu His Pro Ala
             130                 135                 140 att ttt ggc ctt cat cac att gga atg cag atg aga ata gct atg ttt       603
Ile Phe Gly Leu His His Ile Gly Met Gln Met Arg Ile Ala Met Phe
                 145                 150                 155 agt ttg att tat aag aag act tta aag ctg tca agc cgt gtt cta gat       651
Ser Leu Ile Tyr Lys Lys Thr Leu Lys Leu Ser Ser Arg Val Leu Asp
         160                 165                 170 aaa ata agt att gga caa ctt gtt agt ctc ctt tcc aac aac ctg aac       699
Lys Ile Ser Ile Gly Gln Leu Val Ser Leu Leu Ser Asn Asn Leu Asn
     175                 180                 185 aaa ttt gat gaa gga ctt gca ttg gca cat ttc gtg tgg atc gct cct       747
Lys Phe Asp Glu Gly Leu Ala Leu Ala His Phe Val Trp Ile Ala Pro
190                 195                 200                 205 ttg caa gtg gca ctc ctc atg ggg cta atc tgg gag ttg tta cag gcg       795
Leu Gln Val Ala Leu Leu Met Gly Leu Ile Trp Glu Leu Leu Gln Ala
             210                 215                 220 tct gcc ttc tgt gga ctt ggt ttc ctg ata gtc ctt gcc ctt ttt cag       843
Ser Ala Phe Cys Gly Leu Gly Phe Leu Ile Val Leu Ala Leu Phe Gln
                 225                 230                 235 gct ggg cta ggg aga atg atg atg aag tac aga gat cag aga gct ggg       891
Ala Gly Leu Gly Arg Met Met Met Lys Tyr Arg Asp Gln Arg Ala Gly
         240                 245                 250 aag atc agt gaa aga ctt gtg att acc tca gaa atg att gaa aat atc       939
Lys Ile Ser Glu Arg Leu Val Ile Thr Ser Glu Met Ile Glu Asn Ile
     255                 260                 265 caa tct gtt aag gca tac tgc tgg gaa gaa gca atg gaa aaa atg att       987
Gln Ser Val Lys Ala Tyr Cys Trp Glu Glu Ala Met Glu Lys Met Ile
270                 275                 280                 285 gaa aac tta aga caa aca gaa ctg aaa ctg act cgg aag gca gcc tat      1035
Glu Asn Leu Arg Gln Thr Glu Leu Lys Leu Thr Arg Lys Ala Ala Tyr
             290                 295                 300 gtg aga tac ttc aat agc tca gcc ttc ttc tca ggg ttc ttt gtg           1083
Val Arg Tyr Phe Asn Ser Ser Ala Phe Phe Ser Gly Phe Phe Val
                 305                 310                 315 gtg ttt tta tct gtg ctt ccc tat gca cta atc aaa gga atc atc ctc      1131
Val Phe Leu Ser Val Leu Pro Tyr Ala Leu Ile Lys Gly Ile Ile Leu
         320                 325                 330 cgg aaa ata ttc acc acc atc tca ttc tgc att gtt ctg cgc atg gcg      1179
Arg Lys Ile Phe Thr Thr Ile Ser Phe Cys Ile Val Leu Arg Met Ala
     335                 340                 345 gtc act cgg caa ttt ccc tgg gct gta caa aca tgg tat gac tct ctt      1227
Val Thr Arg Gln Phe Pro Trp Ala Val Gln Thr Trp Tyr Asp Ser Leu
350                 355                 360                 365 gga gca ata aac aaa ata cag gat ttc tta caa aag caa gaa tat aag      1275
Gly Ala Ile Asn Lys Ile Gln Asp Phe Leu Gln Lys Gln Glu Tyr Lys
             370                 375                 380
```

-continued

```
aca ttg gaa tat aac tta acg act aca gaa gta gtg atg gag aat gta      1323
Thr Leu Glu Tyr Asn Leu Thr Thr Thr Glu Val Val Met Glu Asn Val
            385                 390                 395 aca gcc ttc tgg gag gag gga ttt ggg gaa tta ttt gag aaa gca aaa      1371
Thr Ala Phe Trp Glu Glu Gly Phe Gly Glu Leu Phe Glu Lys Ala Lys
    400                 405                 410 caa aac aat aac aat aga aaa act tct aat ggt gat gac agc ctc ttc      1419
Gln Asn Asn Asn Asn Arg Lys Thr Ser Asn Gly Asp Asp Ser Leu Phe
415                 420                 425 ttc agt aat ttc tca ctt ctt ggt act cct gtc ctg aaa gat att aat      1467
Phe Ser Asn Phe Ser Leu Leu Gly Thr Pro Val Leu Lys Asp Ile Asn
430                 435                 440                 445 ttc aag ata gaa aga gga cag ttg ttg gcg gtt gct gga tcc act gga      1515
Phe Lys Ile Glu Arg Gly Gln Leu Leu Ala Val Ala Gly Ser Thr Gly
                450                 455                 460 gca ggc aag act tca ctt cta atg atg att atg gga gaa ctg gag cct      1563
Ala Gly Lys Thr Ser Leu Leu Met Met Ile Met Gly Glu Leu Glu Pro
            465                 470                 475 tca gag ggt aaa att aag cac agt gga aga att tca ttc tgt tct cag      1611
Ser Glu Gly Lys Ile Lys His Ser Gly Arg Ile Ser Phe Cys Ser Gln
        480                 485                 490 ttt tcc tgg att atg cct ggc acc att aaa gaa aat atc atc ttt ggt      1659
Phe Ser Trp Ile Met Pro Gly Thr Ile Lys Glu Asn Ile Ile Phe Gly
    495                 500                 505 gtt tcc tat gat gaa tat aga tac aga agc gtc atc aaa gca tgc caa      1707
Val Ser Tyr Asp Glu Tyr Arg Tyr Arg Ser Val Ile Lys Ala Cys Gln
510                 515                 520                 525 cta gaa gag gac atc tcc aag ttt gca gag aaa gac aat ata gtt ctt      1755
Leu Glu Glu Asp Ile Ser Lys Phe Ala Glu Lys Asp Asn Ile Val Leu
                530                 535                 540 gga gaa ggt gga atc aca ctg agt gga ggt caa cga gca aga att tct      1803
Gly Glu Gly Gly Ile Thr Leu Ser Gly Gly Gln Arg Ala Arg Ile Ser
            545                 550                 555 tta gca aga gca gta tac aaa gat gct gat ttg tat tta tta gac tct      1851
Leu Ala Arg Ala Val Tyr Lys Asp Ala Asp Leu Tyr Leu Leu Asp Ser
        560                 565                 570 cct ttt gga tac cta gat gtt tta aca gaa aaa gaa ata ttt gaa agc      1899
Pro Phe Gly Tyr Leu Asp Val Leu Thr Glu Lys Glu Ile Phe Glu Ser
    575                 580                 585 tgt gtc tgt aaa ctg atg gct aac aaa act agg att ttg gtc act tct      1947
Cys Val Cys Lys Leu Met Ala Asn Lys Thr Arg Ile Leu Val Thr Ser
590                 595                 600                 605 aaa atg gaa cat tta aag aaa gct gac aaa ata tta att ttg cat gaa      1995
Lys Met Glu His Leu Lys Lys Ala Asp Lys Ile Leu Ile Leu His Glu
                610                 615                 620 ggt agc agc tat ttt tat ggg aca ttt tca gaa ctc caa aat cta cag      2043
Gly Ser Ser Tyr Phe Tyr Gly Thr Phe Ser Glu Leu Gln Asn Leu Gln
            625                 630                 635 cca gac ttt agc tca aaa ctc atg gga tgt gat tct ttc gac caa ttt      2091
Pro Asp Phe Ser Ser Lys Leu Met Gly Cys Asp Ser Phe Asp Gln Phe
        640                 645                 650 agt gca gaa aga aga aat tca atc cta act gag acc tta cac cgt ttc      2139
Ser Ala Glu Arg Arg Asn Ser Ile Leu Thr Glu Thr Leu His Arg Phe
    655                 660                 665 tca tta gaa gga gat gct cct gtc tcc tgg aca gaa aca aaa aaa caa      2187
Ser Leu Glu Gly Asp Ala Pro Val Ser Trp Thr Glu Thr Lys Lys Gln
670                 675                 680                 685 tct ttt aaa cag act gga gag ttt ggg gaa aaa agg aag aat tct att      2235
Ser Phe Lys Gln Thr Gly Glu Phe Gly Glu Lys Arg Lys Asn Ser Ile
```

-continued

|  |  |  |  |  |
|---|---|---|---|---|
| | 690 | 695 | 700 | |
| ctc aat cca atc aac tct cac cga aag aca aca gca tcc aca cga aaa<br>Leu Asn Pro Ile Asn Ser His Arg Lys Thr Thr Ala Ser Thr Arg Lys<br>705                710                715 | | | | 2283 |
| gtg tca ctg gcc cct cag gca aac ttg act gaa ctg gat ata tat tca<br>Val Ser Leu Ala Pro Gln Ala Asn Leu Thr Glu Leu Asp Ile Tyr Ser<br>    720                725                730 | | | | 2331 |
| aga agg tta tct caa gaa act ggc ttg gaa ata agt gaa gaa att aac<br>Arg Arg Leu Ser Gln Glu Thr Gly Leu Glu Ile Ser Glu Glu Ile Asn<br>735                740              745 | | | | 2379 |
| gaa gaa gac tta aag gag tgc ttt ttt gat gat atg gag agc ata cca<br>Glu Glu Asp Leu Lys Glu Cys Phe Phe Asp Asp Met Glu Ser Ile Pro<br>750                755              760              765 | | | | 2427 |
| gca gtg act aca tgg aac aca tac ctt cga tat att act gtc cac aag<br>Ala Val Thr Thr Trp Asn Thr Tyr Leu Arg Tyr Ile Thr Val His Lys<br>           770                775              780 | | | | 2475 |
| agc tta att ttt gtg cta att tgg tgc tta gta att ttt ctg gca gag<br>Ser Leu Ile Phe Val Leu Ile Trp Cys Leu Val Ile Phe Leu Ala Glu<br>                785              790              795 | | | | 2523 |
| gtg gct gct tct ttg gtt gtg ctg tgg ctc ctt gga aac act cct ctt<br>Val Ala Ala Ser Leu Val Val Leu Trp Leu Leu Gly Asn Thr Pro Leu<br>800                805              810 | | | | 2571 |
| caa gac aaa ggg aat agt act cat agt aga aat aac agc tat gca gtg<br>Gln Asp Lys Gly Asn Ser Thr His Ser Arg Asn Asn Ser Tyr Ala Val<br>815                820              825 | | | | 2619 |
| att atc acc agc acc agt tcg tat tat gtg ttt tac att tac gtg gga<br>Ile Ile Thr Ser Thr Ser Ser Tyr Tyr Val Phe Tyr Ile Tyr Val Gly<br>830                835              840              845 | | | | 2667 |
| gta gcc gac act ttg ctt gct atg gga ttc ttc aga ggt cta cca ctg<br>Val Ala Asp Thr Leu Leu Ala Met Gly Phe Phe Arg Gly Leu Pro Leu<br>           850                855              860 | | | | 2715 |
| gtg cat act cta atc aca gtg tcg aaa att tta cac cac aaa atg tta<br>Val His Thr Leu Ile Thr Val Ser Lys Ile Leu His His Lys Met Leu<br>                865              870              875 | | | | 2763 |
| cat tct gtt ctt caa gca cct atg tca acc ctc aac acg ttg aaa gca<br>His Ser Val Leu Gln Ala Pro Met Ser Thr Leu Asn Thr Leu Lys Ala<br>880                885              890 | | | | 2811 |
| ggt ggg att ctt aat aga ttc tcc aaa gat ata gca att ttg gat gac<br>Gly Gly Ile Leu Asn Arg Phe Ser Lys Asp Ile Ala Ile Leu Asp Asp<br>895                900              905 | | | | 2859 |
| ctt ctg cct ctt acc ata ttt gac ttc atc cag ttg tta tta att gtg<br>Leu Leu Pro Leu Thr Ile Phe Asp Phe Ile Gln Leu Leu Leu Ile Val<br>910                915              920              925 | | | | 2907 |
| att gga gct ata gca gtt gtc gca gtt tta caa ccc tac atc ttt gtt<br>Ile Gly Ala Ile Ala Val Val Ala Val Leu Gln Pro Tyr Ile Phe Val<br>           930                935              940 | | | | 2955 |
| gca aca gtg cca gtg ata gtg gct ttt att atg ttg aga gca tat ttc<br>Ala Thr Val Pro Val Ile Val Ala Phe Ile Met Leu Arg Ala Tyr Phe<br>945                950              955 | | | | 3003 |
| ctc caa acc tca cag caa ctc aaa caa ctg gaa tct gaa ggc agg agt<br>Leu Gln Thr Ser Gln Gln Leu Lys Gln Leu Glu Ser Glu Gly Arg Ser<br>           960                965              970 | | | | 3051 |
| cca att ttc act cat ctt gtt aca agc tta aaa gga cta tgg aca ctt<br>Pro Ile Phe Thr His Leu Val Thr Ser Leu Lys Gly Leu Trp Thr Leu<br>975                980              985 | | | | 3099 |
| cgt gcc ttc gga cgg cag cct tac ttt gaa act ctg ttc cac aaa gct<br>Arg Ala Phe Gly Arg Gln Pro Tyr Phe Glu Thr Leu Phe His Lys Ala<br>990                995              1000           1005 | | | | 3147 |
| ctg aat tta cat act gcc aac tgg ttc ttg tac ctg tca aca ctg cgc | | | | 3195 |

```
                                     -continued

Leu Asn Leu His Thr Ala Asn Trp Phe Leu Tyr Leu Ser Thr Leu Arg
            1010                1015                1020 tgg ttc caa atg aga ata gaa atg att ttt gtc atc ttc ttc att gct      3243
Trp Phe Gln Met Arg Ile Glu Met Ile Phe Val Ile Phe Phe Ile Ala
            1025                1030                1035 gtt acc ttc att tcc att tta aca aca gga gaa gga gaa gga aga gtt      3291
Val Thr Phe Ile Ser Ile Leu Thr Thr Gly Glu Gly Glu Gly Arg Val
            1040                1045                1050 ggt att atc ctg act tta gcc atg aat atc atg agt aca ttg cag tgg      3339
Gly Ile Ile Leu Thr Leu Ala Met Asn Ile Met Ser Thr Leu Gln Trp
            1055                1060                1065 gct gta aac tcc agc ata gat gtg gat agc ttg atg cga tct gtg agc      3387
Ala Val Asn Ser Ser Ile Asp Val Asp Ser Leu Met Arg Ser Val Ser
1070                1075                1080                1085 cga gtc ttt aag ttc att gac atg cca aca gaa ggt aaa cct acc aag      3435
Arg Val Phe Lys Phe Ile Asp Met Pro Thr Glu Gly Lys Pro Thr Lys
                1090                1095                1100 tca acc aaa cca tac aag aat ggc caa ctc tcg aaa gtt atg att att      3483
Ser Thr Lys Pro Tyr Lys Asn Gly Gln Leu Ser Lys Val Met Ile Ile
            1105                1110                1115 gag aat tca cac gtg aag aaa gat gac atc tgg ccc tca ggg ggc caa      3531
Glu Asn Ser His Val Lys Lys Asp Asp Ile Trp Pro Ser Gly Gly Gln
            1120                1125                1130 atg act gtc aaa gat ctc aca gca aaa tac aca gaa ggt gga aat gcc      3579
Met Thr Val Lys Asp Leu Thr Ala Lys Tyr Thr Glu Gly Gly Asn Ala
            1135                1140                1145 ata tta gag aac att tcc ttc tca ata agt cct ggc cag agg gtg ggc      3627
Ile Leu Glu Asn Ile Ser Phe Ser Ile Ser Pro Gly Gln Arg Val Gly
1150                1155                1160                1165 ctc ttg gga aga act gga tca ggg aag agt act ttg tta tca gct ttt      3675
Leu Leu Gly Arg Thr Gly Ser Gly Lys Ser Thr Leu Leu Ser Ala Phe
                1170                1175                1180 ttg aga cta ctg aac act gaa gga gaa atc cag atc gat ggt gtg tct      3723
Leu Arg Leu Leu Asn Thr Glu Gly Glu Ile Gln Ile Asp Gly Val Ser
            1185                1190                1195 tgg gat tca ata act ttg caa cag tgg agg aaa gcc ttt gga gtg ata      3771
Trp Asp Ser Ile Thr Leu Gln Gln Trp Arg Lys Ala Phe Gly Val Ile
            1200                1205                1210 cca cag aaa gta ttt att ttt tct gga aca ttt aga aaa aac ttg gat      3819
Pro Gln Lys Val Phe Ile Phe Ser Gly Thr Phe Arg Lys Asn Leu Asp
            1215                1220                1225 ccc tat gaa cag tgg agt gat caa gaa ata tgg aaa gtt gca gat gag      3867
Pro Tyr Glu Gln Trp Ser Asp Gln Glu Ile Trp Lys Val Ala Asp Glu
1230                1235                1240                1245 gtt ggg ctc aga tct gtg ata gaa cag ttt cct ggg aag ctt gac ttt      3915
Val Gly Leu Arg Ser Val Ile Glu Gln Phe Pro Gly Lys Leu Asp Phe
            1250                1255                1260 gtc ctt gtg gat ggg ggc tgt gtc cta agc cat ggc cac aag cag ttg      3963
Val Leu Val Asp Gly Gly Cys Val Leu Ser His Gly His Lys Gln Leu
            1265                1270                1275 atg tgc ttg gct aga tct gtt ctc agt aag gcg aag atc ttg ctg ctt      4011
Met Cys Leu Ala Arg Ser Val Leu Ser Lys Ala Lys Ile Leu Leu Leu
            1280                1285                1290 gat gaa ccc agt gct cat ttg gat cca gta aca tac caa ata att aga      4059
Asp Glu Pro Ser Ala His Leu Asp Pro Val Thr Tyr Gln Ile Ile Arg
            1295                1300                1305 aga act cta aaa caa gca ttt gct gat tgc aca gta att ctc tgt gaa      4107
Arg Thr Leu Lys Gln Ala Phe Ala Asp Cys Thr Val Ile Leu Cys Glu
1310                1315                1320                1325
```

```
cac agg ata gaa gca atg ctg gaa tgc caa caa ttt ttg gtc ata gaa         4155
His Arg Ile Glu Ala Met Leu Glu Cys Gln Gln Phe Leu Val Ile Glu
            1330                1335                1340 gag aac aaa gtg cgg cag tac gat tcc atc cag aaa ctg ctg aac gag         4203
Glu Asn Lys Val Arg Gln Tyr Asp Ser Ile Gln Lys Leu Leu Asn Glu
        1345                1350                1355 agg agc ctc ttc cgg caa gcc atc agc ccc tcc gac agg gtg aag ctc         4251
Arg Ser Leu Phe Arg Gln Ala Ile Ser Pro Ser Asp Arg Val Lys Leu
    1360                1365                1370 ttt ccc cac cgg aac tca agc aag tgc aag tct aag ccc cag att gct         4299
Phe Pro His Arg Asn Ser Ser Lys Cys Lys Ser Lys Pro Gln Ile Ala
1375                1380                1385 gct ctg aaa gag gag aca gaa gaa gag gtg caa gat aca agg ctt tag         4347
Ala Leu Lys Glu Glu Thr Glu Glu Glu Val Gln Asp Thr Arg Leu *
            1390                1395                1400

<210> SEQ ID NO 8
<211> LENGTH: 4311
<212> TYPE: DNA
<213> ORGANISM: homo sapiens
<220> FEATURE:
<221> NAME/KEY: CDS
<222> LOCATION: (133)...(4311)

<400> SEQUENCE: 8
aattggaagc aaatgacatc acagcaggtc agagaaaaag ggttgagcgg caggcaccca        60
gagtagtagg tctttggcat taggagcttg agcccagacg gccctagcag ggaccccagc       120
gcccgagaga cc atg cag agg tcg cct ctg gaa aag gcc agc gtt gtc tcc       171
              Met Gln Arg Ser Pro Leu Glu Lys Ala Ser Val Val Ser
                1               5                   10 aaa ctt ttt ttc agc tgg acc aga cca att ttg agg aaa gga tac aga         219
Lys Leu Phe Phe Ser Trp Thr Arg Pro Ile Leu Arg Lys Gly Tyr Arg
            15                  20                  25 cag cgc ctg gaa ttg tca gac ata tac caa atc cct tct gtt gat tct         267
Gln Arg Leu Glu Leu Ser Asp Ile Tyr Gln Ile Pro Ser Val Asp Ser
30                  35                  40                  45 gct gac aat cta tct gaa aaa ttg gaa aga gaa tgg gat aga gag ctg         315
Ala Asp Asn Leu Ser Glu Lys Leu Glu Arg Glu Trp Asp Arg Glu Leu
                50                  55                  60 gct tca aag aaa aat cct aaa ctc att aat gcc ctt cgg cga tgt ttt         363
Ala Ser Lys Lys Asn Pro Lys Leu Ile Asn Ala Leu Arg Arg Cys Phe
            65                  70                  75 ttc tgg aga ttt atg ttc tat gga atc ttt tta tat tta ggg gaa gtc         411
Phe Trp Arg Phe Met Phe Tyr Gly Ile Phe Leu Tyr Leu Gly Glu Val
        80                  85                  90 acc aaa gca gta cag cct ctc tta ctg gga aga atc ata gct tcc tat         459
Thr Lys Ala Val Gln Pro Leu Leu Leu Gly Arg Ile Ile Ala Ser Tyr
    95                  100                 105 gac ccg gat aac aag gag gaa cgc tct atc gcg att tat cta ggc ata         507
Asp Pro Asp Asn Lys Glu Glu Arg Ser Ile Ala Ile Tyr Leu Gly Ile
110                 115                 120                 125 ggc tta tgc ctt ctc ttt att gtg agg aca ctg ctc cta cac cca gcc         555
Gly Leu Cys Leu Leu Phe Ile Val Arg Thr Leu Leu Leu His Pro Ala
                130                 135                 140 att ttt ggc ctt cat cac att gga atg cag atg aga ata gct atg ttt         603
Ile Phe Gly Leu His His Ile Gly Met Gln Met Arg Ile Ala Met Phe
            145                 150                 155 agt ttg att tat aag aag act tta aag ctg tca agc cgt gtt cta gat         651
Ser Leu Ile Tyr Lys Lys Thr Leu Lys Leu Ser Ser Arg Val Leu Asp
        160                 165                 170
```

```
aaa ata agt att gga caa ctt gtt agt ctc ctt tcc aac aac ctg aac      699
Lys Ile Ser Ile Gly Gln Leu Val Ser Leu Leu Ser Asn Asn Leu Asn
    175                 180                 185 aaa ttt gat gaa gga ctt gca ttg gca cat ttc gtg tgg atc gct cct      747
Lys Phe Asp Glu Gly Leu Ala Leu Ala His Phe Val Trp Ile Ala Pro
190                 195                 200                 205 ttg caa gtg gca ctc ctc atg ggg cta atc tgg gag ttg tta cag gcg      795
Leu Gln Val Ala Leu Leu Met Gly Leu Ile Trp Glu Leu Leu Gln Ala
                210                 215                 220 tct gcc ttc tgt gga ctt ggt ttc ctg ata gtc ctt gcc ctt ttt cag      843
Ser Ala Phe Cys Gly Leu Gly Phe Leu Ile Val Leu Ala Leu Phe Gln
            225                 230                 235 gct ggg cta ggg aga atg atg atg aag tac aga gat cag aga gct ggg      891
Ala Gly Leu Gly Arg Met Met Met Lys Tyr Arg Asp Gln Arg Ala Gly
        240                 245                 250 aag atc agt gaa aga ctt gtg att acc tca gaa atg att gaa aat atc      939
Lys Ile Ser Glu Arg Leu Val Ile Thr Ser Glu Met Ile Glu Asn Ile
    255                 260                 265 caa tct gtt aag gca tac tgc tgg gaa gaa gca atg gaa aaa atg att      987
Gln Ser Val Lys Ala Tyr Cys Trp Glu Glu Ala Met Glu Lys Met Ile
270                 275                 280                 285 gaa aac tta aga caa aca gaa ctg aaa ctg act cgg aag gca gcc tat     1035
Glu Asn Leu Arg Gln Thr Glu Leu Lys Leu Thr Arg Lys Ala Ala Tyr
                290                 295                 300 gtg aga tac ttc aat agc tca gcc ttc ttc ttc tca ggg ttc ttt gtg     1083
Val Arg Tyr Phe Asn Ser Ser Ala Phe Phe Phe Ser Gly Phe Phe Val
            305                 310                 315 gtg ttt tta tct gtg ctt ccc tat gca cta atc aaa gga atc atc ctc     1131
Val Phe Leu Ser Val Leu Pro Tyr Ala Leu Ile Lys Gly Ile Ile Leu
        320                 325                 330 cgg aaa ata ttc acc acc atc tca ttc tgc att gtt ctg cgc atg gcg     1179
Arg Lys Ile Phe Thr Thr Ile Ser Phe Cys Ile Val Leu Arg Met Ala
    335                 340                 345 gtc act cgg caa ttt ccc tgg gct gta caa aca tgg tat gac tct ctt     1227
Val Thr Arg Gln Phe Pro Trp Ala Val Gln Thr Trp Tyr Asp Ser Leu
350                 355                 360                 365 gga gca ata aac aaa ata cag gat ttc tta caa aag caa gaa tat aag     1275
Gly Ala Ile Asn Lys Ile Gln Asp Phe Leu Gln Lys Gln Glu Tyr Lys
                370                 375                 380 aca ttg gaa tat aac tta acg act aca gaa gta gtg atg gag aat gta     1323
Thr Leu Glu Tyr Asn Leu Thr Thr Thr Glu Val Val Met Glu Asn Val
            385                 390                 395 aca gcc ttc tgg gag gag gga ttt ggg gaa tta ttt gag aaa gca aaa     1371
Thr Ala Phe Trp Glu Glu Gly Phe Gly Glu Leu Phe Glu Lys Ala Lys
        400                 405                 410 caa aac aat aac aat aga aaa act tct aat ggt gat gac agc ctc ttc     1419
Gln Asn Asn Asn Asn Arg Lys Thr Ser Asn Gly Asp Asp Ser Leu Phe
    415                 420                 425 ttc agt aat ttc tca ctt ctt ggt act cct gtc ctg aaa gat att aat     1467
Phe Ser Asn Phe Ser Leu Leu Gly Thr Pro Val Leu Lys Asp Ile Asn
430                 435                 440                 445 ttc aag ata gaa aga gga cag ttg ttg gcg gtt gct gga tcc act gga     1515
Phe Lys Ile Glu Arg Gly Gln Leu Leu Ala Val Ala Gly Ser Thr Gly
                450                 455                 460 gca ggc aag act tca ctt cta atg atg att atg gga gaa ctg gag cct     1563
Ala Gly Lys Thr Ser Leu Leu Met Met Ile Met Gly Glu Leu Glu Pro
            465                 470                 475 tca gag ggt aaa att aag cac agt gga aga att tca ttc tgt tct cag     1611
Ser Glu Gly Lys Ile Lys His Ser Gly Arg Ile Ser Phe Cys Ser Gln
        480                 485                 490
```

-continued

| | | |
|---|---|---|
| ttt tcc tgg att atg cct ggc acc att aaa gaa aat atc atc ttt ggt<br>Phe Ser Trp Ile Met Pro Gly Thr Ile Lys Glu Asn Ile Ile Phe Gly<br>    495                              500                          505 | 1659 | |
| gtt tcc tat gat gaa tat aga tac aga agc gtc atc aaa gca tgc caa<br>Val Ser Tyr Asp Glu Tyr Arg Tyr Arg Ser Val Ile Lys Ala Cys Gln<br>510                         515                        520                        525 | 1707 | |
| cta gaa gag gac atc tcc aag ttt gca gag aaa gac aat ata gtt ctt<br>Leu Glu Glu Asp Ile Ser Lys Phe Ala Glu Lys Asp Asn Ile Val Leu<br>                              530                        535                        540 | 1755 | |
| gga gaa ggt gga atc aca ctg agt gga ggt caa cga gca aga att tct<br>Gly Glu Gly Gly Ile Thr Leu Ser Gly Gly Gln Arg Ala Arg Ile Ser<br>             545                        550                        555 | 1803 | |
| tta gca aga gca gta tac aaa gat gct gat ttg tat tta tta gac tct<br>Leu Ala Arg Ala Val Tyr Lys Asp Ala Asp Leu Tyr Leu Leu Asp Ser<br>                  560                        565                        570 | 1851 | |
| cct ttt gga tac cta gat gtt tta aca gaa aaa gaa ata ttt gaa agc<br>Pro Phe Gly Tyr Leu Asp Val Leu Thr Glu Lys Glu Ile Phe Glu Ser<br>             575                        580                        585 | 1899 | |
| tgt gtc tgt aaa ctg atg gct aac aaa act agg att ttg gtc act tct<br>Cys Val Cys Lys Leu Met Ala Asn Lys Thr Arg Ile Leu Val Thr Ser<br>590                       595                        600                        605 | 1947 | |
| aaa atg gaa cat tta aag aaa gct gac aaa ata tta att ttg cat gaa<br>Lys Met Glu His Leu Lys Lys Ala Asp Lys Ile Leu Ile Leu His Glu<br>                  610                        615                        620 | 1995 | |
| ggt agc agc tat ttt tat ggg aca ttt tca gaa ctc caa aat cta cag<br>Gly Ser Ser Tyr Phe Tyr Gly Thr Phe Ser Glu Leu Gln Asn Leu Gln<br>             625                        630                        635 | 2043 | |
| cca gac ttt agc tca aaa ctc atg gga tgt gat tct ttc gac caa ttt<br>Pro Asp Phe Ser Ser Lys Leu Met Gly Cys Asp Ser Phe Asp Gln Phe<br>                  640                        645                        650 | 2091 | |
| agt gca gaa aga aga aat tca atc cta act gag acc tta cac cgt ttc<br>Ser Ala Glu Arg Arg Asn Ser Ile Leu Thr Glu Thr Leu His Arg Phe<br>655                       660                        665 | 2139 | |
| tca tta gaa gga gat gct cct gtc tcc tgg aca gaa aca aaa aaa caa<br>Ser Leu Glu Gly Asp Ala Pro Val Ser Trp Thr Glu Thr Lys Lys Gln<br>670                       675                        680                        685 | 2187 | |
| tct ttt aaa cag act gga gag ttt ggg gaa aaa agg aag aat tct att<br>Ser Phe Lys Gln Thr Gly Glu Phe Gly Glu Lys Arg Lys Asn Ser Ile<br>                  690                        695                        700 | 2235 | |
| ctc aat cca atc aac tct cac cga aag aca aca gca tcc aca cga aaa<br>Leu Asn Pro Ile Asn Ser His Arg Lys Thr Thr Ala Ser Thr Arg Lys<br>             705                        710                        715 | 2283 | |
| gtg tca ctg gcc cct cag gca aac ttg act gaa ctg gat ata tat tca<br>Val Ser Leu Ala Pro Gln Ala Asn Leu Thr Glu Leu Asp Ile Tyr Ser<br>                  720                        725                        730 | 2331 | |
| aga agg tta tct caa gaa act ggc ttg gaa ata agt gaa gaa gat atg<br>Arg Arg Leu Ser Gln Glu Thr Gly Leu Glu Ile Ser Glu Glu Asp Met<br>735                       740                        745 | 2379 | |
| gag agc ata cca gca gtg act aca tgg aac aca tac ctt cga tat att<br>Glu Ser Ile Pro Ala Val Thr Thr Trp Asn Thr Tyr Leu Arg Tyr Ile<br>750                       755                        760                        765 | 2427 | |
| act gtc cac aag agc tta att ttt gtg cta att tgg tgc tta gta att<br>Thr Val His Lys Ser Leu Ile Phe Val Leu Ile Trp Cys Leu Val Ile<br>                  770                        775                        780 | 2475 | |
| ttt ctg gca gag gtg gct gct tct ttg gtt gtg ctg tgg ctc ctt gga<br>Phe Leu Ala Glu Val Ala Ala Ser Leu Val Val Leu Trp Leu Leu Gly<br>             785                        790                        795 | 2523 | |
| aac act cct ctt caa gac aaa ggg aat agt act cat agt aga aat aac<br>Asn Thr Pro Leu Gln Asp Lys Gly Asn Ser Thr His Ser Arg Asn Asn | 2571 | |

```
                 800             805             810
agc tat gca gtg att atc acc agc acc agt tcg tat tat gtg ttt tac    2619
Ser Tyr Ala Val Ile Ile Thr Ser Thr Ser Ser Tyr Tyr Val Phe Tyr
    815                 820                 825 att tac gtg gga gta gcc gac act ttg ctt gct atg gga ttc ttc aga    2667
Ile Tyr Val Gly Val Ala Asp Thr Leu Leu Ala Met Gly Phe Phe Arg
830                 835                 840                 845 ggt cta cca ctg gtg cat act cta atc aca gtg tcg aaa att tta cac    2715
Gly Leu Pro Leu Val His Thr Leu Ile Thr Val Ser Lys Ile Leu His
                850                 855                 860 cac aaa atg tta cat tct gtt ctt caa gca cct atg tca acc ctc aac    2763
His Lys Met Leu His Ser Val Leu Gln Ala Pro Met Ser Thr Leu Asn
            865                 870                 875 acg ttg aaa gca ggt ggg att ctt aat aga ttc tcc aaa gat ata gca    2811
Thr Leu Lys Ala Gly Gly Ile Leu Asn Arg Phe Ser Lys Asp Ile Ala
        880                 885                 890 att ttg gat gac ctt ctg cct ctt acc ata ttt gac ttc atc cag ttg    2859
Ile Leu Asp Asp Leu Leu Pro Leu Thr Ile Phe Asp Phe Ile Gln Leu
    895                 900                 905 tta tta att gtg att gga gct ata gca gtt gtc gca gtt tta caa ccc    2907
Leu Leu Ile Val Ile Gly Ala Ile Ala Val Val Ala Val Leu Gln Pro
910                 915                 920                 925 tac atc ttt gtt gca aca gtg cca gtg ata gtg gct ttt att atg ttg    2955
Tyr Ile Phe Val Ala Thr Val Pro Val Ile Val Ala Phe Ile Met Leu
                930                 935                 940 aga gca tat ttc ctc caa acc tca cag caa ctc aaa caa ctg gaa tct    3003
Arg Ala Tyr Phe Leu Gln Thr Ser Gln Gln Leu Lys Gln Leu Glu Ser
            945                 950                 955 gaa ggc agg agt cca att ttc act cat ctt gtt aca agc tta aaa gga    3051
Glu Gly Arg Ser Pro Ile Phe Thr His Leu Val Thr Ser Leu Lys Gly
        960                 965                 970 cta tgg aca ctt cgt gcc ttc gga cgg cag cct tac ttt gaa act ctg    3099
Leu Trp Thr Leu Arg Ala Phe Gly Arg Gln Pro Tyr Phe Glu Thr Leu
    975                 980                 985 ttc cac aaa gct ctg aat tta cat act gcc aac tgg ttc ttg tac ctg    3147
Phe His Lys Ala Leu Asn Leu His Thr Ala Asn Trp Phe Leu Tyr Leu
 990                 995                 1000                1005 tca aca ctg cgc tgg ttc caa atg aga ata gaa atg att ttt gtc atc    3195
Ser Thr Leu Arg Trp Phe Gln Met Arg Ile Glu Met Ile Phe Val Ile
                1010                1015                1020 ttc ttc att gct gtt acc ttc att tcc att tta aca aca gga gaa gga    3243
Phe Phe Ile Ala Val Thr Phe Ile Ser Ile Leu Thr Thr Gly Glu Gly
            1025                1030                1035 gaa gga aga gtt ggt att atc ctg act tta gcc atg aat atc atg agt    3291
Glu Gly Arg Val Gly Ile Ile Leu Thr Leu Ala Met Asn Ile Met Ser
        1040                1045                1050 aca ttg cag tgg gct gta aac tcc agc ata gat gtg gat agc ttg atg    3339
Thr Leu Gln Trp Ala Val Asn Ser Ser Ile Asp Val Asp Ser Leu Met
    1055                1060                1065 cga tct gtg agc cga gtc ttt aag ttc att gac atg cca aca gaa ggt    3387
Arg Ser Val Ser Arg Val Phe Lys Phe Ile Asp Met Pro Thr Glu Gly
1070                1075                1080                1085 aaa cct acc aag tca acc aaa cca tac aag aat ggc caa ctc tcg aaa    3435
Lys Pro Thr Lys Ser Thr Lys Pro Tyr Lys Asn Gly Gln Leu Ser Lys
                1090                1095                1100 gtt atg att att gag aat tca cac gtg aag aaa gat gac atc tgg ccc    3483
Val Met Ile Ile Glu Asn Ser His Val Lys Lys Asp Asp Ile Trp Pro
            1105                1110                1115 tca ggg ggc caa atg act gtc aaa gat ctc aca gca aaa tac aca gaa    3531
```

```
Ser Gly Gly Gln Met Thr Val Lys Asp Leu Thr Ala Lys Tyr Thr Glu
        1120                1125                1130 ggt gga aat gcc ata tta gag aac att tcc ttc tca ata agt cct ggc      3579
Gly Gly Asn Ala Ile Leu Glu Asn Ile Ser Phe Ser Ile Ser Pro Gly
1135                1140                1145 cag agg gtg ggc ctc ttg gga aga act gga tca ggg aag agt act ttg      3627
Gln Arg Val Gly Leu Leu Gly Arg Thr Gly Ser Gly Lys Ser Thr Leu
1150                1155                1160                1165 tta tca gct ttt ttg aga cta ctg aac act gaa gga gaa atc cag atc      3675
Leu Ser Ala Phe Leu Arg Leu Leu Asn Thr Glu Gly Glu Ile Gln Ile
        1170                1175                1180 gat ggt gtg tct tgg gat tca ata act ttg caa cag tgg agg aaa gcc      3723
Asp Gly Val Ser Trp Asp Ser Ile Thr Leu Gln Gln Trp Arg Lys Ala
        1185                1190                1195 ttt gga gtg ata cca cag aaa gta ttt att ttt tct gga aca ttt aga      3771
Phe Gly Val Ile Pro Gln Lys Val Phe Ile Phe Ser Gly Thr Phe Arg
        1200                1205                1210 aaa aac ttg gat ccc tat gaa cag tgg agt gat caa gaa ata tgg aaa      3819
Lys Asn Leu Asp Pro Tyr Glu Gln Trp Ser Asp Gln Glu Ile Trp Lys
        1215                1220                1225 gtt gca gat gag gtt ggg ctc aga tct gtg ata gaa cag ttt cct ggg      3867
Val Ala Asp Glu Val Gly Leu Arg Ser Val Ile Glu Gln Phe Pro Gly
1230                1235                1240                1245 aag ctt gac ttt gtc ctt gtg gat ggg ggc tgt gtc cta agc cat ggc      3915
Lys Leu Asp Phe Val Leu Val Asp Gly Gly Cys Val Leu Ser His Gly
        1250                1255                1260 cac aag cag ttg atg tgc ttg gct aga tct gtt ctc agt aag gcg aag      3963
His Lys Gln Leu Met Cys Leu Ala Arg Ser Val Leu Ser Lys Ala Lys
        1265                1270                1275 atc ttg ctg ctt gat gaa ccc agt gct cat ttg gat cca gta aca tac      4011
Ile Leu Leu Leu Asp Glu Pro Ser Ala His Leu Asp Pro Val Thr Tyr
        1280                1285                1290 caa ata att aga aga act cta aaa caa gca ttt gct gat tgc aca gta      4059
Gln Ile Ile Arg Arg Thr Leu Lys Gln Ala Phe Ala Asp Cys Thr Val
        1295                1300                1305 att ctc tgt gaa cac agg ata gaa gca atg ctg gaa tgc caa caa ttt      4107
Ile Leu Cys Glu His Arg Ile Glu Ala Met Leu Glu Cys Gln Gln Phe
1310                1315                1320                1325 ttg gtc ata gaa gag aac aaa gtg cgg cag tac gat tcc atc cag aaa      4155
Leu Val Ile Glu Glu Asn Lys Val Arg Gln Tyr Asp Ser Ile Gln Lys
        1330                1335                1340 ctg ctg aac gag agg agc ctc ttc cgg caa gcc atc agc ccc tcc gac      4203
Leu Leu Asn Glu Arg Ser Leu Phe Arg Gln Ala Ile Ser Pro Ser Asp
        1345                1350                1355 agg gtg aag ctc ttt ccc cac cgg aac tca agc aag tgc aag tct aag      4251
Arg Val Lys Leu Phe Pro His Arg Asn Ser Ser Lys Cys Lys Ser Lys
        1360                1365                1370 ccc cag att gct gct ctg aaa gag gag aca gaa gaa gag gtg caa gat      4299
Pro Gln Ile Ala Ala Leu Lys Glu Glu Thr Glu Glu Glu Val Gln Asp
        1375                1380                1385 aca agg ctt tag                                                       4311
Thr Arg Leu  *
1390

<210> SEQ ID NO 9
<211> LENGTH: 1352
<212> TYPE: PRT
<213> ORGANISM: homo sapiens

<400> SEQUENCE: 9
```

-continued

```
Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
             20                  25                  30

Glu Leu Ser Asp Ile Tyr Gln Ile Pro Ser Val Asp Ser Ala Asp Asn
         35                  40                  45

Leu Ser Glu Lys Leu Glu Arg Glu Trp Asp Arg Glu Leu Ala Ser Lys
 50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
             100                 105                 110

Asn Lys Glu Glu Arg Ser Ile Ala Ile Tyr Leu Gly Ile Gly Leu Cys
         115                 120                 125

Leu Leu Phe Ile Val Arg Thr Leu Leu Leu His Pro Ala Ile Phe Gly
 130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                 165                 170                 175

Ile Gly Gln Leu Val Ser Leu Leu Ser Asn Asn Leu Asn Lys Phe Asp
             180                 185                 190

Glu Gly Leu Ala Leu Ala His Phe Val Trp Ile Ala Pro Leu Gln Val
         195                 200                 205

Ala Leu Leu Met Gly Leu Ile Trp Glu Leu Leu Gln Ala Ser Ala Phe
 210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                 245                 250                 255

Glu Arg Leu Val Ile Thr Ser Glu Met Ile Glu Asn Ile Gln Ser Val
             260                 265                 270

Lys Ala Tyr Cys Trp Glu Glu Ala Met Glu Lys Met Ile Glu Asn Leu
         275                 280                 285

Arg Gln Thr Glu Leu Lys Leu Thr Arg Lys Ala Ala Tyr Val Arg Tyr
 290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                 325                 330                 335

Phe Thr Thr Ile Ser Phe Cys Ile Val Leu Arg Met Ala Val Thr Arg
             340                 345                 350

Gln Phe Pro Trp Ala Val Gln Thr Trp Tyr Asp Ser Leu Gly Ala Ile
         355                 360                 365

Asn Lys Ile Gln Asp Phe Leu Gln Lys Gln Glu Tyr Lys Thr Leu Glu
 370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                 405                 410                 415

Asn Asn Arg Lys Thr Ser Asn Gly Asp Asp Ser Leu Phe Phe Ser Asn
```

-continued

```
                420             425             430
Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
            530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu His Glu Gly Ser Ser
            610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
690                 695                 700

Ile Asn Ser Asp Met Glu Ser Ile Pro Ala Val Thr Thr Trp Asn Thr
705                 710                 715                 720

Tyr Leu Arg Tyr Ile Thr Val His Lys Ser Leu Ile Phe Val Leu Ile
                725                 730                 735

Trp Cys Leu Val Ile Phe Leu Ala Glu Val Ala Ala Ser Leu Val Val
            740                 745                 750

Leu Trp Leu Leu Gly Asn Thr Pro Leu Gln Asp Lys Gly Asn Ser Thr
            755                 760                 765

His Ser Arg Asn Asn Ser Tyr Ala Val Ile Ile Thr Ser Thr Ser Ser
            770                 775                 780

Tyr Tyr Val Phe Tyr Ile Tyr Val Gly Val Ala Asp Thr Leu Leu Ala
785                 790                 795                 800

Met Gly Phe Phe Arg Gly Leu Pro Leu Val His Thr Leu Ile Thr Val
                805                 810                 815

Ser Lys Ile Leu His His Lys Met Leu His Ser Val Leu Gln Ala Pro
            820                 825                 830

Met Ser Thr Leu Asn Thr Leu Lys Ala Gly Gly Ile Leu Asn Arg Phe
            835                 840                 845
```

-continued

```
Ser Lys Asp Ile Ala Ile Leu Asp Asp Leu Leu Pro Leu Thr Ile Phe
    850                 855                 860

Asp Phe Ile Gln Leu Leu Leu Ile Val Ile Gly Ala Ile Ala Val Val
865                 870                 875                 880

Ala Val Leu Gln Pro Tyr Ile Phe Val Ala Thr Val Pro Val Ile Val
                885                 890                 895

Ala Phe Ile Met Leu Arg Ala Tyr Phe Leu Gln Thr Ser Gln Gln Leu
                900                 905                 910

Lys Gln Leu Glu Ser Glu Gly Arg Ser Pro Ile Phe Thr His Leu Val
                915                 920                 925

Thr Ser Leu Lys Gly Leu Trp Thr Leu Arg Ala Phe Gly Arg Gln Pro
    930                 935                 940

Tyr Phe Glu Thr Leu Phe His Lys Ala Leu Asn Leu His Thr Ala Asn
945                 950                 955                 960

Trp Phe Leu Tyr Leu Ser Thr Leu Arg Trp Phe Gln Met Arg Ile Glu
                965                 970                 975

Met Ile Phe Val Ile Phe Phe Ile Ala Val Thr Phe Ile Ser Ile Leu
                980                 985                 990

Thr Thr Gly Glu Gly Glu Gly Arg Val Gly Ile Ile Leu Thr Leu Ala
    995                 1000                1005

Met Asn Ile Met Ser Thr Leu Gln Trp Ala Val Asn Ser Ser Ile Asp
    1010                1015                1020

Val Asp Ser Leu Met Arg Ser Val Ser Arg Val Phe Lys Phe Ile Asp
1025                1030                1035                1040

Met Pro Thr Glu Gly Lys Pro Thr Lys Ser Thr Lys Pro Tyr Lys Asn
                1045                1050                1055

Gly Gln Leu Ser Lys Val Met Ile Ile Glu Asn Ser His Val Lys Lys
                1060                1065                1070

Asp Asp Ile Trp Pro Ser Gly Gly Gln Met Thr Val Lys Asp Leu Thr
                1075                1080                1085

Ala Lys Tyr Thr Glu Gly Gly Asn Ala Ile Leu Glu Asn Ile Ser Phe
    1090                1095                1100

Ser Ile Ser Pro Gly Gln Arg Val Gly Leu Leu Gly Arg Thr Gly Ser
1105                1110                1115                1120

Gly Lys Ser Thr Leu Leu Ser Ala Phe Leu Arg Leu Leu Asn Thr Glu
                1125                1130                1135

Gly Glu Ile Gln Ile Asp Gly Val Ser Trp Asp Ser Ile Thr Leu Gln
                1140                1145                1150

Gln Trp Arg Lys Ala Phe Gly Val Ile Pro Gln Lys Val Phe Ile Phe
                1155                1160                1165

Ser Gly Thr Phe Arg Lys Asn Leu Asp Pro Tyr Glu Gln Trp Ser Asp
    1170                1175                1180

Gln Glu Ile Trp Lys Val Ala Asp Glu Val Gly Leu Arg Ser Val Ile
1185                1190                1195                1200

Glu Gln Phe Pro Gly Lys Leu Asp Phe Val Leu Val Asp Gly Gly Cys
                1205                1210                1215

Val Leu Ser His Gly His Lys Gln Leu Met Cys Leu Ala Arg Ser Val
                1220                1225                1230

Leu Ser Lys Ala Lys Ile Leu Leu Leu Asp Glu Pro Ser Ala His Leu
    1235                1240                1245

Asp Pro Val Thr Tyr Gln Ile Ile Arg Arg Thr Leu Lys Gln Ala Phe
    1250                1255                1260
```

```
Ala Asp Cys Thr Val Ile Leu Cys Glu His Arg Ile Glu Ala Met Leu
1265                1270                1275                1280

Glu Cys Gln Gln Phe Leu Val Ile Glu Glu Asn Lys Val Arg Gln Tyr
            1285                1290                1295

Asp Ser Ile Gln Lys Leu Leu Asn Glu Arg Ser Leu Phe Arg Gln Ala
        1300                1305                1310

Ile Ser Pro Ser Asp Arg Val Lys Leu Phe Pro His Arg Asn Ser Ser
    1315                1320                1325

Lys Cys Lys Ser Lys Pro Gln Ile Ala Ala Leu Lys Glu Glu Thr Glu
1330                1335                1340

Glu Glu Val Gln Asp Thr Arg Leu
1345                1350

<210> SEQ ID NO 10
<211> LENGTH: 1428
<212> TYPE: PRT
<213> ORGANISM: homo sapiens

<400> SEQUENCE: 10

Met Gln Arg Ser Pro Leu Glu Lys Ala Ser Val Val Ser Lys Leu Phe
 1               5                  10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
         35                  40                  45

Leu Ser Glu Lys Leu Glu Arg Glu Trp Asp Arg Glu Leu Ala Ser Lys
 50                  55                  60

Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285
```

-continued

```
Arg Gln Thr Glu Leu Lys Leu Thr Arg Lys Ala Ala Tyr Val Arg Tyr
    290                 295                 300

Phe Asn Ser Ser Ala Phe Phe Ser Gly Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
    515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700
```

-continued

Ile Asn Ser Thr Leu Gln Ala Arg Arg Arg Gln Ser Val Leu Asn Leu
705                 710                 715                 720

Met Thr His Ser Val Asn Gln Gly Gln Asn Ile His Arg Lys Thr Thr
            725                 730                 735

Ala Ser Thr Arg Lys Val Ser Leu Ala Pro Gln Ala Asn Leu Thr Glu
        740                 745                 750

Leu Asp Ile Tyr Ser Arg Arg Leu Ser Gln Glu Thr Gly Leu Glu Ile
    755                 760                 765

Ser Glu Glu Ile Asn Glu Glu Asp Leu Lys Glu Cys Phe Phe Asp Asp
770                 775                 780

Met Glu Ser Ile Pro Ala Val Thr Thr Trp Asn Thr Tyr Leu Arg Tyr
785                 790                 795                 800

Ile Thr Val His Lys Ser Leu Ile Phe Val Leu Ile Trp Cys Leu Val
            805                 810                 815

Ile Phe Leu Ala Glu Val Ala Ala Ser Leu Val Val Leu Trp Leu Leu
        820                 825                 830

Gly Asn Thr Pro Leu Gln Asp Lys Gly Asn Ser Thr His Ser Arg Asn
    835                 840                 845

Asn Ser Tyr Ala Val Ile Ile Thr Ser Thr Ser Ser Tyr Tyr Val Phe
850                 855                 860

Tyr Ile Tyr Val Gly Val Ala Asp Thr Leu Leu Ala Met Gly Phe Phe
865                 870                 875                 880

Arg Gly Leu Pro Leu Val His Thr Leu Ile Thr Val Ser Lys Ile Leu
            885                 890                 895

His His Lys Met Leu His Ser Val Leu Gln Ala Pro Met Ser Thr Leu
        900                 905                 910

Asn Thr Leu Lys Ala Gly Gly Ile Leu Asn Arg Phe Ser Lys Asp Ile
    915                 920                 925

Ala Ile Leu Asp Asp Leu Leu Pro Leu Thr Ile Phe Asp Phe Ile Gln
930                 935                 940

Leu Leu Leu Ile Val Ile Gly Ala Ile Ala Val Val Ala Val Leu Gln
945                 950                 955                 960

Pro Tyr Ile Phe Val Ala Thr Val Pro Val Ile Val Ala Phe Ile Met
            965                 970                 975

Leu Arg Ala Tyr Phe Leu Gln Thr Ser Gln Gln Leu Lys Gln Leu Glu
        980                 985                 990

Ser Glu Gly Arg Ser Pro Ile Phe Thr His Leu Val Thr Ser Leu Lys
    995                 1000                1005

Gly Leu Trp Thr Leu Arg Ala Phe Gly Arg Gln Pro Tyr Phe Glu Thr
    1010                1015                1020

Leu Phe His Lys Ala Leu Asn Leu His Thr Ala Asn Trp Phe Leu Tyr
1025                1030                1035                1040

Leu Ser Thr Leu Arg Trp Phe Gln Met Arg Ile Glu Met Ile Phe Val
            1045                1050                1055

Ile Phe Phe Ile Ala Val Thr Phe Ile Ser Ile Leu Thr Thr Gly Glu
        1060                1065                1070

Gly Glu Gly Arg Val Gly Ile Ile Leu Thr Leu Ala Met Asn Ile Met
    1075                1080                1085

Ser Thr Leu Gln Trp Ala Val Asn Ser Ser Ile Asp Val Asp Ser Leu
    1090                1095                1100

Met Arg Ser Val Ser Arg Val Phe Lys Phe Ile Asp Met Pro Thr Glu
1105                1110                1115                1120

Gly Lys Pro Thr Lys Ser Thr Lys Pro Tyr Lys Asn Gly Gln Leu Ser

```
                      1125                1130                1135

Lys Val Met Ile Ile Glu Asn Ser His Val Lys Lys Asp Asp Ile Trp
            1140                1145                1150

Pro Ser Gly Gly Gln Met Thr Val Lys Asp Leu Thr Ala Lys Tyr Thr
        1155                1160                1165

Glu Gly Gly Asn Ala Ile Leu Glu Asn Ile Ser Phe Ser Ile Ser Pro
    1170                1175                1180

Gly Gln Arg Val Gly Leu Leu Gly Arg Thr Gly Ser Gly Lys Ser Thr
1185                1190                1195                1200

Leu Leu Ser Ala Phe Leu Arg Leu Leu Asn Thr Glu Gly Glu Ile Gln
                1205                1210                1215

Ile Asp Gly Val Ser Trp Asp Ser Ile Thr Leu Gln Gln Trp Arg Lys
            1220                1225                1230

Ala Phe Gly Val Ile Pro Gln Lys Val Phe Ile Phe Ser Gly Thr Phe
        1235                1240                1245

Arg Lys Asn Leu Asp Pro Tyr Glu Gln Trp Ser Asp Gln Glu Ile Trp
    1250                1255                1260

Lys Val Ala Asp Glu Val Gly Leu Arg Ser Val Ile Glu Gln Phe Pro
1265                1270                1275                1280

Gly Lys Leu Asp Phe Val Leu Val Asp Gly Gly Cys Val Leu Ser His
                1285                1290                1295

Gly His Lys Gln Leu Met Cys Leu Ala Arg Ser Val Leu Ser Lys Ala
            1300                1305                1310

Lys Ile Leu Leu Leu Asp Glu Pro Ser Ala His Leu Asp Pro Val Thr
        1315                1320                1325

Tyr Gln Ile Ile Arg Arg Thr Leu Lys Gln Ala Phe Ala Asp Cys Thr
    1330                1335                1340

Val Ile Leu Cys Glu His Arg Ile Glu Ala Met Leu Glu Cys Gln Gln
1345                1350                1355                1360

Phe Leu Val Ile Glu Glu Asn Lys Val Arg Gln Tyr Asp Ser Ile Gln
                1365                1370                1375

Lys Leu Leu Asn Glu Arg Ser Leu Phe Arg Gln Ala Ile Ser Pro Ser
            1380                1385                1390

Asp Arg Val Lys Leu Phe Pro His Arg Asn Ser Ser Lys Cys Lys Ser
        1395                1400                1405

Lys Pro Gln Ile Ala Ala Leu Lys Glu Glu Thr Glu Glu Glu Val Gln
    1410                1415                1420

Asp Thr Arg Leu
1425

<210> SEQ ID NO 11
<211> LENGTH: 1425
<212> TYPE: PRT
<213> ORGANISM: homo sapiens

<400> SEQUENCE: 11

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60
```

```
Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
             100                 105                 110

Asn Lys Glu Glu Arg Ser Ile Ala Ile Tyr Leu Gly Ile Gly Leu Cys
             115                 120                 125

Leu Leu Phe Ile Val Arg Thr Leu Leu His Pro Ala Ile Phe Gly
     130                 135                 140

Leu His His Ile Gly Met Gln Met Arg Ile Ala Met Phe Ser Leu Ile
 145                 150                 155                 160

Tyr Lys Lys Thr Leu Lys Leu Ser Ser Arg Val Leu Asp Lys Ile Ser
             165                 170                 175

Ile Gly Gln Leu Val Ser Leu Leu Ser Asn Asn Leu Asn Lys Phe Asp
             180                 185                 190

Glu Gly Leu Ala Leu Ala His Phe Val Trp Ile Ala Pro Leu Gln Val
         195                 200                 205

Ala Leu Leu Met Gly Leu Ile Trp Glu Leu Leu Gln Ala Ser Ala Phe
     210                 215                 220

Cys Gly Leu Gly Phe Leu Ile Val Leu Ala Leu Phe Gln Ala Gly Leu
 225                 230                 235                 240

Gly Arg Met Met Met Lys Tyr Arg Asp Gln Arg Ala Gly Lys Ile Ser
                 245                 250                 255

Glu Arg Leu Val Ile Thr Ser Glu Met Ile Glu Asn Ile Gln Ser Val
             260                 265                 270

Lys Ala Tyr Cys Trp Glu Glu Ala Met Glu Lys Met Ile Glu Asn Leu
             275                 280                 285

Arg Gln Thr Glu Leu Lys Leu Thr Arg Lys Ala Ala Tyr Val Arg Tyr
 290                 295                 300

Phe Asn Ser Ser Ala Phe Phe Phe Ser Gly Phe Phe Val Val Phe Leu
 305                 310                 315                 320

Ser Val Leu Pro Tyr Ala Leu Ile Lys Gly Ile Ile Leu Arg Lys Ile
             325                 330                 335

Phe Thr Thr Ile Ser Phe Cys Ile Val Leu Arg Met Ala Val Thr Arg
             340                 345                 350

Gln Phe Pro Trp Ala Val Gln Thr Trp Tyr Asp Ser Leu Gly Ala Ile
     355                 360                 365

Asn Lys Ile Gln Asp Phe Leu Gln Lys Gln Glu Tyr Lys Thr Leu Glu
 370                 375                 380

Tyr Asn Leu Thr Thr Thr Glu Val Val Met Glu Asn Val Thr Ala Phe
 385                 390                 395                 400

Trp Glu Glu Gly Phe Gly Glu Leu Phe Glu Lys Ala Lys Gln Asn Asn
             405                 410                 415

Asn Asn Arg Lys Thr Ser Asn Gly Asp Asp Ser Leu Phe Phe Ser Asn
         420                 425                 430

Phe Ser Leu Leu Gly Thr Pro Val Leu Lys Asp Ile Asn Phe Lys Ile
     435                 440                 445

Glu Arg Gly Gln Leu Leu Ala Val Ala Gly Ser Thr Gly Ala Gly Lys
 450                 455                 460

Thr Ser Leu Leu Met Met Ile Met Gly Glu Leu Glu Pro Ser Glu Gly
 465                 470                 475                 480

Lys Ile Lys His Ser Gly Arg Ile Ser Phe Cys Ser Gln Phe Ser Trp
```

-continued

```
                485                 490                 495
Ile Met Pro Gly Thr Ile Lys Glu Asn Ile Ile Phe Gly Val Ser Tyr
            500                 505                 510
Asp Glu Tyr Arg Tyr Arg Ser Val Ile Lys Ala Cys Gln Leu Glu Glu
            515                 520                 525
Asp Ile Ser Lys Phe Ala Glu Lys Asp Asn Ile Val Leu Gly Glu Gly
            530                 535                 540
Gly Ile Thr Leu Ser Gly Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
            565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
            595                 600                 605
His Leu Lys Lys Ala Asp Lys Ile Leu Ile Leu His Glu Gly Ser Ser
            610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
            645                 650                 655
Arg Arg Asn Ser Ile Leu Thr Glu Thr Leu His Arg Phe Ser Leu Glu
            660                 665                 670
Gly Asp Ala Pro Val Ser Trp Thr Glu Thr Lys Lys Gln Ser Phe Lys
            675                 680                 685
Gln Thr Gly Glu Phe Gly Glu Lys Arg Lys Asn Ser Ile Leu Asn Pro
            690                 695                 700
Ile Asn Ser Ile Glu Glu Asp Ser Asp Glu Pro Leu Glu Arg Arg Leu
705                 710                 715                 720
Ser Leu Val Pro Asp Ser Glu Gln Gly Glu Ala Ile His Arg Lys Thr
            725                 730                 735
Thr Ala Ser Thr Arg Lys Val Ser Leu Ala Pro Gln Ala Asn Leu Thr
            740                 745                 750
Glu Leu Asp Ile Tyr Ser Arg Arg Leu Ser Gln Glu Thr Gly Leu Glu
            755                 760                 765
Ile Ser Glu Glu Ile Asn Glu Glu Asp Leu Lys Glu Asp Met Glu Ser
            770                 775                 780
Ile Pro Ala Val Thr Thr Trp Asn Thr Tyr Leu Arg Tyr Ile Thr Val
785                 790                 795                 800
His Lys Ser Leu Ile Phe Val Leu Ile Trp Cys Leu Val Ile Phe Leu
            805                 810                 815
Ala Glu Val Ala Ala Ser Leu Val Val Leu Trp Leu Leu Gly Asn Thr
            820                 825                 830
Pro Leu Gln Asp Lys Gly Asn Ser Thr His Ser Arg Asn Asn Ser Tyr
            835                 840                 845
Ala Val Ile Ile Thr Ser Thr Ser Ser Tyr Tyr Val Phe Tyr Ile Tyr
            850                 855                 860
Val Gly Val Ala Asp Thr Leu Leu Ala Met Gly Phe Phe Arg Gly Leu
865                 870                 875                 880
Pro Leu Val His Thr Leu Ile Thr Val Ser Lys Ile Leu His His Lys
            885                 890                 895
Met Leu His Ser Val Leu Gln Ala Pro Met Ser Thr Leu Asn Thr Leu
            900                 905                 910
```

-continued

Lys Ala Gly Gly Ile Leu Asn Arg Phe Ser Lys Asp Ile Ala Ile Leu
            915                 920                 925

Asp Asp Leu Leu Pro Leu Thr Ile Phe Asp Phe Ile Gln Leu Leu Leu
        930                 935                 940

Ile Val Ile Gly Ala Ile Ala Val Val Ala Val Leu Gln Pro Tyr Ile
945                 950                 955                 960

Phe Val Ala Thr Val Pro Val Ile Val Ala Phe Ile Met Leu Arg Ala
                965                 970                 975

Tyr Phe Leu Gln Thr Ser Gln Gln Leu Lys Gln Leu Glu Ser Glu Gly
            980                 985                 990

Arg Ser Pro Ile Phe Thr His Leu Val Thr Ser Leu Lys Gly Leu Trp
        995                 1000                1005

Thr Leu Arg Ala Phe Gly Arg Gln Pro Tyr Phe Glu Thr Leu Phe His
    1010                1015                1020

Lys Ala Leu Asn Leu His Thr Ala Asn Trp Phe Leu Tyr Leu Ser Thr
1025                1030                1035                1040

Leu Arg Trp Phe Gln Met Arg Ile Glu Met Ile Phe Val Ile Phe Phe
            1045                1050                1055

Ile Ala Val Thr Phe Ile Ser Ile Leu Thr Thr Gly Glu Gly Glu Gly
            1060                1065                1070

Arg Val Gly Ile Ile Leu Thr Leu Ala Met Asn Ile Met Ser Thr Leu
        1075                1080                1085

Gln Trp Ala Val Asn Ser Ser Ile Asp Val Asp Ser Leu Met Arg Ser
        1090                1095                1100

Val Ser Arg Val Phe Lys Phe Ile Asp Met Pro Thr Glu Gly Lys Pro
1105                1110                1115                1120

Thr Lys Ser Thr Lys Pro Tyr Lys Asn Gly Gln Leu Ser Lys Val Met
            1125                1130                1135

Ile Ile Glu Asn Ser His Val Lys Lys Asp Asp Ile Trp Pro Ser Gly
            1140                1145                1150

Gly Gln Met Thr Val Lys Asp Leu Thr Ala Lys Tyr Thr Glu Gly Gly
        1155                1160                1165

Asn Ala Ile Leu Glu Asn Ile Ser Phe Ser Ile Ser Pro Gly Gln Arg
    1170                1175                1180

Val Gly Leu Leu Gly Arg Thr Gly Ser Gly Lys Ser Thr Leu Leu Ser
1185                1190                1195                1200

Ala Phe Leu Arg Leu Leu Asn Thr Glu Gly Glu Ile Gln Ile Asp Gly
            1205                1210                1215

Val Ser Trp Asp Ser Ile Thr Leu Gln Gln Trp Arg Lys Ala Phe Gly
            1220                1225                1230

Val Ile Pro Gln Lys Val Phe Ile Phe Ser Gly Thr Phe Arg Lys Asn
        1235                1240                1245

Leu Asp Pro Tyr Glu Gln Trp Ser Asp Gln Glu Ile Trp Lys Val Ala
    1250                1255                1260

Asp Glu Val Gly Leu Arg Ser Val Ile Glu Gln Phe Pro Gly Lys Leu
1265                1270                1275                1280

Asp Phe Val Leu Val Asp Gly Gly Cys Val Leu Ser His Gly His Lys
            1285                1290                1295

Gln Leu Met Cys Leu Ala Arg Ser Val Leu Ser Lys Ala Lys Ile Leu
            1300                1305                1310

Leu Leu Asp Glu Pro Ser Ala His Leu Asp Pro Val Thr Tyr Gln Ile
        1315                1320                1325

```
Ile Arg Arg Thr Leu Lys Gln Ala Phe Ala Asp Cys Thr Val Ile Leu
    1330                1335                1340

Cys Glu His Arg Ile Glu Ala Met Leu Glu Cys Gln Gln Phe Leu Val
1345                1350                1355                1360

Ile Glu Glu Asn Lys Val Arg Gln Tyr Asp Ser Ile Gln Lys Leu Leu
                1365                1370                1375

Asn Glu Arg Ser Leu Phe Arg Gln Ala Ile Ser Pro Ser Asp Arg Val
                1380                1385                1390

Lys Leu Phe Pro His Arg Asn Ser Ser Lys Cys Lys Ser Lys Pro Gln
                1395                1400                1405

Ile Ala Ala Leu Lys Glu Glu Thr Glu Glu Glu Val Gln Asp Thr Arg
    1410                1415                1420

Leu
1425

<210> SEQ ID NO 12
<211> LENGTH: 1412
<212> TYPE: PRT
<213> ORGANISM: homo sapiens

<400> SEQUENCE: 12

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
                260                 265                 270
```

-continued

```
Lys Ala Tyr Cys Trp Glu Glu Ala Met Glu Lys Met Ile Glu Asn Leu
            275                 280                 285
Arg Gln Thr Glu Leu Lys Leu Thr Arg Lys Ala Ala Tyr Val Arg Tyr
        290                 295                 300
Phe Asn Ser Ser Ala Phe Phe Phe Ser Gly Phe Val Val Phe Leu
305                 310                 315                 320
Ser Val Leu Pro Tyr Ala Leu Ile Lys Gly Ile Ile Leu Arg Lys Ile
                325                 330                 335
Phe Thr Thr Ile Ser Phe Cys Ile Val Leu Arg Met Ala Val Thr Arg
            340                 345                 350
Gln Phe Pro Trp Ala Val Gln Thr Trp Tyr Asp Ser Leu Gly Ala Ile
        355                 360                 365
Asn Lys Ile Gln Asp Phe Leu Gln Lys Gln Glu Tyr Lys Thr Leu Glu
    370                 375                 380
Tyr Asn Leu Thr Thr Thr Glu Val Val Met Glu Asn Val Thr Ala Phe
385                 390                 395                 400
Trp Glu Glu Gly Phe Gly Glu Leu Phe Glu Lys Ala Lys Gln Asn Asn
                405                 410                 415
Asn Asn Arg Lys Thr Ser Asn Gly Asp Asp Ser Leu Phe Phe Ser Asn
            420                 425                 430
Phe Ser Leu Leu Gly Thr Pro Val Leu Lys Asp Ile Asn Phe Lys Ile
        435                 440                 445
Glu Arg Gly Gln Leu Leu Ala Val Ala Gly Ser Thr Gly Ala Gly Lys
    450                 455                 460
Thr Ser Leu Leu Met Met Ile Met Gly Glu Leu Glu Pro Ser Glu Gly
465                 470                 475                 480
Lys Ile Lys His Ser Gly Arg Ile Ser Phe Cys Ser Gln Phe Ser Trp
                485                 490                 495
Ile Met Pro Gly Thr Ile Lys Glu Asn Ile Ile Phe Gly Val Ser Tyr
            500                 505                 510
Asp Glu Tyr Arg Tyr Arg Ser Val Ile Lys Ala Cys Gln Leu Glu Glu
        515                 520                 525
Asp Ile Ser Lys Phe Ala Glu Lys Asp Asn Ile Val Leu Gly Glu Gly
    530                 535                 540
Gly Ile Thr Leu Ser Gly Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
        595                 600                 605
His Leu Lys Lys Ala Asp Lys Ile Leu Ile Leu His Glu Gly Ser Ser
    610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
            660                 665                 670
Gly Asp Ala Pro Val Ser Trp Thr Glu Thr Lys Lys Gln Ser Phe Lys
        675                 680                 685
```

-continued

```
Gln Thr Gly Glu Phe Gly Glu Lys Arg Lys Asn Ser Ile Leu Asn Pro
    690                 695                 700

Ile Asn Ser Ile Glu Glu Asp Ser Asp Glu Pro Leu Glu Arg Arg Leu
705                 710                 715                 720

Ser Leu Val Pro Asp Ser Glu Gln Gly Glu Ala Ile His Arg Lys Thr
                725                 730                 735

Thr Ala Ser Thr Arg Lys Val Ser Leu Ala Pro Gln Ala Asn Leu Thr
            740                 745                 750

Glu Leu Asp Ile Tyr Ser Arg Arg Leu Ser Gln Glu Thr Gly Leu Asp
            755                 760                 765

Met Glu Ser Ile Pro Ala Val Thr Thr Trp Asn Thr Tyr Leu Arg Tyr
    770                 775                 780

Ile Thr Val His Lys Ser Leu Ile Phe Val Leu Ile Trp Cys Leu Val
785                 790                 795                 800

Ile Phe Leu Ala Glu Val Ala Ala Ser Leu Val Val Leu Trp Leu Leu
                805                 810                 815

Gly Asn Thr Pro Leu Gln Asp Lys Gly Asn Ser Thr His Ser Arg Asn
            820                 825                 830

Asn Ser Tyr Ala Val Ile Ile Thr Ser Thr Ser Ser Tyr Tyr Val Phe
            835                 840                 845

Tyr Ile Tyr Val Gly Val Ala Asp Thr Leu Leu Ala Met Gly Phe Phe
850                 855                 860

Arg Gly Leu Pro Leu Val His Thr Leu Ile Thr Val Ser Lys Ile Leu
865                 870                 875                 880

His His Lys Met Leu His Ser Val Leu Gln Ala Pro Met Ser Thr Leu
                885                 890                 895

Asn Thr Leu Lys Ala Gly Gly Ile Leu Asn Arg Phe Ser Lys Asp Ile
            900                 905                 910

Ala Ile Leu Asp Asp Leu Leu Pro Leu Thr Ile Phe Asp Phe Ile Gln
            915                 920                 925

Leu Leu Leu Ile Val Ile Gly Ala Ile Ala Val Val Ala Val Leu Gln
    930                 935                 940

Pro Tyr Ile Phe Val Ala Thr Val Pro Val Ile Val Ala Phe Ile Met
945                 950                 955                 960

Leu Arg Ala Tyr Phe Leu Gln Thr Ser Gln Gln Leu Lys Gln Leu Glu
                965                 970                 975

Ser Glu Gly Arg Ser Pro Ile Phe Thr His Leu Val Thr Ser Leu Lys
            980                 985                 990

Gly Leu Trp Thr Leu Arg Ala Phe Gly Arg Gln Pro Tyr Phe Glu Thr
    995                 1000                1005

Leu Phe His Lys Ala Leu Asn Leu His Thr Ala Asn Trp Phe Leu Tyr
    1010                1015                1020

Leu Ser Thr Leu Arg Trp Phe Gln Met Arg Ile Glu Met Ile Phe Val
1025                1030                1035                1040

Ile Phe Phe Ile Ala Val Thr Phe Ile Ser Ile Leu Thr Thr Gly Glu
                1045                1050                1055

Gly Glu Gly Arg Val Gly Ile Ile Leu Thr Leu Ala Met Asn Ile Met
            1060                1065                1070

Ser Thr Leu Gln Trp Ala Val Asn Ser Ser Ile Asp Val Asp Ser Leu
    1075                1080                1085

Met Arg Ser Val Ser Arg Val Phe Lys Phe Ile Asp Met Pro Thr Glu
    1090                1095                1100

Gly Lys Pro Thr Lys Ser Thr Lys Pro Tyr Lys Asn Gly Gln Leu Ser
```

```
                1105                1110                1115                1120
Lys Val Met Ile Ile Glu Asn Ser His Val Lys Lys Asp Asp Ile Trp
                    1125                1130                1135
Pro Ser Gly Gly Gln Met Thr Val Lys Asp Leu Thr Ala Lys Tyr Thr
            1140                1145                1150
Glu Gly Gly Asn Ala Ile Leu Glu Asn Ile Ser Phe Ser Ile Ser Pro
        1155                1160                1165
Gly Gln Arg Val Gly Leu Leu Gly Arg Thr Gly Ser Gly Lys Ser Thr
    1170                1175                1180
Leu Leu Ser Ala Phe Leu Arg Leu Leu Asn Thr Glu Gly Glu Ile Gln
1185                1190                1195                1200
Ile Asp Gly Val Ser Trp Asp Ser Ile Thr Leu Gln Gln Trp Arg Lys
                1205                1210                1215
Ala Phe Gly Val Ile Pro Gln Lys Val Phe Ile Phe Ser Gly Thr Phe
                    1220                1225                1230
Arg Lys Asn Leu Asp Pro Tyr Glu Gln Trp Ser Asp Gln Glu Ile Trp
            1235                1240                1245
Lys Val Ala Asp Glu Val Gly Leu Arg Ser Val Ile Glu Gln Phe Pro
        1250                1255                1260
Gly Lys Leu Asp Phe Val Leu Val Asp Gly Gly Cys Val Leu Ser His
1265                1270                1275                1280
Gly His Lys Gln Leu Met Cys Leu Ala Arg Ser Val Leu Ser Lys Ala
                1285                1290                1295
Lys Ile Leu Leu Leu Asp Glu Pro Ser Ala His Leu Asp Pro Val Thr
                    1300                1305                1310
Tyr Gln Ile Ile Arg Arg Thr Leu Lys Gln Ala Phe Ala Asp Cys Thr
            1315                1320                1325
Val Ile Leu Cys Glu His Arg Ile Glu Ala Met Leu Glu Cys Gln Gln
        1330                1335                1340
Phe Leu Val Ile Glu Glu Asn Lys Val Arg Gln Tyr Asp Ser Ile Gln
1345                1350                1355                1360
Lys Leu Leu Asn Glu Arg Ser Leu Phe Arg Gln Ala Ile Ser Pro Ser
                1365                1370                1375
Asp Arg Val Lys Leu Phe Pro His Arg Asn Ser Ser Lys Cys Lys Ser
                    1380                1385                1390
Lys Pro Gln Ile Ala Ala Leu Lys Glu Glu Thr Glu Glu Val Gln
            1395                1400                1405
Asp Thr Arg Leu
    1410

<210> SEQ ID NO 13
<211> LENGTH: 1411
<212> TYPE: PRT
<213> ORGANISM: homo sapiens

<400> SEQUENCE: 13

Met Gln Arg Ser Pro Leu Glu Lys Ala Ser Val Val Ser Lys Leu Phe
1               5                   10                  15
Phe Ser Trp Thr Arg Pro Ile Leu Arg Lys Gly Tyr Arg Gln Arg Leu
                20                  25                  30
Glu Leu Ser Asp Ile Tyr Gln Ile Pro Ser Val Asp Ser Ala Asp Asn
            35                  40                  45
Leu Ser Glu Lys Leu Glu Arg Glu Trp Asp Arg Glu Leu Ala Ser Lys
        50                  55                  60
```

-continued

```
Lys Asn Pro Lys Leu Ile Asn Ala Leu Arg Arg Cys Phe Phe Trp Arg
 65                  70                  75                  80

Phe Met Phe Tyr Gly Ile Phe Leu Tyr Leu Gly Glu Val Thr Lys Ala
                 85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
            210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
```

-continued

```
                485                 490                 495
Ile Met Pro Gly Thr Ile Lys Glu Asn Ile Ile Phe Gly Val Ser Tyr
            500                 505                 510
Asp Glu Tyr Arg Tyr Arg Ser Val Ile Lys Ala Cys Gln Leu Glu Glu
            515                 520                 525
Asp Ile Ser Lys Phe Ala Glu Lys Asp Asn Ile Val Leu Gly Glu Gly
            530                 535                 540
Gly Ile Thr Leu Ser Gly Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
            565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
            595                 600                 605
His Leu Lys Lys Ala Asp Lys Ile Leu Ile Leu His Glu Gly Ser Ser
            610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
            645                 650                 655
Arg Arg Asn Ser Ile Leu Thr Glu Thr Leu His Arg Phe Ser Leu Glu
            660                 665                 670
Gly Asp Ala Pro Val Ser Trp Thr Glu Thr Lys Lys Gln Ser Phe Lys
            675                 680                 685
Gln Thr Gly Glu Phe Gly Glu Lys Arg Lys Asn Ser Ile Leu Asn Pro
            690                 695                 700
Ile Asn Ser Thr Leu Gln Ala Arg Arg Gln Ser Val Leu Asn Leu
705                 710                 715                 720
Met Thr His Ser Val Asn Gln Gly Gln Asn Ile His Arg Lys Thr Thr
            725                 730                 735
Ala Ser Thr Arg Lys Val Ser Leu Ala Pro Gln Ala Asn Leu Thr Glu
            740                 745                 750
Leu Asp Ile Tyr Ser Arg Arg Leu Ser Gln Glu Thr Gly Leu Asp Met
            755                 760                 765
Glu Ser Ile Pro Ala Val Thr Thr Trp Asn Thr Tyr Leu Arg Tyr Ile
            770                 775                 780
Thr Val His Lys Ser Leu Ile Phe Val Leu Ile Trp Cys Leu Val Ile
785                 790                 795                 800
Phe Leu Ala Glu Val Ala Ala Ser Leu Val Val Leu Trp Leu Leu Gly
            805                 810                 815
Asn Thr Pro Leu Gln Asp Lys Gly Asn Ser Thr His Ser Arg Asn Asn
            820                 825                 830
Ser Tyr Ala Val Ile Ile Thr Ser Thr Ser Ser Tyr Tyr Val Phe Tyr
            835                 840                 845
Ile Tyr Val Gly Val Ala Asp Thr Leu Leu Ala Met Gly Phe Phe Arg
            850                 855                 860
Gly Leu Pro Leu Val His Thr Leu Ile Thr Val Ser Lys Ile Leu His
865                 870                 875                 880
His Lys Met Leu His Ser Val Leu Gln Ala Pro Met Ser Thr Leu Asn
            885                 890                 895
Thr Leu Lys Ala Gly Gly Ile Leu Asn Arg Phe Ser Lys Asp Ile Ala
            900                 905                 910
```

-continued

Ile Leu Asp Asp Leu Leu Pro Leu Thr Ile Phe Asp Phe Ile Gln Leu
            915                 920                 925

Leu Leu Ile Val Ile Gly Ala Ile Ala Val Val Ala Val Leu Gln Pro
            930                 935                 940

Tyr Ile Phe Val Ala Thr Val Pro Val Ile Val Ala Phe Ile Met Leu
945                 950                 955                 960

Arg Ala Tyr Phe Leu Gln Thr Ser Gln Gln Leu Lys Gln Leu Glu Ser
            965                 970                 975

Glu Gly Arg Ser Pro Ile Phe Thr His Leu Val Thr Ser Leu Lys Gly
            980                 985                 990

Leu Trp Thr Leu Arg Ala Phe Gly Arg Gln Pro Tyr Phe Glu Thr Leu
            995                 1000                1005

Phe His Lys Ala Leu Asn Leu His Thr Ala Asn Trp Phe Leu Tyr Leu
            1010                1015                1020

Ser Thr Leu Arg Trp Phe Gln Met Arg Ile Glu Met Ile Phe Val Ile
1025                1030                1035                1040

Phe Phe Ile Ala Val Thr Phe Ile Ser Ile Leu Thr Thr Gly Glu Gly
            1045                1050                1055

Glu Gly Arg Val Gly Ile Ile Leu Thr Leu Ala Met Asn Ile Met Ser
            1060                1065                1070

Thr Leu Gln Trp Ala Val Asn Ser Ser Ile Asp Val Asp Ser Leu Met
            1075                1080                1085

Arg Ser Val Ser Arg Val Phe Lys Phe Ile Asp Met Pro Thr Glu Gly
            1090                1095                1100

Lys Pro Thr Lys Ser Thr Lys Pro Tyr Lys Asn Gly Gln Leu Ser Lys
1105                1110                1115                1120

Val Met Ile Ile Glu Asn Ser His Val Lys Lys Asp Asp Ile Trp Pro
            1125                1130                1135

Ser Gly Gly Gln Met Thr Val Lys Asp Leu Thr Ala Lys Tyr Thr Glu
            1140                1145                1150

Gly Gly Asn Ala Ile Leu Glu Asn Ile Ser Phe Ser Ile Ser Pro Gly
            1155                1160                1165

Gln Arg Val Gly Leu Leu Gly Arg Thr Gly Ser Gly Lys Ser Thr Leu
            1170                1175                1180

Leu Ser Ala Phe Leu Arg Leu Leu Asn Thr Glu Gly Glu Ile Gln Ile
1185                1190                1195                1200

Asp Gly Val Ser Trp Asp Ser Ile Thr Leu Gln Gln Trp Arg Lys Ala
            1205                1210                1215

Phe Gly Val Ile Pro Gln Lys Val Phe Ile Phe Ser Gly Thr Phe Arg
            1220                1225                1230

Lys Asn Leu Asp Pro Tyr Glu Gln Trp Ser Asp Gln Glu Ile Trp Lys
            1235                1240                1245

Val Ala Asp Glu Val Gly Leu Arg Ser Val Ile Glu Gln Phe Pro Gly
            1250                1255                1260

Lys Leu Asp Phe Val Leu Val Asp Gly Gly Cys Val Leu Ser His Gly
1265                1270                1275                1280

His Lys Gln Leu Met Cys Leu Ala Arg Ser Val Leu Ser Lys Ala Lys
            1285                1290                1295

Ile Leu Leu Leu Asp Glu Pro Ser Ala His Leu Asp Pro Val Thr Tyr
            1300                1305                1310

Gln Ile Ile Arg Arg Thr Leu Lys Gln Ala Phe Ala Asp Cys Thr Val
            1315                1320                1325

```
Ile Leu Cys Glu His Arg Ile Glu Ala Met Leu Glu Cys Gln Gln Phe
    1330                1335                1340

Leu Val Ile Glu Glu Asn Lys Val Arg Gln Tyr Asp Ser Ile Gln Lys
1345                1350                1355                1360

Leu Leu Asn Glu Arg Ser Leu Phe Arg Gln Ala Ile Ser Pro Ser Asp
                1365                1370                1375

Arg Val Lys Leu Phe Pro His Arg Asn Ser Ser Lys Cys Lys Ser Lys
                1380                1385                1390

Pro Gln Ile Ala Ala Leu Lys Glu Glu Thr Glu Glu Glu Val Gln Asp
                1395                1400                1405

Thr Arg Leu
    1410

<210> SEQ ID NO 14
<211> LENGTH: 1404
<212> TYPE: PRT
<213> ORGANISM: homo sapiens

<400> SEQUENCE: 14

Met Gln Arg Ser Pro Leu Glu Lys Ala Ser Val Val Ser Lys Leu Phe
  1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
                100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
        130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
                180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
        210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
                260                 265                 270

Lys Ala Tyr Cys Trp Glu Glu Ala Met Glu Lys Met Ile Glu Asn Leu
            275                 280                 285
```

-continued

```
Arg Gln Thr Glu Leu Lys Leu Thr Arg Lys Ala Ala Tyr Val Arg Tyr
    290                 295                 300

Phe Asn Ser Ser Ala Phe Phe Ser Gly Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
        420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
                500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
        610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700
```

-continued

```
Ile Asn Ser Ile Arg Lys Phe Ser Ile Val Gln Lys Thr Pro Leu Gln
705                 710                 715                 720

Met Asn Gly Ile Glu Asp Ser Asp Glu Pro Leu Glu Arg Arg Leu
            725                 730                 735

Ser Leu Val Pro Asp Ser Glu Gln Gly Glu Ala Ile Leu Pro Arg Ile
            740                 745                 750

Ser Val Ile Ser Thr Gly Pro Asp Met Glu Ser Ile Pro Ala Val Thr
            755                 760                 765

Thr Trp Asn Thr Tyr Leu Arg Tyr Ile Thr Val His Lys Ser Leu Ile
    770                 775                 780

Phe Val Leu Ile Trp Cys Leu Val Ile Phe Leu Ala Glu Val Ala Ala
785                 790                 795                 800

Ser Leu Val Val Leu Trp Leu Leu Gly Asn Thr Pro Leu Gln Asp Lys
            805                 810                 815

Gly Asn Ser Thr His Ser Arg Asn Asn Ser Tyr Ala Val Ile Ile Thr
            820                 825                 830

Ser Thr Ser Ser Tyr Tyr Val Phe Tyr Ile Tyr Val Gly Val Ala Asp
            835                 840                 845

Thr Leu Leu Ala Met Gly Phe Phe Arg Gly Leu Pro Leu Val His Thr
    850                 855                 860

Leu Ile Thr Val Ser Lys Ile Leu His His Lys Met Leu His Ser Val
865                 870                 875                 880

Leu Gln Ala Pro Met Ser Thr Leu Asn Thr Leu Lys Ala Gly Gly Ile
            885                 890                 895

Leu Asn Arg Phe Ser Lys Asp Ile Ala Ile Leu Asp Asp Leu Leu Pro
            900                 905                 910

Leu Thr Ile Phe Asp Phe Ile Gln Leu Leu Leu Ile Val Ile Gly Ala
            915                 920                 925

Ile Ala Val Val Ala Val Leu Gln Pro Tyr Ile Phe Val Ala Thr Val
930                 935                 940

Pro Val Ile Val Ala Phe Ile Met Leu Arg Ala Tyr Phe Leu Gln Thr
945                 950                 955                 960

Ser Gln Gln Leu Lys Gln Leu Glu Ser Glu Gly Arg Ser Pro Ile Phe
            965                 970                 975

Thr His Leu Val Thr Ser Leu Lys Gly Leu Trp Thr Leu Arg Ala Phe
            980                 985                 990

Gly Arg Gln Pro Tyr Phe Glu Thr Leu Phe His Lys Ala Leu Asn Leu
            995                 1000                1005

His Thr Ala Asn Trp Phe Leu Tyr Leu Ser Thr Leu Arg Trp Phe Gln
    1010                1015                1020

Met Arg Ile Glu Met Ile Phe Val Ile Phe Phe Ile Ala Val Thr Phe
1025                1030                1035                1040

Ile Ser Ile Leu Thr Thr Gly Glu Gly Glu Gly Arg Val Gly Ile Ile
            1045                1050                1055

Leu Thr Leu Ala Met Asn Ile Met Ser Thr Leu Gln Trp Ala Val Asn
            1060                1065                1070

Ser Ser Ile Asp Val Asp Ser Leu Met Arg Ser Val Ser Arg Val Phe
            1075                1080                1085

Lys Phe Ile Asp Met Pro Thr Glu Gly Lys Pro Thr Lys Ser Thr Lys
            1090                1095                1100

Pro Tyr Lys Asn Gly Gln Leu Ser Lys Val Met Ile Ile Glu Asn Ser
1105                1110                1115                1120

His Val Lys Lys Asp Asp Ile Trp Pro Ser Gly Gly Gln Met Thr Val
```

-continued

```
                1125                1130                1135
Lys Asp Leu Thr Ala Lys Tyr Thr Glu Gly Gly Asn Ala Ile Leu Glu
            1140                1145                1150

Asn Ile Ser Phe Ser Ile Ser Pro Gly Gln Arg Val Gly Leu Leu Gly
            1155                1160                1165

Arg Thr Gly Ser Gly Lys Ser Thr Leu Leu Ser Ala Phe Leu Arg Leu
            1170                1175                1180

Leu Asn Thr Glu Gly Glu Ile Gln Ile Asp Gly Val Ser Trp Asp Ser
1185                1190                1195                1200

Ile Thr Leu Gln Gln Trp Arg Lys Ala Phe Gly Val Ile Pro Gln Lys
            1205                1210                1215

Val Phe Ile Phe Ser Gly Thr Phe Arg Lys Asn Leu Asp Pro Tyr Glu
            1220                1225                1230

Gln Trp Ser Asp Gln Glu Ile Trp Lys Val Ala Asp Glu Val Gly Leu
            1235                1240                1245

Arg Ser Val Ile Glu Gln Phe Pro Gly Lys Leu Asp Phe Val Leu Val
            1250                1255                1260

Asp Gly Gly Cys Val Leu Ser His Gly His Lys Gln Leu Met Cys Leu
1265                1270                1275                1280

Ala Arg Ser Val Leu Ser Lys Ala Lys Ile Leu Leu Leu Asp Glu Pro
            1285                1290                1295

Ser Ala His Leu Asp Pro Val Thr Tyr Gln Ile Ile Arg Arg Thr Leu
            1300                1305                1310

Lys Gln Ala Phe Ala Asp Cys Thr Val Ile Leu Cys Glu His Arg Ile
            1315                1320                1325

Glu Ala Met Leu Glu Cys Gln Gln Phe Leu Val Ile Glu Glu Asn Lys
            1330                1335                1340

Val Arg Gln Tyr Asp Ser Ile Gln Lys Leu Leu Asn Glu Arg Ser Leu
1345                1350                1355                1360

Phe Arg Gln Ala Ile Ser Pro Ser Asp Arg Val Lys Leu Phe Pro His
            1365                1370                1375

Arg Asn Ser Ser Lys Cys Lys Ser Lys Pro Gln Ile Ala Ala Leu Lys
            1380                1385                1390

Glu Glu Thr Glu Glu Glu Val Gln Asp Thr Arg Leu
            1395                1400

<210> SEQ ID NO 15
<211> LENGTH: 1404
<212> TYPE: PRT
<213> ORGANISM: homo sapiens

<400> SEQUENCE: 15

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
        50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95
```

-continued

```
Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
```

-continued

```
                515                 520                 525
Asp Ile Ser Lys Phe Ala Glu Lys Asp Asn Ile Val Leu Gly Glu Gly
            530                 535                 540
Gly Ile Thr Leu Ser Gly Gly Gln Arg Ala Arg Ile Ser Leu Ala Arg
545                 550                 555                 560
Ala Val Tyr Lys Asp Ala Asp Leu Tyr Leu Leu Asp Ser Pro Phe Gly
                565                 570                 575
Tyr Leu Asp Val Leu Thr Glu Lys Glu Ile Phe Glu Ser Cys Val Cys
            580                 585                 590
Lys Leu Met Ala Asn Lys Thr Arg Ile Leu Val Thr Ser Lys Met Glu
        595                 600                 605
His Leu Lys Lys Ala Asp Lys Ile Leu Ile Leu His Glu Gly Ser Ser
        610                 615                 620
Tyr Phe Tyr Gly Thr Phe Ser Glu Leu Gln Asn Leu Gln Pro Asp Phe
625                 630                 635                 640
Ser Ser Lys Leu Met Gly Cys Asp Ser Phe Asp Gln Phe Ser Ala Glu
                645                 650                 655
Arg Arg Asn Ser Ile Leu Thr Glu Thr Leu His Arg Phe Ser Leu Glu
            660                 665                 670
Gly Asp Ala Pro Val Ser Trp Thr Glu Thr Lys Lys Gln Ser Phe Lys
675                 680                 685
Gln Thr Gly Glu Phe Gly Glu Lys Arg Lys Asn Ser Ile Leu Asn Pro
        690                 695                 700
Ile Asn Ser His Arg Lys Thr Thr Ala Ser Thr Arg Lys Val Ser Leu
705                 710                 715                 720
Ala Pro Gln Ala Asn Leu Thr Glu Leu Asp Ile Tyr Ser Arg Arg Leu
                725                 730                 735
Ser Gln Glu Thr Gly Leu Glu Ile Ser Glu Glu Ile Asn Glu Glu Asp
            740                 745                 750
Leu Lys Glu Cys Phe Phe Asp Asp Met Glu Ser Ile Pro Ala Val Thr
        755                 760                 765
Thr Trp Asn Thr Tyr Leu Arg Tyr Ile Thr Val His Lys Ser Leu Ile
        770                 775                 780
Phe Val Leu Ile Trp Cys Leu Val Ile Phe Leu Ala Glu Val Ala Ala
785                 790                 795                 800
Ser Leu Val Val Leu Trp Leu Leu Gly Asn Thr Pro Leu Gln Asp Lys
                805                 810                 815
Gly Asn Ser Thr His Ser Arg Asn Asn Ser Tyr Ala Val Ile Ile Thr
            820                 825                 830
Ser Thr Ser Ser Tyr Tyr Val Phe Tyr Ile Tyr Val Gly Val Ala Asp
        835                 840                 845
Thr Leu Leu Ala Met Gly Phe Phe Arg Gly Leu Pro Leu Val His Thr
        850                 855                 860
Leu Ile Thr Val Ser Lys Ile Leu His His Lys Met Leu His Ser Val
865                 870                 875                 880
Leu Gln Ala Pro Met Ser Thr Leu Asn Thr Leu Lys Ala Gly Gly Ile
                885                 890                 895
Leu Asn Arg Phe Ser Lys Asp Ile Ala Ile Leu Asp Asp Leu Leu Pro
            900                 905                 910
Leu Thr Ile Phe Asp Phe Ile Gln Leu Leu Leu Ile Val Ile Gly Ala
        915                 920                 925
Ile Ala Val Val Ala Val Leu Gln Pro Tyr Ile Phe Val Ala Thr Val
        930                 935                 940
```

```
Pro Val Ile Val Ala Phe Ile Met Leu Arg Ala Tyr Phe Leu Gln Thr
945                 950                 955                 960

Ser Gln Gln Leu Lys Gln Leu Glu Ser Glu Gly Arg Ser Pro Ile Phe
                965                 970                 975

Thr His Leu Val Thr Ser Leu Lys Gly Leu Trp Thr Leu Arg Ala Phe
                980                 985                 990

Gly Arg Gln Pro Tyr Phe Glu Thr Leu Phe His Lys Ala Leu Asn Leu
                995                 1000                1005

His Thr Ala Asn Trp Phe Leu Tyr Leu Ser Thr Leu Arg Trp Phe Gln
        1010                1015                1020

Met Arg Ile Glu Met Ile Phe Val Ile Phe Phe Ile Ala Val Thr Phe
1025                1030                1035                1040

Ile Ser Ile Leu Thr Thr Gly Glu Gly Glu Gly Arg Val Gly Ile Ile
                1045                1050                1055

Leu Thr Leu Ala Met Asn Ile Met Ser Thr Leu Gln Trp Ala Val Asn
                1060                1065                1070

Ser Ser Ile Asp Val Asp Ser Leu Met Arg Ser Val Ser Arg Val Phe
        1075                1080                1085

Lys Phe Ile Asp Met Pro Thr Glu Gly Lys Pro Thr Lys Ser Thr Lys
        1090                1095                1100

Pro Tyr Lys Asn Gly Gln Leu Ser Lys Val Met Ile Ile Glu Asn Ser
1105                1110                1115                1120

His Val Lys Lys Asp Asp Ile Trp Pro Ser Gly Gly Gln Met Thr Val
                1125                1130                1135

Lys Asp Leu Thr Ala Lys Tyr Thr Glu Gly Gly Asn Ala Ile Leu Glu
                1140                1145                1150

Asn Ile Ser Phe Ser Ile Ser Pro Gly Gln Arg Val Gly Leu Leu Gly
        1155                1160                1165

Arg Thr Gly Ser Gly Lys Ser Thr Leu Leu Ser Ala Phe Leu Arg Leu
        1170                1175                1180

Leu Asn Thr Glu Gly Glu Ile Gln Ile Asp Gly Val Ser Trp Asp Ser
1185                1190                1195                1200

Ile Thr Leu Gln Gln Trp Arg Lys Ala Phe Gly Val Ile Pro Gln Lys
                1205                1210                1215

Val Phe Ile Phe Ser Gly Thr Phe Arg Lys Asn Leu Asp Pro Tyr Glu
                1220                1225                1230

Gln Trp Ser Asp Gln Glu Ile Trp Lys Val Ala Asp Glu Val Gly Leu
        1235                1240                1245

Arg Ser Val Ile Glu Gln Phe Pro Gly Lys Leu Asp Phe Val Leu Val
        1250                1255                1260

Asp Gly Gly Cys Val Leu Ser His Gly His Lys Gln Leu Met Cys Leu
1265                1270                1275                1280

Ala Arg Ser Val Leu Ser Lys Ala Lys Ile Leu Leu Leu Asp Glu Pro
                1285                1290                1295

Ser Ala His Leu Asp Pro Val Thr Tyr Gln Ile Ile Arg Arg Thr Leu
                1300                1305                1310

Lys Gln Ala Phe Ala Asp Cys Thr Val Ile Leu Cys Glu His Arg Ile
        1315                1320                1325

Glu Ala Met Leu Glu Cys Gln Gln Phe Leu Val Ile Glu Glu Asn Lys
        1330                1335                1340

Val Arg Gln Tyr Asp Ser Ile Gln Lys Leu Leu Asn Glu Arg Ser Leu
1345                1350                1355                1360
```

-continued

Phe Arg Gln Ala Ile Ser Pro Ser Asp Arg Val Lys Leu Phe Pro His
            1365                1370                1375

Arg Asn Ser Ser Lys Cys Lys Ser Lys Pro Gln Ile Ala Ala Leu Lys
        1380                1385                1390

Glu Glu Thr Glu Glu Val Gln Asp Thr Arg Leu
        1395                1400

<210> SEQ ID NO 16
<211> LENGTH: 1392
<212> TYPE: PRT
<213> ORGANISM: homo sapiens

<400> SEQUENCE: 16

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

-continued

```
Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
            370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
            435                 440                 445

Glu Arg Gly Gln Leu Leu Ala Val Ala Gly Ser Thr Gly Ala Gly Lys
            450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
            515                 520                 525

Asp Ile Ser Lys Phe Ala Glu Lys Asp Asn Ile Val Leu Gly Glu Gly
            530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
            595                 600                 605

His Leu Lys Lys Ala Asp Lys Ile Leu Ile Leu His Glu Gly Ser Ser
            610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
            675                 680                 685

Gln Thr Gly Glu Phe Gly Glu Lys Arg Lys Asn Ser Ile Leu Asn Pro
            690                 695                 700

Ile Asn Ser His Arg Lys Thr Thr Ala Ser Thr Arg Lys Val Ser Leu
705                 710                 715                 720

Ala Pro Gln Ala Asn Leu Thr Glu Leu Asp Ile Tyr Ser Arg Arg Leu
                725                 730                 735

Ser Gln Glu Thr Gly Leu Glu Ile Ser Glu Glu Asp Met Glu Ser Ile
            740                 745                 750
```

```
Pro Ala Val Thr Thr Trp Asn Thr Tyr Leu Arg Tyr Ile Thr Val His
        755                 760                 765
Lys Ser Leu Ile Phe Val Leu Ile Trp Cys Leu Val Ile Phe Leu Ala
        770                 775                 780
Glu Val Ala Ala Ser Leu Val Val Leu Trp Leu Gly Asn Thr Pro
785                 790                 795                 800
Leu Gln Asp Lys Gly Asn Ser Thr His Ser Arg Asn Asn Ser Tyr Ala
            805                 810                 815
Val Ile Ile Thr Ser Thr Ser Ser Tyr Tyr Val Phe Tyr Ile Tyr Val
                820                 825                 830
Gly Val Ala Asp Thr Leu Leu Ala Met Gly Phe Phe Arg Gly Leu Pro
            835                 840                 845
Leu Val His Thr Leu Ile Thr Val Ser Lys Ile Leu His His Lys Met
        850                 855                 860
Leu His Ser Val Leu Gln Ala Pro Met Ser Thr Leu Asn Thr Leu Lys
865                 870                 875                 880
Ala Gly Gly Ile Leu Asn Arg Phe Ser Lys Asp Ile Ala Ile Leu Asp
            885                 890                 895
Asp Leu Leu Pro Leu Thr Ile Phe Asp Phe Ile Gln Leu Leu Leu Ile
                900                 905                 910
Val Ile Gly Ala Ile Ala Val Ala Val Leu Gln Pro Tyr Ile Phe
            915                 920                 925
Val Ala Thr Val Pro Val Ile Val Ala Phe Ile Met Leu Arg Ala Tyr
        930                 935                 940
Phe Leu Gln Thr Ser Gln Gln Leu Lys Gln Leu Glu Ser Glu Gly Arg
945                 950                 955                 960
Ser Pro Ile Phe Thr His Leu Val Thr Ser Leu Lys Gly Leu Trp Thr
                965                 970                 975
Leu Arg Ala Phe Gly Arg Gln Pro Tyr Phe Glu Thr Leu Phe His Lys
            980                 985                 990
Ala Leu Asn Leu His Thr Ala Asn Trp Phe Leu Tyr Leu Ser Thr Leu
        995                 1000                1005
Arg Trp Phe Gln Met Arg Ile Glu Met Ile Phe Val Ile Phe Ile
    1010                1015                1020
Ala Val Thr Phe Ile Ser Ile Leu Thr Thr Gly Glu Gly Glu Gly Arg
1025                1030                1035                1040
Val Gly Ile Ile Leu Thr Leu Ala Met Asn Ile Met Ser Thr Leu Gln
            1045                1050                1055
Trp Ala Val Asn Ser Ser Ile Asp Val Asp Ser Leu Met Arg Ser Val
            1060                1065                1070
Ser Arg Val Phe Lys Phe Ile Asp Met Pro Thr Glu Gly Lys Pro Thr
            1075                1080                1085
Lys Ser Thr Lys Pro Tyr Lys Asn Gly Gln Leu Ser Lys Val Met Ile
        1090                1095                1100
Ile Glu Asn Ser His Val Lys Lys Asp Asp Ile Trp Pro Ser Gly Gly
1105                1110                1115                1120
Gln Met Thr Val Lys Asp Leu Thr Ala Lys Tyr Thr Glu Gly Gly Asn
            1125                1130                1135
Ala Ile Leu Glu Asn Ile Ser Phe Ser Ile Ser Pro Gly Gln Arg Val
            1140                1145                1150
Gly Leu Leu Gly Arg Thr Gly Ser Gly Lys Ser Thr Leu Leu Ser Ala
        1155                1160                1165
Phe Leu Arg Leu Leu Asn Thr Glu Gly Glu Ile Gln Ile Asp Gly Val
```

-continued

```
              1170                1175                1180
Ser Trp Asp Ser Ile Thr Leu Gln Gln Trp Arg Lys Ala Phe Gly Val
1185                1190                1195                1200

Ile Pro Gln Lys Val Phe Ile Phe Ser Gly Thr Phe Arg Lys Asn Leu
                1205                1210                1215

Asp Pro Tyr Glu Gln Trp Ser Asp Gln Glu Ile Trp Lys Val Ala Asp
                1220                1225                1230

Glu Val Gly Leu Arg Ser Val Ile Glu Gln Phe Pro Gly Lys Leu Asp
                    1235                1240                1245

Phe Val Leu Val Asp Gly Gly Cys Val Leu Ser His Gly His Lys Gln
    1250                1255                1260

Leu Met Cys Leu Ala Arg Ser Val Leu Ser Lys Ala Lys Ile Leu Leu
1265                1270                1275                1280

Leu Asp Glu Pro Ser Ala His Leu Asp Pro Val Thr Tyr Gln Ile Ile
                1285                1290                1295

Arg Arg Thr Leu Lys Gln Ala Phe Ala Asp Cys Thr Val Ile Leu Cys
                1300                1305                1310

Glu His Arg Ile Glu Ala Met Leu Glu Cys Gln Gln Phe Leu Val Ile
                1315                1320                1325

Glu Glu Asn Lys Val Arg Gln Tyr Asp Ser Ile Gln Lys Leu Leu Asn
1330                1335                1340

Glu Arg Ser Leu Phe Arg Gln Ala Ile Ser Pro Ser Asp Arg Val Lys
1345                1350                1355                1360

Leu Phe Pro His Arg Asn Ser Ser Lys Cys Lys Ser Lys Pro Gln Ile
                1365                1370                1375

Ala Ala Leu Lys Glu Glu Thr Glu Glu Val Gln Asp Thr Arg Leu
                1380                1385                1390
```

CFTR WITH A PARTIALLY DELETED R DOMAIN AND USES THEREOF

CROSS REFERENCE TO RELATED APPLICATIONS

This application claims priority under 35 U.S.C. §119(e) to Provisional Application No. 60/358,074, which was filed on Feb. 19, 2002.

SPECIFICATION

This invention was made in part with government support from the National Heart, Lung and Blood Institute (NHBLI). Therefore, the United States Government has certain rights in the invention.

FIELD OF THE INVENTION

This invention relates to DNA molecules encoding partially deleted CFTR and the CFTR proteins encoded thereby which are useful for treating cystic fibrosis (CF) airway disease.

BACKGROUND OF THE INVENTION

Various attempts have been made develop gene therapy for cystic fibrosis (CF) airway disease.

Airway disease is the major cause of morbidity and mortality in cystic fibrosis (CF), an autosomal recessive disease caused by mutations in the gene encoding the cystic fibrosis transmembrane conductance regulator (CFTR) Cl⁻ channel. Welsh et al., *The Metabolic and Molecular Basis of Inherited Disease*, eds. Scriver, C. R., Beaudet, A. L., Sly, W. S., Valle, D., Childs, B. & Vogelstein, B. (McGraw-Hill, New York). Gene transfer offers the potential for a new and effective treatment for CF airway disease. For reviews see Davies, Geddes & Alton, 2001, *J. Gene Med.* 3:409-417; Flotte, 1999, *Curr. Opin Mol. Ther.* 1:510-516; and Welsh, 1999, *J. Clin. Invest.* 104:1165-1166. Previous studies have shown the feasibility of transferring the CFTR cDNA to CF airway epithelial cells in vitro and in vivo. However, with most vectors two main problems limit gene transfer: gene transfer from the apical surface of differentiated airway epithelia is inefficient, and DNA molecule expression is transient. See Davies, Geddes & Alton, 2001, *J. Gene Med.* 3:409-417; Flotte, 1999, *Curr. Opin Mol. Ther.* 1:510-516; and Welsh, 1999, *J. Clin. Invest.* 104:1165-1166.

For developing CF gene therapy, adeno-associated virus (AAV) vectors have several potential advantages.

One limitation of AAV vectors is the small size of a DNA molecule that can be inserted. Studies testing the insert size suggest that 4100-4900 bp is the optimal genome size for packaging. See Dong, Fran & Frizzell, 1996, *Hum Gene Ther.* 7:2101-2112. In comparison, the coding sequence of full length CFTR is 4450 bp. Riordan et al., 1989, *Science* 245:1066-1073. Addition of the two inverted terminal repeats of AAV (300 bp), and minimal 3' and 5' untranslated regions (~100 bp) yields an insert (4850 bp) that leaves little room for promoter-enhancer elements, most of which are >600 bp. Some studies have attempted to circumvent this limitation by using AAV sequences as a promoter. See Zhang et al., 1998, *Proc. Natl. Acad. Sci.* 95:10158-10163; and Flotte et al., 1993, *J. Biol. Chem.* 268:3781-3790. However, their utility in differentiated airway epithelia and in vivo is uncertain.

A potential solution to this problem is to shorten the DNA molecule by selectively deleting coding sequence. This strategy has been proposed with a mini-dystrophin gene for Duschennes muscular dystrophy (Phelps et al., 1995, *Hum. Mol. Genet.* 4:1251-1258) and for CFTR (Zhang et al., 1998, *Proc. Natl. Acad. Sci.* 95:10158-10163; and Flotte et al., 1993, *J. Biol. Chem.* 268:3781-3790).

The CFTR R (regulatory) domain (for reviews on the R domain see Ostedgaard, Baldursson & Welsh, 2001, *J. Biol. Chem.* 276:7689-7692; Sheppard & Welsh, 1999, *Physiol. Rev.* 79:S23-S45; Gadsby & Nairn, 1999, *Pysiol. Rev.* 79:S77-S107; and Ma, 2000, *News Physiol. Sci.* 15:154-158) has been speculated to be an important domain. Earlier studies in heterologous cells indicated that the CFTR R domain is predominantly random coil and that parts of the R domain can be deleted without abolishing channel function. Phosphorylation of the R domain by the cAMP-dependent protein kinase (PKA) controls CFTR Cl⁻ channel activity. Although this domain contains several conserved serines that are phosphorylated by PKA, no one phosphoserine is required and several different phosphoserines contribute to regulation. While the boundaries of the R domain are not precisely defined, they extend approximately from residues 634-708 at the N-terminus to approximately 835 at the C-terminus. See Ostedgaard, Baldursson & Welsh, 2001, *J. Biol. Chem.* 276:7689-7692; Ostedgaard, et al., 2000, *Proc. Natl. Acad. Sci. U.S.A.* 97:5657-5662; and Csandy et al., 2000, *J. Gen. Physiol.* 116:477-500. Previous work has shown that residues 708-831 regulate activity, but in solution they are predominantly random coil. Ostedgaard, et al., 2000, *Proc. Natl. Acad. Sci. U.S.A.* 97:5657-5662. These studies suggest that selective deletions might not severely disrupt structure and that retention of consensus phosphorylation sites might be sufficient for PKA-dependent regulation. Importantly, several earlier studies deleted portions of the R domain without abolishing channel function. Zhang et al., 1998, *Proc. Natl. Acad. Sci. U.S.A.* 95:10158-10163; Rich et al., 1991, *Science* 253:205-207; Rich et al., 1993, *Receptors Channels* 1:221-232; Ma et al., 1997, *J. Biol. Chem.* 272:28133-28141; Vankeerberghen et al., 1999, *Biochemistry* 38:14988-14998; and Xie et al., 2000, *Biophys. J.* 78:1293-1305.

While these earlier studies suggested that a DNA molecule with R domain deletions might be of value in gene therapy applications, some alterations induced channel activity in the absence of phosphorylation, reduced the response to PKA-dependent phosphorylation, and/or reduced net channel activity. Zhang et al., 1998, *Proc. Natl. Acad. Sci. U.S.A.* 95:10158-10163; Ostedgaard, Baldursson & Welsh, 2001, *J. Biol. Chem.,* 276:7689-7692; Rich et al., 1991, *Science* 253:205-207; Rich et al., 1993, *Receptors Channels* 1:221-232; Ma et al., 1997, *J. Biol. Chem.* 272:28133-28141; Vankeerberghen et al., 1999, *Biochemistry* 38:14988-14998; and Xie et al., 2000, *Biophys. J.* 78:1293-1305. Moreover, previous studies have only examined CFTR expressed in heterologous cell lines and studied activity using the patch-clamp technique, planar lipid bilayers, or anion efflux. There is no information, prior to this invention, about their function in airway or other epithelia. Expression in epithelia is key in assessing their value for gene transfer because deletions could alter protein-protein interactions, targeting to the apical membrane, constitutive and stimulated activity, phosphorylation-dependent regulation, and perhaps toxicity.

The present invention solves these problems by deleting regions within the CFTR R (regulatory) domain (for reviews on the R domain see Ostedgaard, Baldursson & Welsh, 2001, J. Biol. Chem. 276:7689-7692; Sheppard & Welsh, 1999, Physiol. Rev. 79:S23-S45; Gadsby & Nairn, 1999, Pysiol. Rev. 79:S77-S107; and Ma, 2000, News Physiol. Sci. 15:154-158) to provide a partially deleted CFTR capable of forming Cl⁻ channels in airway epithelia in vitro and in vivo.

SUMMARY OF THE INVENTION

The present invention offers new therapies for treating Cystic Fibrosis (CF), that are based on novel DNA molecules and proteins encoded by the DNA molecules. The present invention features DNA molecules encoding CFTR proteins having a partially deleted R domain. The partial deletions in the R domain are between residues 708 and 835 of the wild-type CFTR.

In a preferred embodiment, the DNA molecules of the present invention encode a CFTR comprising a partially deleted R domain which is capable of normal targeting to the apical membrane, wild-type biosynthesis, and generating transepithelial Cl⁻ current in CF epithelia (see Examples below). In addition, the CFTR protein comprising a partially deleted R domain corrects the Cl⁻ transport defect in a CF subject when expression in their nasal mucosa (see Examples below). In one aspect, the CFTR comprising a partially deleted R domain provides low constitutive Cl⁻ current in CFTR channels and provides a functional chloride ion channel in CF airway epithelia cells.

In a particularly preferred embodiment of the present invention, the CFTR comprising a partially deleted R domain has a deletion selected from the group consisting of Δ708-759, Δ708-723/749-783/832-835 and Δ760-835.

The CFTR comprising a partially deleted R domain may also comprise deletions in other regions as long as it maintains the ability to provide a functional chloride ion channel in CF airway epithelia cells. Additional deletions may be useful in producing a DNA molecule encoding a CFTR protein which is better accommodated by a vector and to ensure efficient packaging.

BRIEF DESCRIPTION OF THE DRAWINGS

The patent or application file contains at least one drawing (photograph) in color. Copies of this patent or patent application with color photograph will be provided by the office upon request and payment of the necessary fee.

The present invention may be better understood with reference to the attached figures in which.

DETAILED DESCRIPTION OF THE INVENTION

Figure 1:
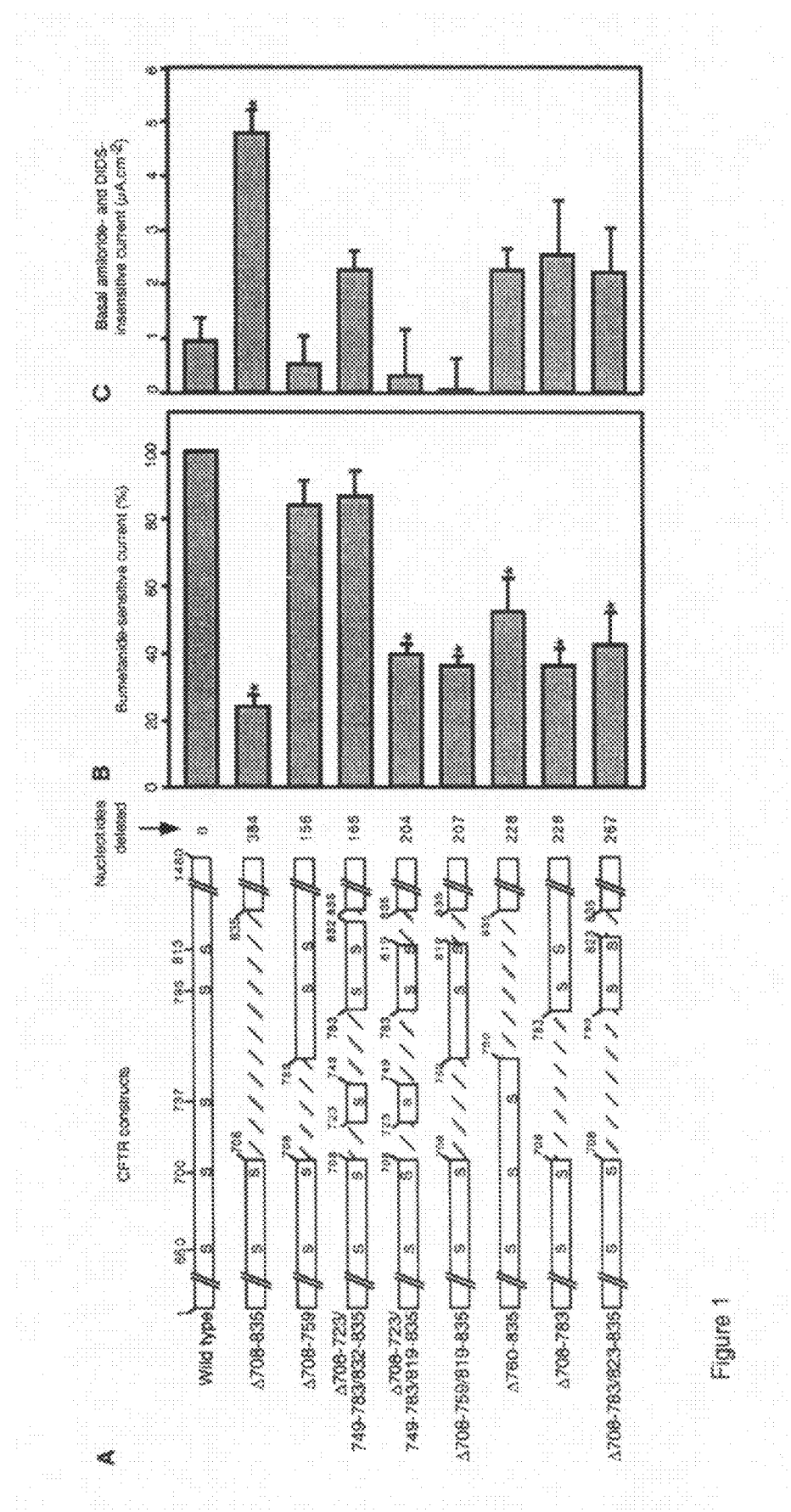
FIG. 1A shows a graphic representation of exemplary embodiments of CFTR proteins of the present invention; 1B shows bumetanide-sensitive short-circuit current in well-differentiated CF epithelia expressing the exemplary proteins shown in panel A; 1C shows basal current.

The present invention is based on the surprising finding that a defective DNA molecule, namely a DNA molecule encoding a CFTR protein comprising a partially deleted R domain, expresses a protein capable of providing a functional chloride ion channel in CF epithelia cells. Based on this finding, the invention features methods for making the DNA molecules expressing CFTR protein comprising a partially deleted R domain. The DNA molecules and CFTR protein encoded thereby can be used, for example, therapeutically in CF gene and protein replacement therapies.

As used herein the following words and phrases have the meaning set forth below:

"DNA molecule" shall mean a sequence of genetic material that carries the information representing a protein.

Unless otherwise indicated, "protein" shall mean a protein, polypeptide or peptide.

"CFTR or Cystic Fibrosis Transmembrane Conductance Regulator protein" refers to a 1480 amino acid protein containing two membrane-spanning domains (MSDs), two nucleotide binding domains (NBDs) and a unique R domain, that functions as a chloride channel regulated by phosphorylation and by nucleoside triphosphates.

The phrase "cystic fibrosis transmembrane conductance regulator (CFTR) activity or function"—is meant to refer to functions normally performed by wild-type CFTR. Such functions can include mediation of ion, (e.g. chloride ion) transport across cellular membranes.

A "Cystic Fibrosis (CF) cell" is a cell that lacks cystic fibrosis transmembrane conductance regulator function. Examples include CFTR mutants of which over 1000 different varieties have been identified to date (see for example, <HTTP://genet.sickkids.on.ca>).

"R (regulator) domain" refers to a domain that keeps a chloride channel closed at rest and which opens the channel when phosphorylated (e.g. by cAMP-dependent protein kinase (PKA) or protein kinase C (PKC)). The R domain of CFTR is encoded by a portion of exon 13, and generally comprises 128 amino acid residues that span from about amino acid residues 708 to 835 of full length CFTR or a lesser portion within this stretch. Ostedgaard et al., 2000, Proc. Natl. Acad. Sci. USA 97:5657-5662.

"Partially deleted R domain" refers to deletion of part, but not all, of the R domain.

"CF gene therapy" refers to the transfer of genetic material (e.g., DNA or RNA) encoding CFTR functional activity into a host to treat or prevent Cystic Fibrosis (CF).

"CF protein replacement therapy" refers to transfer of a protein having CFTR functional activity into a host to treat or prevent CF.

The nucleotide and amino acid sequence for full-length CFTR and modifications encoding CF mutant are known in the art (See, e.g., European Patent No. 0446017). Based on this information, one of skill in the art can obtain DNA molecules encoding CFTR comprising a partially deleted R domain using techniques that are well-known. For example, DNA molecules encoding CFTR can be isolated from appropriate cells or plasmids using standard techniques (e.g. restriction enzyme cleavage). Genetic material encoding full-length CFTR can then be modified (e.g. via deletion mutagenesis using Quik Change™ Mutagenesis, Stratagene, La Jolla, Calif.) to obtain a DNA molecule encoding a CFTR comprising a partially deleted R domain. Alternatively, a DNA molecule encoding a CFTR protein comprising a partially deleted R domain can be generated synthetically using standard modes of polynucleotide synthesis. A candidate gene can be tested to determine whether it in fact encodes functional CFTR activity, for example, using the techniques detailed below in the Examples.

An "expression cassette" comprising the gene encoding a CFTR comprising a partially deleted R domain operably linked or under the control of transcriptional and translational regulatory elements (e.g. a promoter, ribosome binding site, operator or enhancer) can be made and used for expression of CFTR protein comprising a partially deleted R domain in vitro or in vivo. The choice of regulatory elements employed may vary, depending, for example, on the host cell to be transfected and the desired level of expression. Several promoters for use in mammalian cells are known in the art and include, inter alia, the phosphoglycerate (PGK) promoter, the simian virus 40 (SV40) early promoter, the Rous sarcoma virus (RSV) promoter, the adenovirus major later promoter (MLP) and the human cytomegalovirus (CMV) immediate early 1 promoter. However, any promoter that facilitates suitable expression levels can be used in the present invention. Inducible promoters (e.g., those obtained from the heat shock gene, metallothionene gene, beta interferon gene, or steroid hormone responsive genes) may be useful for regulating transcription based on external stimuli.

A preferred DNA molecule encodes a CFTR protein comprising a deletion in the R domain wherein the deletion is selected from the group consisting of Δ708-835 (SEQ ID NO:1), Δ708-759 (SEQ ID NO:2), Δ708-723/749-783//832-835 (SEQ ID NO:3), Δ708-723/749-783/819-835 (SEQ ID NO:4), Δ708-759/819-835 (SEQ ID NO:5), Δ760-835 (SEQ ID NO:6), Δ708-783 (SEQ ID NO:7), and Δ708-783/823-835 (SEQ ID NO:8). A preferred CFTR protein comprises a deletion in the R domain wherein the deletion is selected from the group consisting of Δ708-835 (SEQ ID NO:9), Δ708-759 (SEQ ID NO:10), Δ708-723/749-783//832-835 (SEQ ID NO:11), Δ708-723/749-783/819-835 (SEQ ID NO:12), Δ708-759/819-835 (SEQ ID NO:13), Δ760-835 (SEQ ID NO:14), Δ708-783 (SEQ ID NO:15), and Δ708-783/823-835 (SEQ ID NO:16). More preferably, the DNA molecule encodes a CFTR protein comprising a deletion in the R domain selected from the group consisting of Δ708-759 (SEQ ID NO:2), Δ708-723/749-783//832-835 (SEQ ID NO:3), and Δ760-835 (SEQ ID NO:6) and the CFTR protein comprises a deletion in the R domain selected from the group consisting of Δ708-759 (SEQ ID NO:10), Δ708-723/749-783//832-835 (SEQ ID NO:11), and Δ760-835 (SEQ ID NO:14). In a particularly preferred embodiment, the DNA molecule encodes a CFTR protein comprising a deletion in the R domain of a of Δ708-759 (SEQ ID NO:2) and the CFTR protein comprises a deletion in the R domain Δ708-759 (SEQ ID NO:10). The CFTR protein of the present invention which comprises a deletion in the R domain is capable of providing a functional chloride ion channel in CF airway epithelia cells.

The DNA molecule of the present invention, and the protein encoded thereby may further comprise deletions of other regions of CFTR provided that the resultant CFTR protein is capable of providing a functional chloride ion channel in CF airway epithelia cells.

In another aspect of the invention, there is provided a DNA molecule encoding a CFTR protein comprising a partially deleted R domain wherein the encoded CFTR has low constitutive Cl⁻ current. As used herein, "low constitutive Cl⁻ current" means an amount of Cl⁻ current as determined in patch-clamp studies (described by Baldursson et. al., 2001, *J. Biol. Chem.* 276:1904-1910) which is less than $2 \ \mu A.cm^{-2}$. In one embodiment, the CFTR having low constitutive Cl⁻ current is selected from the group consisting of SEQ ID NO:10, SEQ ID NO:12, and SEQ ID NO:13. The corresponding DNA molecule is selected from the group consisting of SEQ ID NO:2, SEQ ID NO:4 and SEQ ID NO:5.

The CFTR proteins of the present invention which comprise a partially deleted R domain can be made by introducing the DNA molecules of the present invention into cells in culture using standard techniques (e.g. via calcium phosphate or calcium chloride co-precipitation, or via infection with a recombinant virus, such as a recombinant adenovirus, comprising the DNA molecule, DEAE dextran mediated transfection, lipofection, or electroporation). Recombinant cells can then be cultured in vitro in a manner that allows expression of the CFTR proteins of the present invention. Preferred host cells for generating the CFTR proteins of the present invention include, inter alia, mammalian cells, such as HeLa cells, COS cells, C127 cells; yeast cells, insect cells and bacterial cells.

The CFTR proteins of the present invention which comprise partially deleted R domains can be purified from host cell membranes using known methods, such as ion exchange chromatography, gel filtration chromatography, electrophoresis and affinity chromatography. (Tilly et. al., 1992, *The Journal of Biological Chemistry* 2679470-73). A preferred method of purification involves first solubilizing the protein in the presence of a nondenaturing detergent.

The CFTR proteins of the present invention comprising partially deleted R domains produced as described herein can be used, for example, in protein replacement therapies and the DNA molecule in gene therapies for Cystic Fibrosis as described in detail below.

Protein therapy may be accomplished by any method that effectively introduces the CFTR protein of the present invention into the membrane of CF defective cells to imbue on those cells CFTR activity. An effective amount of a CFTR protein of the present invention comprising a partially deleted R domain (i.e. an amount sufficient to reduce or eliminate the symptoms associated with CF and/or to provide a functional chloride ion channel in CF airway epithelia cells) can be administered alone or in association with an agent that facilitates passage (e.g. via fusion or endocytosis) through cell membranes to CF patients (i.e. patients having CF defective cells). The "effective amount" can be determined by one of skill in the art based on such factors as the type and severity of symptoms being treated, the weight and/or age of the subject, the previous medical history of the subject, and the selected route for administration of the agent.

Preferably for use in protein therapy, the CFTR proteins comprising partially deleted R domains are associated with lipids, such as detergents or other amphipathic molecule micelles, membrane vesicles, liposomes, virosomes, or microsomes. Lipid compositions that are naturally fusogenic or can be engineered to become fusogenic (e.g. by incorporating a fusion protein into the lipid) are especially preferred. Fusion proteins can be obtained from viruses such as parainfluenza viruses 1-3, respiratory syncytial virus (RSV), influenza A, Sendai virus, and togavirus fusion protein. Nonviral fusion proteins include normal cellular proteins that mediate cell-cell fusion. Other nonviral fusion proteins include the sperm protein PH-30 which is an integral membrane protein located on the surface of sperm cells that is believed to mediate fusion between the sperm and the egg. See Blobel et al., 1992, Nature 356:248-251. Still other nonviral fusion proteins include chimeric PH-30 proteins such as PH-30 and the binding component of hemaglutinin from influenza virus and PH-30 and a disintegrin (e.g. bitistatin, barbourin, kistrin, and echistatin). In addition, lipid membranes can be fused using traditional chemical fusogens such as polyethylene glycol (PEG).

A CF patient can be treated by administration of an effective amount of a CFTR protein comprising a partially deleted R domain, optionally in a pharmaceutically acceptable carrier or diluent. An effective amount of a CFTR protein comprising a partially deleted R domain is an amount sufficient alleviate the symptoms of CF and/or an amount to provide a functional chloride ion channel in CF airway epithelia cells. A CFTR protein comprising a partially deleted R domain can be administered subcutaneously, intravenously, intraperitoneally, intramuscularly, parenterally, orally, submucosally, by inhalation, or other appropriate route of administration in an effective dosage range. A preferred route of administration is by inhalation (e.g. of an aerosolized pharmaceutical composition). If necessitated by a particular mode of administration, CFTR proteins comprising partially deleted R domains can be encapsulated within a material that protects it from enzymatic degradation. In addition, prior to administration, it may be useful to administer agents to clear mucus (e.g. using a DNAse) and/or bacterial infection.

Alternatively, a preparation of the gene encoding a CFTR protein comprising a partially deleted R domain can be incorporated into a suitable vector for delivering the gene into a CF patient's defective cells. As many of the symptoms of CF manifest themselves in the respiratory tract, the preparation can be delivered directly to the airways of CF patients.

The first generation of CF gene therapy may be transient and may require repeated delivery to the airways. Eventually, however, gene therapy may offer a cure for CF when the identity of the precursor or stem cell to air epithelial cells becomes known. If genetic material encoding CFTR proteins comprising partially deleted R domains were incorporated into airway stem cells, all subsequent generations of such cells would make authentic CFTR protein comprising a partially deleted R domain from the integrated sequences and would correct the physiological defect almost irrespective of the biochemical basis of the action of CFTR.

For use in treating CF, appropriate vectors must: 1) effectively infect lung epithelia or other tissue manifesting the disease and deliver the therapeutic nucleic acid encoding CFTR function; 2) be appropriately maintained in host cells; and 3) be safe. The following describes a number of approaches and vectors that may prove useful for performing CF gene therapy. The following listing, however, is not intended to be exhaustive and many other vectors should prove useful for performing gene therapy with the novel genes disclosed herein.

Retroviruses—Although defective retroviruses are one of the best characterized system (Miller, A. D., 1990, Blood 76:271), the major issue in relation to CF is the requirement for dividing cells to achieve DNA integration and gene expression. Were conditions found to induce airway cell division, the in vivo application of retroviruses, especially if repeated over many years, would necessitate assessment of the safety aspects of insertional mutagenesis in this context.

Adeno-Associated Virus—(AAV) is a naturally occurring defective virus that requires other viruses such as adenoviruses or herpes viruses as helper viruses (Muzyczka, N., 1992, Current Topics in Microbiology and Immunology 158:97). It is also one of the few viruses that may integrate its DNA into non-dividing cells. Vectors containing as little as 300 base pairs of AAV can be packaged and can integrate, but space for exogenous DNA is limited to about 4.5 kb. AAV vectors therefore may prove useful for expressing genes encoding the CFTR proteins of the present invention comprising partially deleted R domains, although genes encoding fall length CFTR approach AAV's upper limit. For reviews see Flotte, 1999, Curr. Opin. Mol. Ther. 1:510-516; Carter & Samulski, 2000, Int. J. Mol. Med. 6:17-27; and Athanasopoulos & Dickson, 2000, Int. J. Mol. Med 6:363-375. AAV has already been successfully used to produce Factor IX in humans with hemophilia B. In AAV vectors, viral genes are deleted, thereby minimizing cell-mediated immune responses. AAV vectors can transduce non-dividing cells, such as airway epithelia. And DNA molecule expression can be prolonged. Although, most previous studies have used type 2 AAV vectors, its receptor is on the basolateral membrane and thus inaccessible to vector applied apically. See, Summerford & Samulski, 1998, J. Virol. 72:1438-1445. Recent studies have discovered that type 5 AAV can efficiently transduce well-differentiated human airway epithelia, and that its receptor lies on the apical membrane. See Zabner et al., 2000, J. Virol. 74:3852-3858; Walters et al. 276:20610-20616 Type 6 AAV is also a promising vector for airway epithelia. See Halbert, Allen & Miller, 2001, J. Virol. 75:6615-6624.

Naked DNA—Naked plasmid can be introduced into muscle cells by injection into the tissue. Expression can extend over many months but the number of positive cells is low (Wolff, J. et al., 1989, Science 247:1465).

DNA-Lipid Complexes—Lipid carriers can be associated with naked DNA (e.g. plasmid DNA) to facilitate passage through cellular membranes. Cationic, anionic, or neutral lipids can be used for this purpose. However, cationic lipids are preferred because they associate better with DNA, which generally has a net negative charge. Cationic lipids have been shown to mediate intracellular delivery of plasmid DNA (Felgner, P. and Ringold, G. M., 1989, Nature 337: 387). Injection of cationic lipid plasmid DNA complexes into the circulation of mice has been shown to result in expression of the DNA in lung (Brigham, K. et al., 1989, Am. J. Med. Sci. 298:278). Instillation of cationic lipid plasmid DNA into lung has also been found to be expressed in epithelial cells but the efficiency of expression has been reported as being relatively low and transient (Hazinski, T. A. et al., 1991, Am. J Respir., Cell Mol. Biol. 4:206).

Receptor Mediated Entry—In an effort to improve the efficiency of plasmid DNA uptake, attempts have been made to utilize receptor-mediated endocytosis as an entry mechanisms and to protect DNA in complexes with polylysine (Wu, G. and Wu, C. H., 1988, J. Biol. Chem. 263:14621). One potential problem with this approach is that the incoming plasmid DNA enters the pathway leading from endosome to lysosome, where much incoming material is degraded. One solution to this problem is the use of transferrin DNA-polylysine complexes linked to adenovirus capsids (Curiel, D. T. et al., 1991, Proc. Natl. Acad. Sci. USA 88:8850). The latter enter efficiently but have the added advantage of naturally disrupting the endosome thereby avoiding shuttling to the lysosome.

Adenovirus—Defective adenoviruses may also be useful for CF gene therapy (Berkner, K. L., 1988, *BioTechniques* 6:616). Adenovirus can be manipulated such that it encodes and expresses the desired gene product, and at the same time is inactivated in terms of its ability to replicate in a normal lytic viral life cycle. In addition, adenovirus has a natural tropism for airway epithelia. The viruses are able to infect quiescent cells as are found in the airways, offering a major advantage over retroviruses. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al., 1974, *Am. Rev. Respir. Dis.* 109:233-238). Finally, adenovirus mediated gene transfer has been demonstrated in a number of instances including transfer of alpha-1-antitrypsin and CFTR to the lungs of cotton rats (Rosenfeld, M. A. et al., 1991, *Science* 252:431-434; Rosenfeld et al., 1992, *Cell* 68:143-155). Furthermore, extensive studies to attempt to establish adenovirus as a causative agent in human cancer were uniformly negative (Green, M. et al., 1979, *Proc. Natl. Acad. Sci. USA* 76:6606).

A first generation adenovirus encoding full length CFTR has been prepared and includes viral DNA derived from the common relatively benign adenovirus 2 serotype. A similar vector can be prepared to express CFTR proteins comprising partially deleted R domains. The E1a and E1b regions of the viral genome, which are involved in early stages of viral replication have been deleted. Their removal impairs viral gene expression and viral replication. The protein products of these genes also have immortalizing and transforming function in some non-permissive cells.

The following properties would be desirable in the design of a viral vector to transfer the gene for a CFTR protein comprising a partially deleted R domain to the airway cells of a CF patient. The vector should allow sufficient expression of the CFTR protein, while producing minimal viral gene expression. There should be minimal viral DNA replication and ideally no virus replication. Finally, recombination to produce new viral sequences and complementation to allow growth of the defective virus in the patient should be minimized.

The present invention is further illustrated by the following examples which in no way should be construed as being further limiting.

EXAMPLES

Example 1

Construction of CFTR Variants

DNA molecules encoding exemplary embodiments of CFTR proteins comprising partial deletions in the R domain were made in pTM1-CFTR4 by PCR deletion mutagenesis (Quik Change Mutagenesis™, Stratagene, La Jolla, Calif.) and confirmed by sequencing. Constructs were ligated into an adenovirus serotype 5 vector in which the CMV promoter drives cDNA expression. The exemplary CFTR proteins were named by the residues that were deleted; for example in Δ708-835, residues between and including aa 708 and 835 are deleted. An identical adenovirus expressing green fluorescent protein (GFP) was used as a negative control. FIG. 1A shows the eight variants constructed which include, Δ708-835 (SEQ ID NO:9), Δ708-759 (SEQ ID NO:10), Δ708-723/749-783/832-835 (SEQ ID NO:11), Δ708-723/749-783/819-835 (SEQ ID NO:12), Δ708-759/819-835 (SEQ ID NO:13), Δ760-835 (SEQ ID NO:14), Δ708-783 (SEQ ID NO:15), and Δ708-783/823-835 (SEQ ID NO:16). FIG. 1A indicates the deletions by crosshatching. Serines that are phosphorylated in vivo are indicated in FIG. 1A with residue number at the top. First and last residue of deleted regions are indicated above each construct. The number of nucleotides deleted in each variant is shown on the right of FIG. 1A.

Example 2

Protein Biochemistry

To confirm protein size and phosphorylation, HeLa cells were infected with 200 MOI of recombinant adenovirus in Eagles minimal essential media (EMEM) for 45 min. Cells were lysed 18-24 hr later, CFTR immunoprecipitated, and phosphorylated with $\gamma$-$^{32}$P-ATP and the catalytic subunit of PKA as described previously. Baldursson et al., 2001, *J. Biol. Chem.* 276:1904-1910. For pulse chase studies, HeLa cells were infected as above, and after 18-24 hr cells were methionine starved, labeled with $^{35}$S-methionine, and pulse-chase studies carried out as described previously (Ostedgaard, Zeiher & Welsh, 1999, *J. Cell Sci.* 112:2091-2098. Proteins were separated on 8% SDS-PAGE, stained, destained, dried and exposed to phosphorscreens. After phosphorimaging, counts in bands B (immature) and C (mature) were quantitated. FIGS. 4A&B show that two representative CFTR proteins of the present invention comprising partially deleted R domains, namely Δ708-759 and Δ708-723/749-783/832-835, demonstrate similar disappearance of band B and appearance of band C as wild type. FIG. 4A shows the appearance in a gel and FIG. 4B is the quantitation of the bands from 3-4 experiments. Band B is shown as counts relative to counts at time=0; band C is shown as counts relative to counts at time=0.5 hr. (n=3-4 for all points.)

Example 3

Well-differentiated CF Airway Epithelia

Figure 2:
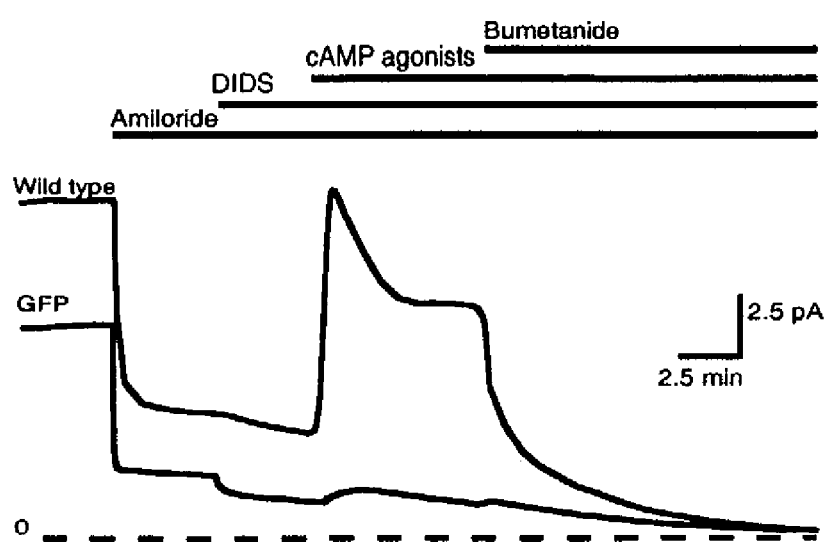
FIG. 2 shows an example of short-circuit current in well-differentiated airway epithelia expressing wild type CFTR and GFP.

Cultures of human airway epithelia were obtained from CF bronchus (ΔF508/ΔF508 or ΔF508/other genotypes) and cultured at the air-liquid interface as previously described (Karp et al., 2002, *Epithelial Cell Culture Protocols*, ed. Wice (Human, Totowa, N.J.) 188:115-137, incorporated herein by reference. Epithelia were used at least 14 days after seeding when they were well-differentiated with a surface consisting of ciliated cells, goblet cells and other non-ciliated cells. They also retained the functional properties of airway epithelia including transepithelial electrolyte transport and resistance. FIG. 2 shows the short circuit current in well-differentiated airway epithelia in the presence of wild-type CFTR and GFP, demonstrating that wild-type CFTR can provide a functional chloride ion channel in CF airway epithelia. Bars at top of FIG. 2 indicate additions to solutions (detailed below in Example 5). Zero current level is shown by dashed line.

Epithelia were infected with 200 MOI adenovirus vector using 5 mM EGTA applied to the apical surface to transiently disrupt the tight junctions as previously described (Walters et al., 1999, *J. Biol. Chem.* 274:10219-10226.

Example 4

Immunocytochemistry

Figure 5:
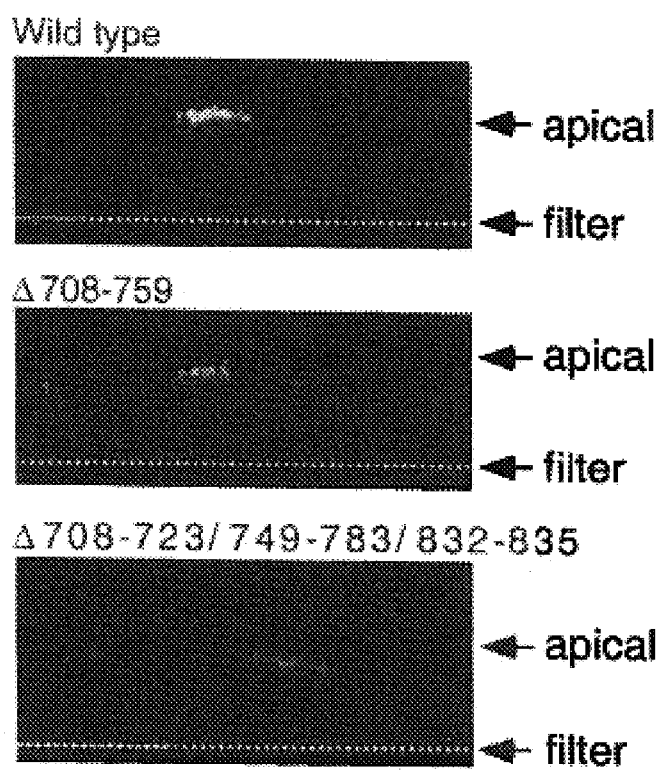
FIG. 5 is an immunostaining of differentiated airway epithelia expressing exemplary embodiments of the CFTR proteins of the present invention.

Three days following gene transfer, epithelia were fixed with 4% paraformaldehyde, permeabilized with 0.2% Triton X-100, blocked with 5% normal goat serum in SuperBlock (Pierce, Rockford, Ill.), and stained with anti-CFTR (24-1, R&D Systems, Minneapolis, Minn.) and anti-ezrin primary antibodies. Appropriate Alexa Fluor-conjugated secondary antibodies were then applied and epithelia were examined by confocal laser scanning microscopy. FIG. 5 shows X-Z confocal image reconstructions.

Example 5

Ussing Chamber Studies

Three days following gene transfer, short-circuit current was measured in symmetrical solutions containing: 135 mM NaCl, 1.2 mM $MgCl_2$, 1.2 mM $CaCl_2$, 2.4 mM $K_2PO_4$, 0.6 mM $KH_2PO_4$, 5 mM dextrose and 5 mM Hepes, pH 7.4, as previously described (Zabner et al., 1998, *Mol. Cell* 2:397-403. After measuring baseline current, mucosal amiloride ($10^{-4}$ M), mucosal 4,4'-diisothiocyanoto-stilbene-2,2'-disulfonic acid (DIDS, $10^{-4}$ M); the cAMP agonists mucosal forskolin ($10^{-5}$ M) plus 3-isobutyl-2-methylxanthine (IBMX, $10^{-4}$ M), and submucosal bumetanide ($10^{-4}$ M) were sequentially added (see FIG. 2). For a limited number of studies, epithelia were treated with forskolin ($10^{-5}$ M) and IBMX ($10^{-4}$ M) for 24 hr prior to study in Ussing chambers to minimize basal CFTR current.

Example 6

Patch-clamp Studies

The methods, solutions, and procedures for excised, inside-out patch-clamp recording were identical to those previously described (Carson, Travis & Welsh, 1995, *J. Biol. Chem.* 270:1711-1717). Patches containing multiple CFTR channels were studied at room temperature (~24° C.) in the presence of 1 mM ATP±75 nM PKA added to the bath solution. Membrane voltage was clamped at −40 mV; data were filtered at 100 Hz and digitized at 250 Hz.

Example 7

Nasal Voltage Study in CF Mice

For in vivo analysis, we used 6-8 wk old ΔF508 homozygote CF mice (Zeiher et al., 1995, *J. Clin. Invest.* 962051-2064. Mice were lightly anesthetized in a halothane chamber. Adenovirus vectors ($5 \times 10^9$ particles) were administered intranasally as Ad:CaPi coprecipitates (Fasbender et al., 1998, *J. Clin. Invest.* 102:184-193) in two 5 µl instillations delivered 5 min apart. Four days later animals were anesthetized with ketamine and xylazine and the transepithelial electric potential difference across the nasal epithelium (Vt) was measured as previously described (Zeiher et al., 1995, *J. Clin. Invest.* 96:2051-2064). During measurement of Vt, the nasal mucosa was perfused at a rate of 50 µl/min with a Ringer's containing (in mM) 135 NaCl, 2.4 $KH_2PO_4$, 0.6 $K_2HPO_4$, 1.2 $CaCl_2$, 1.2 $MgCl_2$, and 10 HEPES (pH 7.4 with NaOH). Three solutions were used: a) Ringer's containing 100 µM amiloride; b) Ringer's containing 135 mM Na-gluconate substituted for NaCl plus amiloride; and c) Na-gluconate Ringer's containing 10 µM isoproterenol and amiloride. Measurements were made after perfusion for 5 min.

Example 8

Results

A. Generation of CFTR with R Domain Deletions

Portions of the R domain were selectively deleted based on known PKA motifs and earlier structure and function studies (Ostedgaard, Baldursson, & Welsh, 2001, *J. Biol. Chem.* 276:7689-7692; Sheppard & Welsh, 1999, *Physiol. Rev.* 79:S23-S45; and Gadsby & Nairn, 1999, *Physiol Rev.* 79:S77-S107). Because previous work showed that residues 708-835 are the largest deletion that yields a functional channel in mammalian cells (Rich et al., 1993, *Receptors Channels* 1:221-232), deletions were made in this region. In addition, constructs were produced that retained different numbers of the phosphoserines. FIG. 1A shows the deletion constructs. The cDNA for each variant was inserted into a recombinant adenovirus vector. Infection of HeLa cells produced approximately equivalent amounts of protein of the predicted size; it was recognized by CFTR antibodies and was phosphorylated in vitro by the catalytic subunit of PKA.

B. Function of R Domain Variants in Well-differentiated CF Airway Epithelia

To determine whether the R domain variants can complement the CF Cl⁻ transport defect, the variants were expressed in well-differentiated CF airway epithelia and the short-circuit current response to several interventions was measured. FIG. 2 shows the interventions and an example of the currents. The following were sequentially added: a) amiloride to inhibit apical Na⁺ channels, hyperpolarize the apical membrane, and thereby generate a driving force for Cl⁻ secretory currents; b) DIDS to inhibit DIDS-sensitive apical Cl⁻ channels; c) cAMP agonists to activate CFTR; and d) bumetanide to inhibit basolateral Cl⁻ co-transport. Under these conditions, bumetanide-sensitive current provides the most accurate assessment of CFTR-dependent transepithelial Cl⁻ transport.

All the CFTR variants produced transepithelial Cl⁻ currents (FIG. 1B). The data in FIG. 1B represent the difference in current generated by adding bumetanide corrected for current in GFP expressing epithelia and normalized to current generated by wild type CFTR. Bumetanide-sensitive current for epithelia expressing wild type CFTR was 20.3±1.6 µA.cm⁻². The asterisks in FIG. 1B indicate the value different from wild type ($p<0.05$, one way ANOVA) (n=18 for wild type and 6-15 for each variant).

Because the constructs in CF epithelia obtained from multiple different lungs were tested, in each culture the responses of the variants were compared to epithelia expressing GFP (as a negative control) and then normalized current to the response of wild-type CFTR. As shown in FIG. 1B, the Δ708-835 variant generated the least Cl⁻ current, consistent with patch-clamp studies showing that this channel has a low open state probability ((Winter & Welsh, 1997, *Nature* 389:294-296; and Rich et al., 1993, *J. Biol. Chem.* 268:20259-20267). Two variants generated current similar to wild-type CFTR: Δ708-759 and Δ708-723/749-783/832-835 (FIG. 1B). The other variants produced intermediate levels of Cl⁻ current (FIG. 1B).

Amiloride-inhibited current has been reported to be increased in CF epithelia (Boucher, 1994, *Am J. Respir. Crit. Care Med.* 150:271-281; Schweibert et al., 1999, *Physiol.*

Rev. 79:S145-S166). However, the responsible mechanism remains uncertain and a direct effect of CFTR on the $Na^+$ currents has not been uniformly observed (Schweibert et al., 1999, Physiol. Rev. 79:S145-S166; and Nagel et al., 2001, EMBO Rep. 2:249-254). Prior studies showed limited and variable effects on $Na^+$ current. However, in the present invention, amiloride-inhibited current is influenced not only by the activity of epithelial $Na^+$ channels, but also by the basal $Cl^-$ current which is increased when amiloride hyperpolarizes the apical membrane. Moreover, in the present invention, there was no control for the percentage of cells infected in different experiments. Although gene transfer to 5-10% of cells is sufficient to correct the CF $Cl^-$ transport defect (Davies, Geddes, & Alton, 2001, J. Gene Med. 3:409-417; Flotte, 1999, Curr. Opin. Mol. Ther. 1:510-516; and Welsh, 1999, J. Clin. Invest. 104:1165-1166), alteration of $Na^+$ current may depend on the percentage of infected cells over a wide range (Johnson et al., 1995, J. Clin. Invest 95:1377-1382).

Patch-clamp studies in heterologous cells demonstrated that some of the CFTR proteins of the present invention comprising partially deleted R domains opened even without PKA phosphorylation; i.e., they were constitutively active (Ostedgaard, Baldursson, & Welsh, 2001, J. Biol. Chem. 276:7689-7692). To assess constitutive activity, epithelia were first treated with cAMP agonists for 24 hr prior to mounting them in Ussing chambers; this treatment minimizes basal CFTR $Cl^-$ channel activity. Then the current remaining after treatment with amiloride and DIDS, but before addition of cAMP agonists was measures, as shown in FIG. 1C, and FIG. 2). In FIG. 1C, the basal current was measured in the presence of amiloride and DIDS and corrected for current in epithelia expressing GFP. All epithelia were pre-treated with cAMP agonists for 24 hr. Asterisks in FIG. 1C indicate values different from wild type ($p<0.05$, one way ANOVA) (n=3-6 for each construct).

Interestingly, Δ708-835 produced a large basal current, consistent with previous patch-clamp studies showing that it generates significant constitutive but little total $Cl^-$ current. Wild type and the other CFTR proteins of the present invention comprising partially deleted R domains surprisingly showed low basal/constitutive current. In one embodiment of the present invention, such low basal/constitutive current is preferred.

C. Constitutive Activity of CFTR with R Domain Deletions

Figure 3:
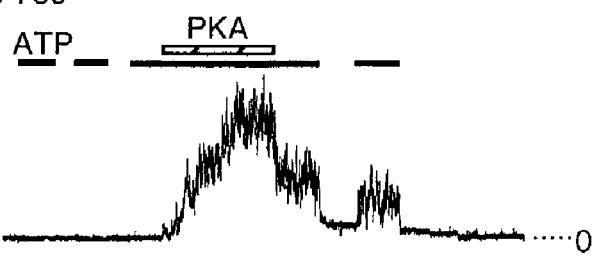
FIG. 3 shows the current from inside-out patches of membrane containing multiple CFTR channels in the presence of 1 mM ATP and PKA. 3 A is Δ708-759, and 3B is Δ708-723/749-783/832-835.
Figure 3:
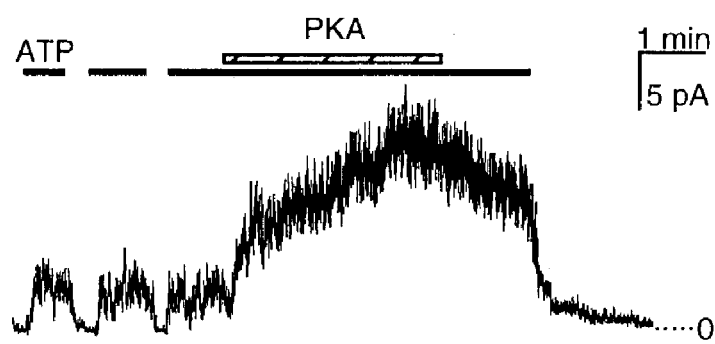

To test further for constitutive activity, we examined the two variants generating the largest $Cl^-$ currents in airway epithelia by expressing them in HeLa cells and measuring activity in excised, inside-out patches. Consistent with the transepithelial studies shown in FIG. 1C, FIG. 3 shows that Δ708-723/749-783/832-835, but not Δ708-759 generated constitutive current. Specifically, FIG. 3A shows that Δ708-759 showed no current before phosphorylation with PKA and FIG. 3B shows that Δ708-723/749-783/832-835 activity was stimulated with ATP alone. The ratio of current with ATP alone to the maximal current with PKA and ATP was 0.22±0.01, n=4.

D. Biosynthesis and Localization of the R Domain Variants

Figure 4:
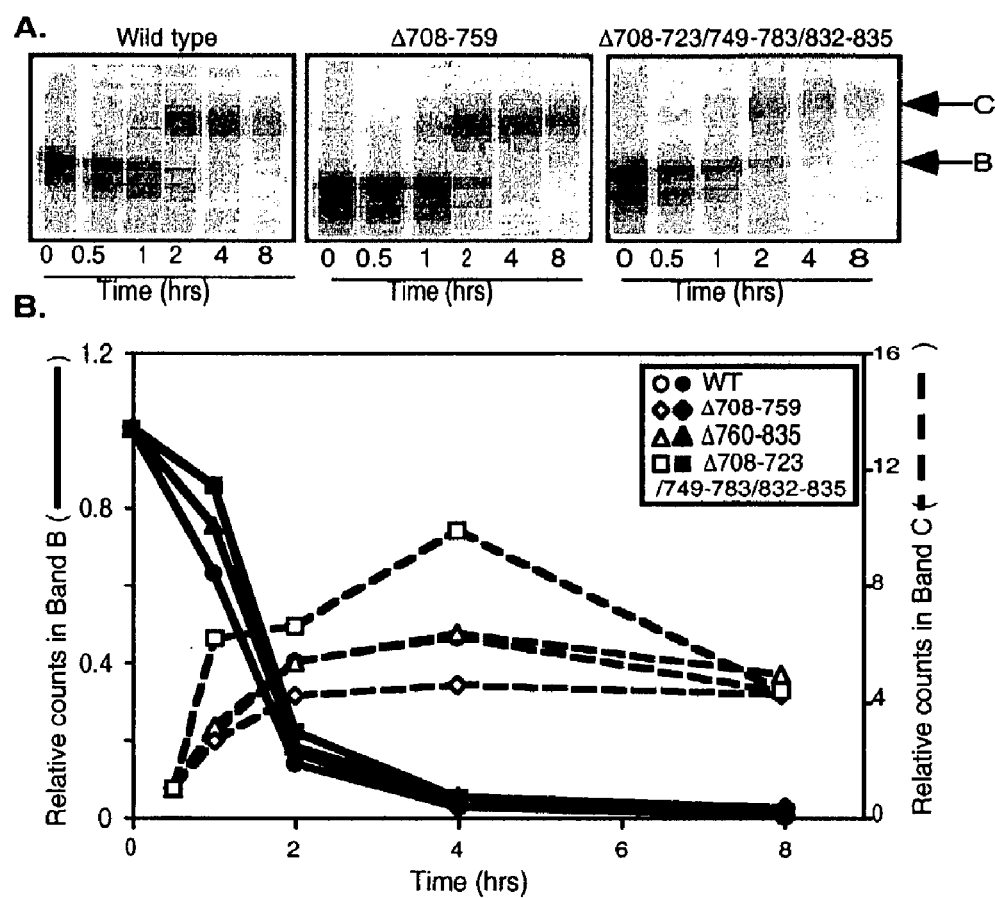
FIG. 4A depicts gels showing CFTR at indicated time after pulse with ³⁵S-methionine and showing the disappearance of band B (immature) and band C (mature); 4B is a graph plotting the number of counts in band B (solid lines) and band C (dashed lines) which were determined by phosphorimaging.

The glycosylation state of CFTR traces its progress through the biosynthetic pathway (Cheng et al., 1990, Cell 63:827-834). In the endoplasmic reticulum, CFTR appears as a partially glycosylated intermediate, band B (immature). In the Golgi complex, the protein becomes fully glycosylated, appearing as band C (mature); this is the form that traffics to the plasma membrane. A pulse-chase analysis to assess biosynthesis of the R domain variants was used. FIG. 4 shows results for wild-type CFTR and three of the CFTR proteins comprising partially deleted R domains of the present invention. The rates at which band B disappeared and band C appeared were similar for each of the CFTR proteins of the present invention and wild type.

CFTR resides in the apical membrane of non-CF epithelia where it provides a pathway for $Cl^-$ flow (Welsh et al., 2000, The Metabolic and Molecular Basis of Inherited Disease, eds. Scirver, Beaudet, Sly, Valle, Childs & Vogelstein (McGraw-Hill, New York) pp 5121-5189); an apical location is critical for its function in transepithelial $Cl^-$ transport. The exemplary embodiments of CFTR proteins comprising partially deleted R domains of the present invention were expressed in well-differentiated CF airway epithelia, immunostained CFTR, and the pattern of fluorescence using confocal microscopy was examined. All the constructs showed the same apical localization as wild type CFTR; FIG. 5 shows examples for Δ708-759 and Δ708-723/749-783/832-835. In FIG. 5, data are X-Z confocal images. Arrows indicate the position of the apical membrane and the top of the filter support. Anti-CFTR immunostaining is green and anti-ezrin staining is red. Ezrin stains the apical region of the epithelial cells.

E. In vivo Function of R Domain Variants in the Nasal Epithelia of CF Mice

Figure 6:
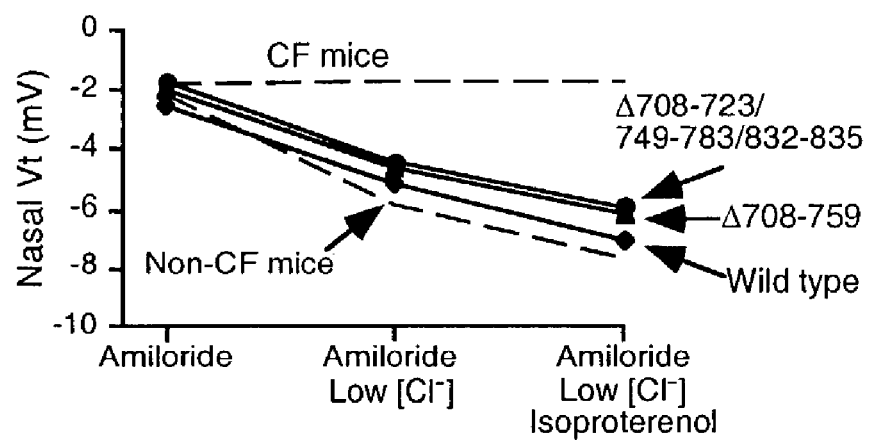
FIG. 6 shows the voltage across nasal epithelium (Vt) in CF mice expressing indicated exemplary embodiments of the CFTR proteins of the present invention in the nasal mucosa.

As an additional test of their combined biosynthesis, localization, and functional activity, the variants were tested in an art recognized animal model in vivo. Zeiher et al., 1995, J. Clin. Invest. 96:2051-2064. Nasal epithelia of CF mice were infected with adenovirus vectors expressing wild type and the two CFTR proteins of the present invention that generated the largest $Cl^-$ current in human airway epithelia. Epithelia were treated with amiloride to inhibit $Na^+$ channels and then Vt in response to perfusion was measured with solutions containing a low $Cl^-$ concentration and isoproterenol to elevate cellular cAMP levels. As shown in FIG. 6, Expression of Δ708-759 and Δ708-723/749-783/832-835 corrected the nasal voltage defect to a similar extent as wild-type CFTR and to levels similar to those previously observed in non-CF mice (Zeiher et al., 1995, J. Clin. Invest. 96:2051-2064). In FIG. 6, values of Vt obtained from untreated CF and wild type mice are indicated by dashed lines. The three interventions are indicated at the bottom of FIG. 6 (n=13 for wild type and 14 for the deleted variants).

The data show that CFTR constructs with multiple R domain deletions retain normal biosynthesis, apical targeting and $Cl^-$ channel function when expressed in differentiated CF airway epithelia. These results have implications for developing CF gene therapy and for understanding CFTR structure and function.

The data also establish the feasibility to generate a smaller CFTR DNA molecule to accommodate the limited packaging capacity of AAV in vitro and in vivo. For optimal use in an AAV vector for CF gene therapy, the DNA molecule would have two characteristics. The DNA molecule would be short to facilitate packaging, and the protein product would correct the CF defect to the same extent as wild type CFTR.

Of these three constructs, Δ708-759 most closely resembled wild type, in that it produced no constitutive $Cl^-$ current. In contrast, Δ708-723/749-783/832-835 and Δ708-759/819-835 had greater, but still low, basal $Cl^-$ currents than wild type and showed constitutive $Cl^-$ current when examined in patch-clamp studies.

Example 9

Structure of CFTR

The CFTR proteins of the present invention which comprise partially deleted R domains provide insight into CFTR structure. All the CFTR proteins comprising partially deleted R domains of the present invention were capable of targeting exclusively to the apical membrane, indicating that important apical targeting motifs are not likely located within this region of the R domain. CFTR proteins of the present invention also showed normal biosynthesis, suggesting that sequences in the deleted regions are not required for normal processing. Apical targeting and biosynthesis were also normal with and without constitutive activity, suggesting that Cl⁻ channel activity may not influence these processes. Other studies have shown that R domain deletions and missense mutations in this region of the R domain generate band C (mature) protein (see Vankeerberghen et al., 1999, *Biochemistry* 38:14988-14998; and Vankeerberghen et al., 1998, *Hum. Mol. Genet.* 7:1761-1769). Other studies have also shown that elimination of a single arginine-framed motif (residues 764-766) did not impair processing (Chang et al., 1999, *Mol. Cell* 4:137-142).

The CFTR proteins comprising partially deleted R domains of the present invention reveal several aspects of R domain function. a) Length. In general, the more the R domain deleted, the less the Cl⁻ current. However, length alone does explain the results as evidenced by the finding that Δ708-783/823-835 (267 bp deleted) had as much current as Δ708-723/749-783/819-835 (204 bp deleted). b) Specific phosphoserines. Although all of the CFTR proteins of the present invention retained Ser660 and Ser700, the number of additional phosphoserines failed to predict the amount of current. For example, Δ760-835 (with one additional phosphoserine) had at least as much current as Δ708-783 (two additional phosphoserines) and Δ708-723/749-783/819-835 (three additional phosphoserines). These results are consistent with previous work suggesting that not all the phosphoserines are necessary for activity and no one phosphoserine is dominant. c) Charge. No correlation between Cl⁻ current and net charge present within the region between aa 708 and 835 was found. d) Ser737. Mutation of Ser737 suggested it has an inhibitory function on CFTR studied in Xenopus oocytes (Wilkinson et al., 1997, *Am J. Physiol.* 273:L127-L133). In airway epithelia, the CFTR proteins comprising partially deleted R domains of the present invention did not reveal inhibition. e) Residues 817-838. This stretch of negatively charged amino acids has been suggested as a stimulatory region (Xie et al., 2000, *Biophys. J.* 78:1293-1305). Deletion of this region decreased current in Δ708-723/749-783/819-835 compared to Δ708-723/749-783/832-835. However, deletion of this region in Δ708-783/823-835 did not reduce current as compared to Δ708-783. f) Residues 760-783. It was previously suggested that these residues prevented constitutive activity (Baldursson et al., 2001, *J. Biol. Chem.* 276:1904-1910). The present invention provides support for this hypothesis. g) Structure. The ability to alter the sequence of the R domain in so many different ways and yet retain Cl⁻ channel function and phosphorylation-dependent activity supports the hypothesis that there are few or no required structural motifs in this portion of the R domain. That conclusion is consistent with the recent finding that this region of the R domain is predominantly random coil (Ostedgaard et al., 2000, *Proc. Natl. Acad. Sci.* 97:5657-5662).

---

We claim:

1. An isolated and purified DNA molecule having the sequence set forth in SEQ ID NO:2.
2. A vector comprising the DNA molecule of claim 1.
3. The vector of claim 2, wherein the vector is adeno-associated virus (AAV).
4. The vector of claim 3, wherein the vector is selected from the group consisting of AAV type 5 or AAV type 6.
5. The vector of claim 2, wherein the vector is adenovirus.

* * * * *